US012385036B2

(12) United States Patent
Bayley et al.

(10) Patent No.: US 12,385,036 B2
(45) Date of Patent: Aug. 12, 2025

(54) PROMOTERS AND COMPOSITIONS

(71) Applicant: Oxford University Innovation Limited, Oxfordshire (GB)

(72) Inventors: Hagan Bayley, Oxfordshire (GB); Michael Booth, Oxfordshire (GB)

(73) Assignee: Oxford University Innovation Limited, Oxford (GB)

( * ) Notice: Subject to any disclaimer, the term of this patent is extended or adjusted under 35 U.S.C. 154(b) by 758 days.

(21) Appl. No.: 16/081,292

(22) PCT Filed: Feb. 28, 2017

(86) PCT No.: PCT/GB2017/050538
§ 371 (c)(1),
(2) Date: Aug. 30, 2018

(87) PCT Pub. No.: WO2017/149293
PCT Pub. Date: Sep. 8, 2017

(65) Prior Publication Data
US 2019/0062729 A1  Feb. 28, 2019

(30) Foreign Application Priority Data
Mar. 1, 2016 (GB) .................................. 1603591

(51) Int. Cl.
| C12N 15/113 | (2010.01) |
| B01L 3/00 | (2006.01) |
| C12N 15/10 | (2006.01) |
| C12N 15/64 | (2006.01) |
| C12N 15/66 | (2006.01) |
| C12N 15/67 | (2006.01) |
| C12N 15/89 | (2006.01) |

(52) U.S. Cl.
CPC ........ *C12N 15/1037* (2013.01); *B01L 3/5082* (2013.01); *C12N 15/113* (2013.01); *C12N 15/64* (2013.01); *C12N 15/66* (2013.01); *C12N 15/67* (2013.01); *C12N 15/895* (2013.01)

(58) Field of Classification Search
CPC .. C12N 15/1037; C12N 15/113; C12N 15/64; C12N 15/66; C12N 15/67; C12N 15/895; C12N 15/63; B01L 3/5082; C12P 21/00
See application file for complete search history.

(56) References Cited

U.S. PATENT DOCUMENTS

| 5,948,624 A * | 9/1999 | Rothschild ............. C07H 19/04 435/5 |
| 6,017,758 A * | 1/2000 | Haselton, III ......... C12N 15/63 435/243 |
| 6,114,153 A | 9/2000 | Shukla et al. |
| 11,549,097 B2 | 1/2023 | Bayley et al. |
| 2002/0155606 A1 * | 10/2002 | Okamoto ............. C07D 311/10 435/448 |
| 2005/0032118 A1 * | 2/2005 | Self ...................... G01N 33/542 435/7.1 |
| 2005/0085630 A1 * | 4/2005 | Olejnik .................... C07K 1/14 564/511 |
| 2007/0069408 A1 | 3/2007 | Cheng et al. |
| 2007/0099840 A1 | 5/2007 | Ulijn et al. |
| 2007/0178448 A1 * | 8/2007 | Tsao ....................... C12N 15/67 435/5 |
| 2007/0224273 A1 | 9/2007 | Xu et al. |
| 2010/0167938 A1 * | 7/2010 | Su ........................ C12Q 1/6874 506/7 |
| 2011/0306110 A1 | 12/2011 | Takeuchi et al. |
| 2013/0202802 A1 | 8/2013 | Gazda et al. |
| 2014/0271843 A1 | 9/2014 | Ma |
| 2014/0356289 A1 | 12/2014 | Bayley et al. |
| 2015/0217024 A1 | 8/2015 | Wang et al. |
| 2015/0248949 A1 | 9/2015 | Bayley et al. |
| 2019/0024034 A1 | 1/2019 | Bayley et al. |
| 2019/0093071 A1 | 3/2019 | Bayley et al. |

FOREIGN PATENT DOCUMENTS

| CN | 1520306 | 8/2004 |
| CN | 1994478 | 7/2011 |
| CN | 104353123 | 2/2015 |
| CN | 104936682 | 9/2015 |
| WO | 02/062357 | 8/2002 |

(Continued)

OTHER PUBLICATIONS

Liang et al. Photocleavable biotin derivatives: A versatile approach for the isolation of biomolecules. 2007. Nucleic Acids Symposium Series No. 51 349-350 (Year: 2007).*

Hobartner and Silverman. Photocleavable biotin derivatives: A versatile approach for the isolation of biomolecules. Angew. Chem. 2005, 117, 7471-7475 (Year: 2005).*

Olejnik et al. Photocleavable biotin derivatives: A versatile approach for the isolation of biomolecules. 1995 Proc. Natl. Acad. Sci. USA vol. 92, pp. 7590-7594 (Year: 1995).*

Fujii et al. In vitro evolution of α-hemolysin using a liposome display. 2013. PNAS. vol. 110, No. 42, 16796-16801 (Year: 2013).*

Timko et al. Light regulation of plant gene expression by an upstream enhancer-like element. 1985. Nature vol. 318, p. 579-582 (Year: 1985).*

(Continued)

*Primary Examiner* — Jennifer Dunston
*Assistant Examiner* — Tiffany Nicole Grooms
(74) *Attorney, Agent, or Firm* — Hamilton, Brook, Smith & Reynolds, P.C.

(57) ABSTRACT

The present invention relates to activatable promoters, as well as expression systems, vectors, delivery systems, reaction vessels, aqueous objects and compositions comprising said activatable promoters. The invention also provides compositions comprising assemblies and networks of aqueous objects comprising said activatable promoters. The invention additionally provides methods of expressing a transcript and methods of expressing a polypeptide using the activatable promoters of the invention. The invention further provides phospholipid mixtures, as well as aqueous objects and compositions comprising said phospholipid mixtures.

29 Claims, 26 Drawing Sheets

Specification includes a Sequence Listing.

(56) References Cited

FOREIGN PATENT DOCUMENTS

| WO | WO 2007/043048 | 4/2007 |
|---|---|---|
| WO | 2011151832 A1 | 12/2011 |
| WO | WO 2013/064837 A1 | 5/2013 |
| WO | 2013113883 | 8/2013 |
| WO | 2014/06444 | 5/2014 |
| WO | WO 2014/064459 | 5/2014 |
| WO | WO 2014/064461 | 5/2014 |
| WO | WO 2014/087175 | 6/2014 |
| WO | WO 2014/132262 | 9/2014 |
| WO | WO 2014/200997 | 12/2014 |
| WO | WO 2016/142637 | 9/2016 |

OTHER PUBLICATIONS

Yamaguchi et al. Light-activated gene expression from site-specific caged DNA with a biotinylated photolabile protection group. Chem. Commun., 2010, 46, 2244-2246 (Year: 2010).*
Hussein Journal of Biotechnology 359 (2022) 185-193 (Year: 2022).*
PEGFP-N1 Vector Information Clontech Laboratories, Inc. Internet: www.clontech.com Protocol # PT3027-5 2 Version # PR93634 (Year: 1999).*
Su et al. Photoresponsive nucleic acids for gene regulation. Journal of Chinese Pharmaceutical Sciences 19 (2010) 5-14) (Year: 2010).*
Abkarian et al, "Continuous droplet interface crossing encapsulation (cDICE) for high throughput monodisperse vesicle design" Soft Matter 7, 4610 (2011).
Arkin, "Synthetic cell biology", Curr Opin Biotechnol. 12(6)638-44 (2001).
Atala et al. "3D bioprinting of tissues and organs", Nat Biotechnol, 32(8): 773-785 (2014).
Bai et al, "Photocleavage of a 2-nitrobenzyl linker bridging a fluorophore to the 5' end of DNA", PNAS, vol. 100, No. 2, 409-413 (2003).
Bayley, H., et al., "Droplet interface bilayers", Mol. Biosyst. 4, 1191-1208 (2008).
Beckert, B., et al, "Synthesis of RNA by in vitro transcription", Methods Mol. Biol. 703: pp. 29-41 (2011). [doi: 10.1007/978-1-59745-248-9_3].
Booth, M.J., "Light-activated communication in synthetic tissues", Sci. Adv. 2, 4 (2016).
Boshart et al, "A very strong enhancer is located upstream of an immediate early gene of human cytomegalovirus", Cell, 41:521-530 (1985).
Bubeck, P., et al., "Rapid cloning by homologous recombination in vivo", Nucleic Acids Res. 21, 3601 (1993).
Calvert, P., "Printing Cells", Science, 318, 208-209 (2007).
Dahl et al, "Microfluidic Strategies for Understanding the Mechanics of Cells and Cell-Mimetic Systems" Annu Rev Chem Biomol Eng. 6:293-317 (2015).
Derby, B., "Printing and Prototyping of Tissues and Scaffolds", Science 338, 921-926 (2012).
Diguet, A., et al, "UV-induced bursting of cell-sized multicomponent lipid vesicles in a photosensitive surfactant solution", J. Am. Chem. Soc. 134, 4898 (2012).
Duarte Campos et al. "The Stiffness and Structure of Three-Dimensional Printed Hydrogels Direct the Differentiation of Mesenchymal Stromal Cells Toward Adipogenic and Osteogenic Lineages", Tissue Engineering Part A 21(3 and 4): 740-756 (2015).
Duarte Campos et al. "Three-dimensional printing of stem cell-laden hydrogels submerged in a hydrophobic high-density fluid", Biofabrication 5, 015003, 11 pages (2013).
Elani et al "Vesicle-based artificial cells as chemical microreactors with spatially segregated reaction pathways", Nat. Commun. 5, 1-5 (2014).
Elani et al, "Engineering multi-compartment vesicle networks", Chem. Sci. 4, 3332-3338 (2013).
Elani et al., "Novel technologies for the formation of 2-D and 3-D droplet interface bilayer networks", Lab Chip 12, 3514-20 (2012).

Estevez-Torres, A., et al, "Sequence-independent and reversible photocontrol of transcription/expression systems using a photosensitive nucleic acid binder", Proc. Natl. Acad. Sci. U. S. A. 106, 12219 (2009).
Fedoryshin et al, "Near-Infrared-Triggered Anticancer Drug Release from Upconverting Nanoparticles", ACS Applied Materials & Interfaces, 6, 13600-13606 (2014).
Foty, R, J. "A simple hanging drop cell culture protocol for generation of 3d spheroids", Vis. Exp. 20, 4-7, 2011.
Fujii, S., et al., "In vitro evolution of alpha- hemolysin using a liposome display", Proc. Natl. Acad. Sci. U. S. A. 110, 16796 (2013).
Gorka et al, "A Near-IR Uncaging Strategy Based on Cyanine Photochemistry" J. Am. Chem. Soc, 136, 14153-14159 (2014).
Gudapate, H. et al. "A comprehensive review on droplet-based bioprinting: Past, present and future", Biomaterials 102, 20-42 (2016).
Gurkan et al. "Engineering Anisotropic Biomimetic Fibrocartilage Microenvironment by Bioprinting Mesenchymal Stem Cells in Nanoliter Gel Droplets", Mol. Pharm. 11, 2151-9 (2014).
Haraguchi, Y, "Scaffold-free tissue engineering using cell sheet technology", RSC Adv. 2, 2184, (2012).
Hemphill, J., et al., "Site-Specific Promoter Caging Enables Optochemical Gene Activation in Cells and Animals", J. Am. Chem. Soc. 136 (2014).
Holden, M.A., et al., Functional bionetworks from nanoliter water droplets, J. Am. Chem. Soc. 129, 8650 (2007).
Howarth, M., et al, "A monovalent streptavidin with a single femtomolar biotin binding site", Nat. Methods 3, 267 (2006).
Hwang et al. "Asymmetric Droplet Interface Bilayers", J. Am. Chem. Soc. 130, 15854-64 (2008).
Hwang, W.L., et al., "Electrical behavior of droplet interface bilayer networks: experimental analysis and modeling", J. Am. Chem. Soc. 129, 11854-11864 (2007).
Ichihashi, N., "Darwinian evolution in a translation-coupled RNA replication system within a cell-like compartment", Nat. Commun. 4, 2494 (2013).
International Search Report for International Application No. A114, "Printing Of A Cellularised Scaffold": Date of Mailing: May 23, 2017.
International Search Report for International Application No. PCT/GB2017/050538, "Improved Promoters and Compositions": Date of Mailing: Jun. 30, 2017.
International Search Report for International Application No. PCT/GB2017/050542, "Phase Transfer of a Cargo Laden Scaffold": Date of Mailing: May 15, 2017.
Ito et al, "Dynamical formation of lipid bilayer vesicles from lipid-coated droplets across a planar monolayer at an oil/water interface", Soft Matter 9, 9539 (2013).
Kaneda, M., et al., "Direct formation of proteo-liposomes by in vitro synthesis and cellular cytosolic delivery with connexin-expressing liposomes", Biomaterials 30, 3971 (2009).
Karzbrun, E., et al., "Programmable on-chip DNA compartments as artificial cells", Science 345, 829 (2014).
Kolesky et al., "3D Bioprinting of Vascularized, Heterogeneous Cell-Laden Tissue Constructs", Adv. Mater. 26, 3124-30 (2014).
Konermann et al, "Optical control of mammalian endogenous transcription and epigenetics states", Nature, 500(7463), 472-476 (2013).
Kröck, L., et al., "Photoinduced Transcription by Using Temporarily Mismatched Caged Oligonucleotides", Angew Chem Int Ed Engl. 471-473, 44 (2005).
Lancaster et al., "Organogenesis in a dish: Modeling development and disease using organoid technologies", Science (80), 345(6194): 1247125 11 pages (2014).
Lentini, R., et al., "Integrating artificial with natural cells to translate chemical messages that direct *E. coli* behaviour", Nat. Commun. 5, 4012 (2014).
Li et al. "Rapid formation of a supramolecular polypeptide-DNA hydrogel for in situ three-dimensional multilayer bioprinting", Angew. Chemie Int. Ed. 54, 1-6a (2015).
Liu, M., "Azobenzene-tethered T7 promoter for efficient photoregulation of transcription", J. Am. Chem. Soc. 128, 1009 (2006).

(56) References Cited

OTHER PUBLICATIONS

Lu, W. C., "In vitro selection of proteins via emulsion compartments. Methods", 60, 75 (2013).
Maglia et al., "Droplet networks with incorporated protein diodes show collective properties", Nat. Nanotechnol. 4, 437-440 (2009).
Maglia, G. et al., "Analysis of single nucleic acid molecules with protein nanopores", Method. Enzymol. 475, 591-623 (2010).
Mannoor et al. "3D Printed Bionic Ears" Nano Lett. 13, 2634-2639 (2013).
Monroe, W. T., et al., "Targeting expression with light using caged DNA", J. Biol. Chem. 274, 30 (1999).
Murtas, "Artificial assembly of a minimal cell", Mol Biosyst. 5(11): 1292-7 (2009).
Murtas, G., et al., "Protein synthesis in liposomes with a minimal set of enzymes", Biochem. Biophys. Res. Commun. 363, 12 (2007).
Nishikawa, T., et al., "Construction of a gene screening system using giant unilamellar liposomes and a fluorescence-activated cell sorter", Anal. Chem. 84, 5017 (2012).
Noireaux, V., et al., "A vesicle bioreactor as a step toward an artificial cell assembly", Proc. Natl. Acad. Sci. U. S. A. 101, 17669 (2004).
Norotte et al. "Scaffold-free vascular tissue engineering using bioprinting", Biomaterials 30 (2009) 5910-5917.
Notification Concerning Transmittal of International Preliminary Report on Patentability for International Application No. PCT/GB2017/050538, "Improved Promoters and Compositions": Date of Mailing: Sep. 13, 2018.
Notification Concerning Transmittal of International Preliminary Report on Patentability for International Application No. PCT/GB2017/050541, "Printing Of A Cellularised Scaffold": Date of Mailing: Sep. 13, 2018.
Notification Concerning Transmittal of International Preliminary Report on Patentability for International Application No. PCT/GB2017/050542, "Phase Transfer of a Cargo Laden Scaffold": Date of Mailing: Sep. 13, 2018.
O'Hare et al, "Transformation of mouse fibroblasts to methotrexate resistance by a recombinant plasmid expressing a prokaryotic dihydrofolate reductase", Proc. Natl. Acad. Sci., vol. 78(3), p. 1527-31 (1981).
Olejnik, J., et al., "Photocleavable biotin derivatives: a versatile approach for the isolation of biomolecules", Proc. Natl. Acad. Sci. U. S. A. 92, 7590 (1995).
Onoe et al, "Cell-laden microfibers for bottom-up tissue engineering", Drug Discov. Today 20, 236-246 (2015).
Onoe, H, "Metre-long cell-laden microfibres exhibit tissue morphologies and functions", Nat. Mater. 12, 584-590, (2013).
Ozbolat et al. "Bioprinting toward organ fabrication: Challenges and Future Trends", IEEE Trans. Biomed. Eng. 60(3): 691-699, 79109 (2013).
Panyam et al, "Biodegradable nanoparticles for drug and gene delivery to cells and tissue", Adv Drug Deliv Rev, Sep. 13, 2012.
Pati et al., "Printing three-dimensional tissue analogues with decellularized extracellular matrix bioink", Nat. Commun. 5:3935, 11 pages (2014).
Pautot et al, "Engineering asymmetric vesicles", Proc. Natl. Acad. Sci. U.S.A. 100, 10718-10721, 100(19) (2003).
Presentation by M. Booth at the 'Compartmentalisation & Confinement in Biological Systems' workshop, run by the EPSRC Physics of Life network, from the Sep. 21/22, 2015 at Cripps Court, Magdalene College, Cambridge University.
Reimao-Pinto, M.M., et al., "Dual-color control of nucleotide polymerization sensed by a fluorescence actuator", Photochem. Photobiol. Sci. 13, 751-756 (2014).
Sanzone, A. P., t al., "Assessing the biocompatibility of click-linked DNA in *Escherichia coli*", Nucleic Acids Res. 40, 10567 (2012).
Schindler et al., "Photo-activatable Cre recombinase regulates gene expression in vivo", Nature Scientific Reports, 5:13627 (2015).
Seemann, R., et al., "Droplet based microfluidics", Reports on Progress in Physics 75 (2012).

Shimizu, Y., et al., "Cell-free translation reconstituted with purified components", Nat. Biotechnol. 19, 751-755 (2001).
Shimizu, Y., et al., "Protein synthesis by pure translation systems", Methods 36, 299 (2005).
Squires T. M., et al., "Microfluidics: Fluid physics at the nanoliter scale", Rev. Mod. Phys. 77, 977-1026 (2005).
Stano, "Minimal cells: relevance and interplay of physical and biochemical factors", Biotechnol J. 6(7):850-9 (2011).
Stanton-Humphreys et al, "Wavelength-orthogonal photolysis of neurotransmitters in vitro", Chem. Commun. 48, 657-659 (2012).
Syeda et al, "Screening blockers against a potassium channel with a droplet interface bilayer array", J. Am. Chem. Soc. 130, 15543-15548 (2008).
Takebe et al, "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Mol. Cell. Biol, vol. 8(1), p. 466-472 (1988).
Tawfik, D.S., et al., "Man-made cell-like compartments for molecular evolution", Nat. Biotechnol. 16, 652 (1998).
Villar et al, "A tissue-like printed material", Science 340, 48-52 (2013).
Villar et al, "Formation of droplet networks that function in aqueous environments", Nat. Nanotechnol. 6, 803-808 (2011).
Walde et al, "Giant Vesicles: Preparations and Applications", Chembiochem 11, 848-65 (2010).
Wang et al, "Spatiotemporal control of gene expression by a light-switchable transgene system", Nature Methods, vol. 9, No. 3 (2012).
Whitesides, G.M., "The origins and the future of microfluidics", Nature 442, 7101:368-373 (2006).
Written Opinion for International Application No. PCT/GB2017/050538, "Improved Promoters and Compositions", Date of Mailing: Sep. 8, 2018.
Written Opinion for International Application No. PCT/GB2017/050541, "3D Printing of a Cellularised Scaffold", Date of Mailing: Sep. 8, 2018.
Written Opinion for International Application No. PCT/GB2017/050542, "Phase Transfer of a Cargo Laden Scaffold": Date of Mailing: May 15, 2017.
Yamada et al, "Spontaneous Transfer of Phospholipid-Coated Oil-in-Oil and Water-in-Oil Micro-Droplets through an Oil/Water Interface", Langmuir 22, 9824-9828 (2006).
Yamaguchi, S., et al., "Control of gene expression using caged plasmids with functionalized photo-cleavable linkers", J. Biosci. Bioengineer. 108 (2009).
Yanagisawa et al, "Oriented Reconstitution of a Membrane Protein in a Giant unilamellar vesicle: experimental verification with the potassium channel KcsA", J. Am. Chem. Soc. 133, 11774-11779 (2011).
Zhang, Y., et al., "DNA cloning by homologous recombination in *Escherichia coli*", Nat. Biotechnol. 18, 1314 (2000).
Kamiya, et al, "Synthetic Gene Involving Azobenzene-Tethered T7 Promoter for the Photocontrol of Gene Expression by Visible Light," ACS Synth. Biol., 4:365-370 (2015).
Merriam-Webster definition: dispose; retrieved from the internet Apr. 3, 2021: https://www.merriam-webster.com/dictionary/dispose (Year: 2021).
T& T Scientific, Product Information for DPhPC, retrieved from the internet Apr. 6, 2021: https://tlscientific.com/products/dphpc-4me-16-0-pc-1-2-diphytanoyl-sn-glycero-3-phosphatidylcholine(Year: 2021).
Varghese, D., et al., "advances in tissue engineering: Cell printing", J. Thorac Cardiovasc Surg. 2005; 129: 470-2The Journal of Thoracic and Cardiovascular Survery, Feb. 2005, 470-472.
Office Action for U.S. Appl. No. 16/081,305 "Phase Transfer Of A Cargo Laden Scaffold" dated Apr. 9, 2021.
Sotiropoulou, P.A., et at., "Characterization of the Optimal Culture Conditions for Clinical Scale Production of Human Mesenchymal Stem Cells", Stem Cells 2006: 24:462-471.
Office Action for U.S. Appl. No. 16/081,301 "3D Printing Of A Cellularised Scaffold" dated Jul. 6, 2021.

(56) References Cited

OTHER PUBLICATIONS

Drepper, Thomas, et al., "Lights on and action! Controlling microbial gene expression by light", App. Microbiol. Biotechnol (2011) 90: 23-40.
Yamaguchi, S., et al., "Light-activated gene expression from site-specific caged DNA with a biotinylated photolabile protection group", Chem. Commun., 2010, 46, 2244-2246.
Final Office Action for U.S. Appl. No. 16/081,305 " Phase Transfer Of A Cargo Laden Scaffold" dated Nov. 8, 2021.
Gazda, L.S., et al., "Encapsulation of Porcine Islets Permits Extended Culture Time and Insulin Independence in Spontaneously Diabetic BB Rats", Cell transplantation, vol. 16, pp. 609-620 (2007).
Final Office Action for U.S. Appl. No. 16/081,301 "3D Printing Of A Cellularised Scaffold" dated Jan. 25, 2022.
Notice of Allowance for U.S. Appl. No. 16/081,305 "Phase Transfer of a Cargo Laden Scaffold", dated: Sep. 16, 2022.
Rodova, M. et al., "CMV promoter is repressed by p53 and activated by JNK pathway", Plasmid, 2013, vol. 69, No. 3, p. 223-230.

* cited by examiner

5'-GAAT AA ACGAC CAC A AGGG C AG-3'   SEQ ID NO: 1

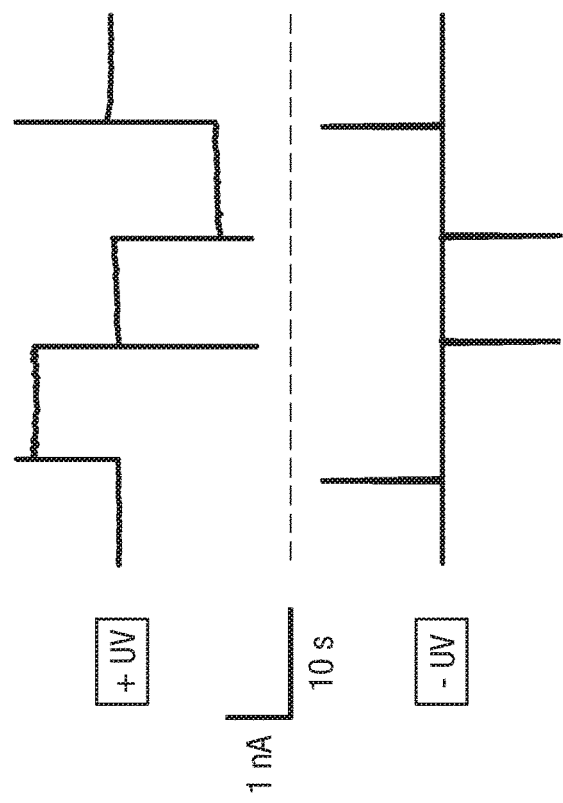
Fig. 10B
+ UV
− UV
1 nA | 10 s
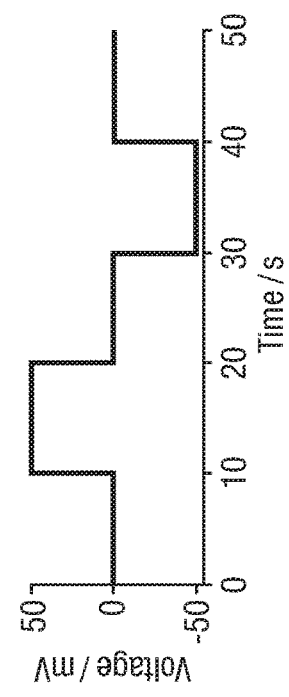
Fig. 10C
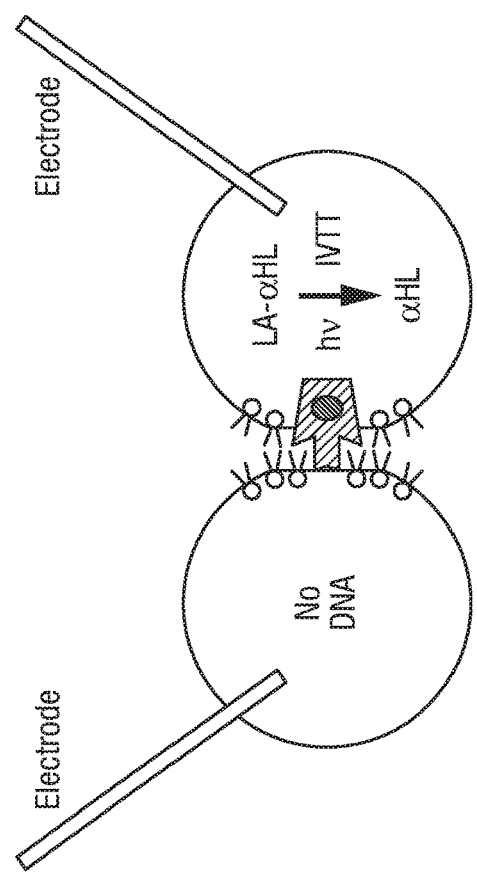
Fig. 10A
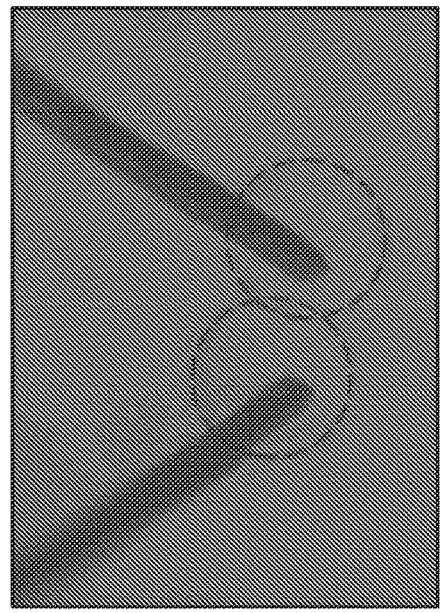

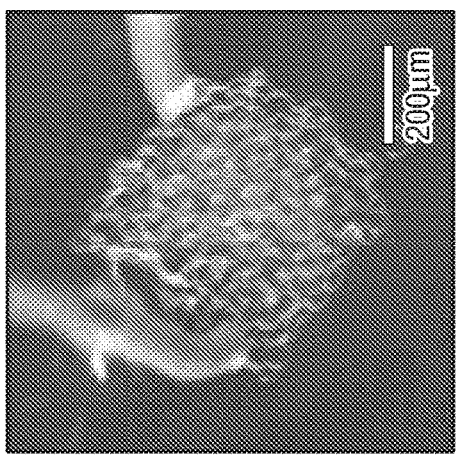
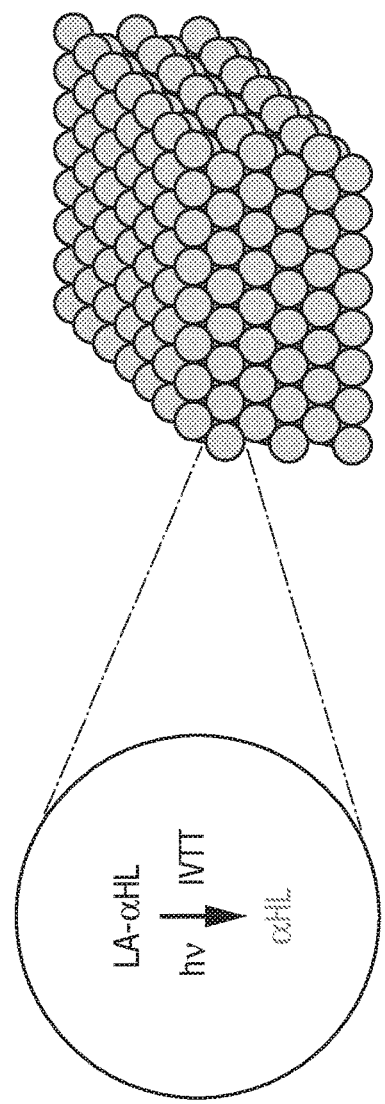
Fig. 14A
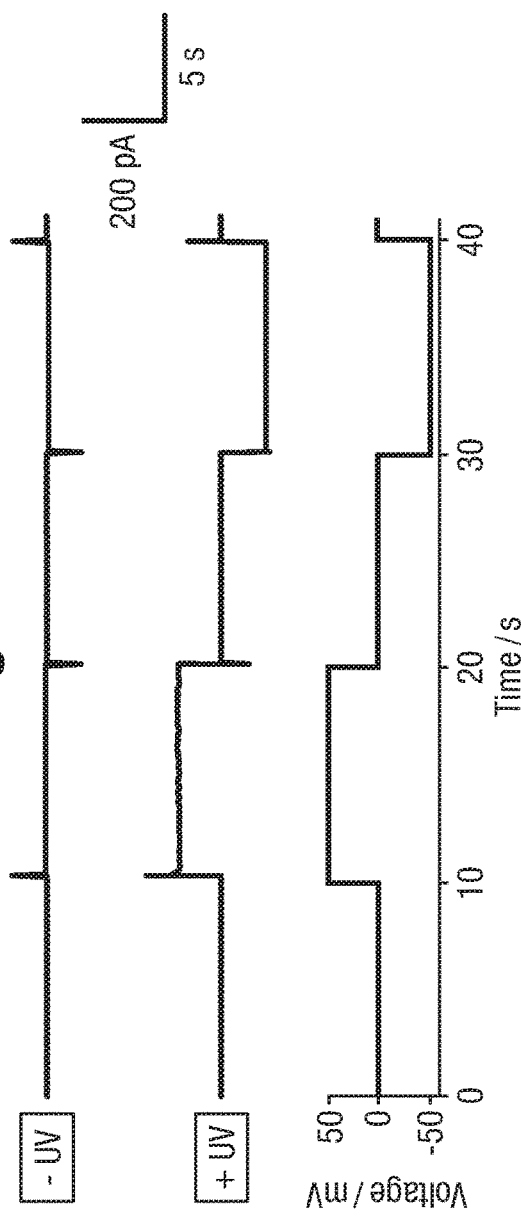
Fig. 14B

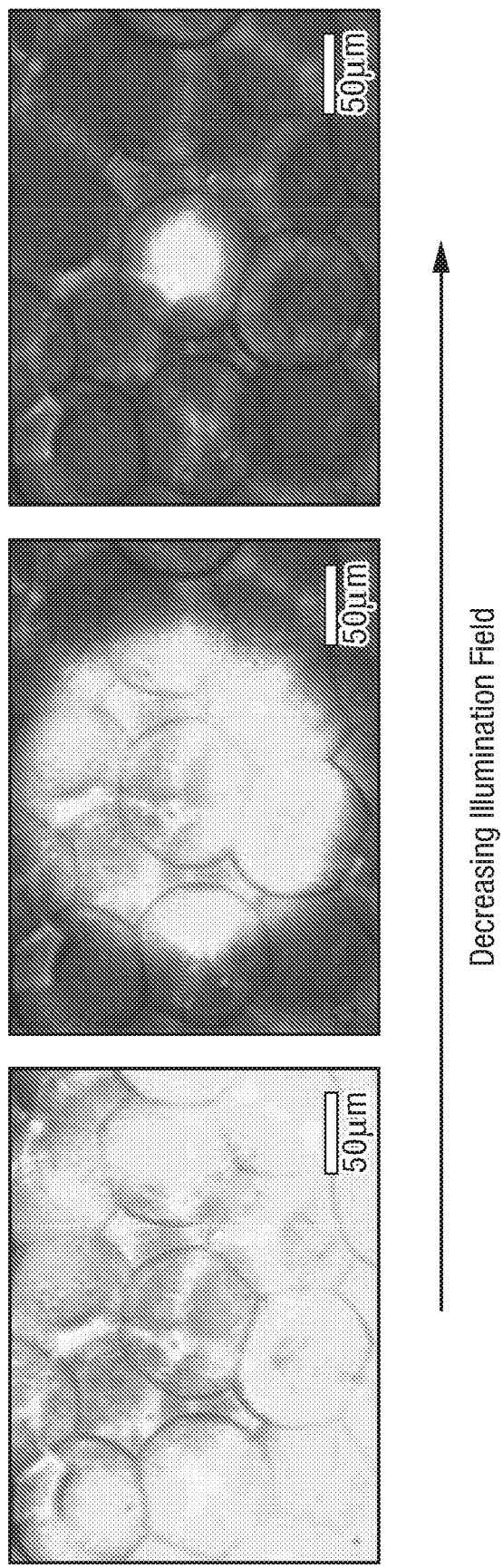

▨ UV-activated LA-αHL droplets
☐ Non-activated LA-αHL droplets

Fig. 20A
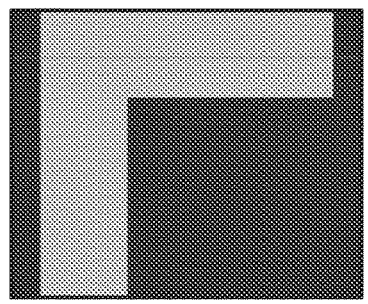 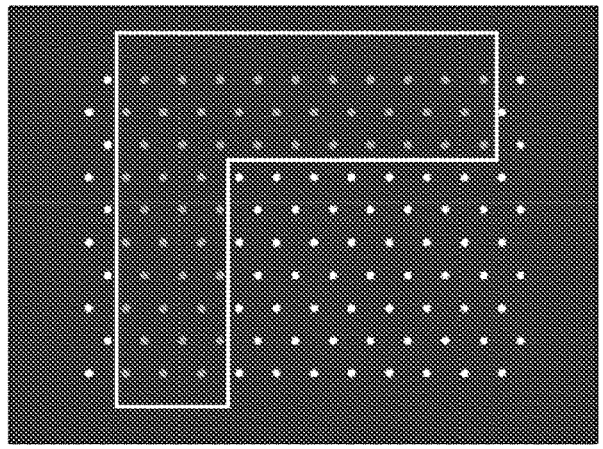
Channel (map A)
Fig. 20B
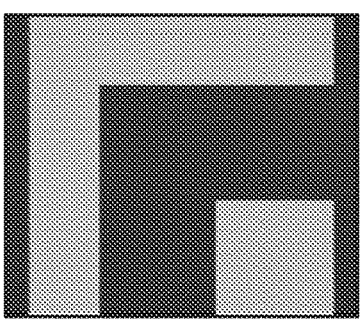 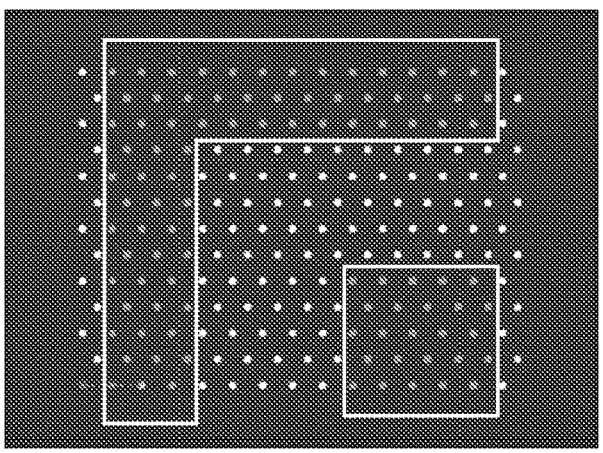
Outside of channel (map B)
Fig. 20C
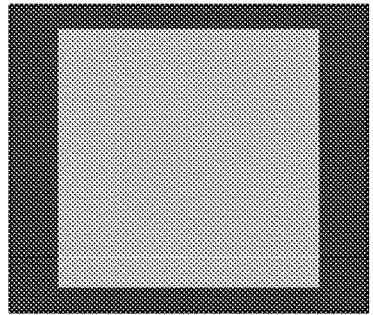 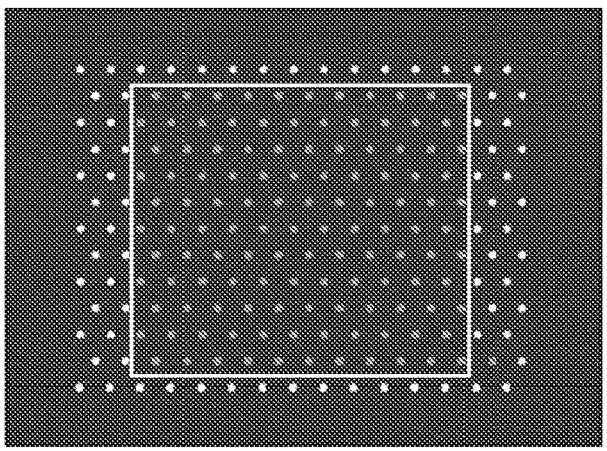
Top of network (map C)

PROMOTERS AND COMPOSITIONS

FUNDING STATEMENT

The work leading to this invention has received funding from the European Research Council under the European Union's Seventh Framework Programme (FP7/2007-2013)/ERC grant agreement no: 294443.

This application is the U.S. National Stage of International Application No. PCT/GB2017/050538, filed Feb. 28, 2017, which designates the U.S., published in English, and claims priority under 35 U.S.C. § 119 or 365 (c) to GB Application No. 1603591.7, filed Mar. 1, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 47761011001SEQUENCELISTING.txt; created Aug. 28, 2018, 4 KB in size.

FIELD OF INVENTION

The present invention relates to activatable promoters, as well as expression systems, vectors, delivery systems, reaction vessels, aqueous objects and compositions comprising said activatable promoters. The invention also provides compositions comprising assemblies and networks of aqueous objects comprising said activatable promoters. The invention additionally provides methods of expressing a transcript and methods of expressing a polypeptide using the activatable promoters of the invention. The invention further provides phospholipid mixtures, as well as aqueous objects and compositions comprising said phospholipid mixtures.

BACKGROUND OF THE INVENTION

Inducible transcription and/or translation systems offer significant versatility in the control of the production of a wide range of biological molecules from regulatory RNAs to proteins and peptides.

Many types of inducible transcription systems have been developed for in vivo and in vitro use.

Cell-free transcription and/or translation systems have been used widely in synthetic biology to create systems that can express functional proteins in a minimal cell-like environment (1-3). These systems have been used for in vitro selection and evolution of proteins (4-7) and control of mammalian (8) and bacterial cells (9). Previous research has been performed e.g. by encapsulating cell-free expression systems in a single lipid-bilayer-bounded compartment, a synthetic cell.

Light activated transcription and/or translation offers a high degree of flexibility and control. Such systems have been achieved previously, however these systems either do not fully repress transcription in the off state (12) or they cannot readily be encapsulated inside certain types of synthetic cells (13, 14).

Thus there is an ongoing requirement for improved inducible transcription and/or translation systems which offer more stringent regulation as between the activated and repressed state. There is also an ongoing requirement for improved systems and structures useful in the expression of biological molecules, particularly in the context of synthetic biological systems.

SUMMARY OF THE INVENTION

The invention provides activatable promoters, as well as expression systems, vectors, delivery systems, reaction vessels, aqueous objects and compositions comprising said activatable promoters. The invention also provides compositions comprising assemblies and networks of aqueous objects comprising said activatable promoters. The invention additionally provides methods of expressing a transcript and methods of expressing a polypeptide using the activatable promoters of the invention. The invention further provides phospholipid mixtures, as well as aqueous objects and compositions comprising said phospholipid mixtures.

Thus the invention provides an activatable promoter comprising a nucleotide promoter sequence and one or more transcription inhibition moieties coupled to one or more components of the activatable promoter, wherein the nucleotide promoter sequence is configured to be activated when the one or more transcription inhibition moieties are uncoupled from the activatable promoter.

In any activatable promoter of the invention the one or more components of the activatable promoter may be components of a nucleotide. The one or more components of a nucleotide may be one or more nucleotide bases or one or more nucleotide base analogues. The one or more components of a nucleotide may be one or more nucleotide sugar groups, or more nucleotide phosphate groups.

In any activatable promoter of the invention the one or more transcription inhibition moieties may be coupled to the one or more components of the activatable promoter via one or more cleavable moieties. The one or more cleavable moieties are preferably photocleavable moieties. The one or more photocleavable moieties may be a moiety that may be cleaved upon contact with electromagnetic radiation, optionally wherein the electromagnetic radiation is infra red (IR), preferably wherein the electromagnetic radiation is ultra violet (UV). The one or more cleavable moieties may be photocleavable moieties comprising 2-nitrobenzyl.

In any activatable promoter of the invention comprising one or more cleavable moieties, the one or more cleavable moieties may further comprises a linker and wherein the one or more transcription inhibition moieties and the one or more cleavable moieties are coupled to the one or more components of the activatable promoter via the linker.

The linker may be a diamine linker. The diamine linker may be an alkyl-diamine linker selected from linkers of formula —N(H)(CH$_2$)$_n$N(H)—, wherein n is from 1 to 20, optionally from 1 to 12, preferably from 1 to 8. The diamine linker may be 1,6-diaminohexane.

In preferred embodiments the one or more components of the activatable promoter are one or more nucleotide bases or nucleotide base analogues and the one or more cleavable moieties further comprises a linker, as defined above.

The one or more nucleotide bases may be purine bases. The one or more nucleotide bases may be adenine and/or guanine. In any such purine bases the linker may be bonded to the purine ring. The linker may be bonded to the purine ring at the 8 position.

The one or more nucleotide bases may be pyrimidine bases. The one or more nucleotide bases may be thymine and/or cytosine and/or uracil. In any such pyrimidine bases the linker may be bonded to the pyrimidine ring. The linker may be bonded to the pyrimidine ring at the 5 position. In any activatable promoter of the invention the one or more transcription inhibition moieties may comprises a small molecule:protein complex and wherein the small molecule of the complex is coupled to any one or more of the cleavable moieties defined herein. The small molecule: protein complex may be a biotin:streptavidin complex and wherein the biotin moiety of the complex is coupled to any one or more of the cleavable moieties defined herein.

In any of the activatable promoters of the invention, the one or more transcription inhibition moieties may be coupled to one or more components of the nucleotide promoter sequence.

In one embodiment the activatable promoter is an activatable promoter comprising a nucleotide promoter sequence and one or more transcription inhibition moieties coupled to one or more components of the activatable promoter, wherein the nucleotide promoter sequence is configured to be activated when the one or more transcription inhibition moieties are uncoupled from the activatable promoter; wherein the one or more components of the activatable promoter are one or more nucleotide bases; wherein the one or more transcription inhibition moieties are coupled to the one or more components of the activatable promoter via one or more photocleavable moieties comprising 2-nitrobenzyl; wherein the one or more photocleavable moieties further comprises a linker and wherein the one or more transcription inhibition moieties and the one or more cleavable moieties are coupled to the nucleotide bases of the activatable promoter via the linker; wherein the the linker is an alkyl-diamine linker selected from linkers of formula —N(H)(CH$_2$)$_n$N(H)— and wherein n is from 1 to 8, optionally wherein the diamine linker is 1,6-diaminohexane; wherein the one or more nucleotide bases are thymine and the linker is bonded to the pyrimidine ring at the 5 position; and wherein the one or more transcription inhibition moieties comprises a biotin:streptavidin complex and wherein the biotin moiety of the complex is coupled to the one or more photocleavable moieties.

The invention also provides an expression system comprising any of the activatable promoters of the invention as defined or described herein operably linked to an open reading frame or to a gene. The open reading frame or gene may encode a peptide, oligopeptide, polypeptide or protein. The open reading frame or gene may encode a membrane protein; for example a pump, a channel, a pore, a receptor protein, a transporter protein, or a protein which effects cell recognition or a cell-to-cell interaction. The membrane protein may be an α-hemolysin (αHL) pore protein. The open reading frame or gene may encode a non-translatable RNA, such as an siRNA or miRNA.

Any of the expression systems of the invention may be operably configured for use with bacteriophage or bacteriophage-related transcription components. For example, the promoter may be a bacteriophage promoter or a bacteriophage-related promoter. The nucleotide promoter sequences may comprise a T7 promoter.

Any of the expression systems of the invention may be operably configured for use with prokaryotic transcription components, for example bacterial transcription components.

Any of the expression systems of the invention may be operably configured for use with eukaryotic transcription components, optionally insect (e.g. baculovirus) or mammalian transcription components.

Any of the expression systems of the invention may further comprise one or more additional transcriptional elements, for example an enhancer.

The invention also provides a vector comprising any of the expression systems of the invention as defined or described herein.

The vector may be a linear double-stranded DNA molecule or it may be a continuous (e.g. circular) double-stranded DNA molecule.

The vector may be a viral vector, optionally a retrovirus, lentivirus, adenovirus, adeno-associated virus or herpes simplex virus vector.

The invention also provides a delivery system comprising any of the vectors of the invention as defined or described herein. Such a delivery system may comprise a yeast system, a lipofection system, a microinjection system, a biolistic system, virosomes, liposomes, immunoliposomes, polycations, lipid:nucleic acid conjugates or artificial virions.

A delivery system may be a viral delivery system, wherein the system comprises any of the viral vectors of the invention as defined or described herein.

The invention also provides reaction vessels comprising an aqueous medium and any of the expression systems or vectors of the invention as defined or described herein; wherein the aqueous medium comprises transcription reagents; and wherein the reaction vessel is configured to receive an uncoupling agent, the agent being capable of uncoupling the one or more transcription inhibition moieties from the one or more components of the activatable promoter of the expression system or vector, whereupon a transcript may be expressed following uncoupling.

A reaction vessel as defined herein is any vessel which contains, carries or harbours an activatable promoter of the invention, e.g. via an expression system or vector of the invention as defined or described herein.

A reaction vessel may be any suitable structure, as defined or described herein, for expressing a transcript. The reaction vessel may be, for example, any suitable test tube or well of a microtitre plate. The reaction vessel may be, for example, any suitable area of a substrate. The reaction vessel may be, for example, an area which is one of a plurality of areas of a substrate comprising an array. The reaction vessel may be any suitable cell of a microfluidic structure. The reaction vessel may be sealed or sealable. The reaction vessel may comprise one or more access channels for the introduction of reagents. The reaction vessel may be a biological cell, or a synthetic cell. The reaction vessel may be an aqueous object comprising an aqueous droplet or a hydrogel object. The reaction vessel may be any such aqueous droplet or a hydrogel object as defined or described herein.

With regard to a reaction vessel which is an aqueous object, such as an aqueous droplet or a hydrogel object as defined or described herein, the aqueous object may comprise an outer layer of amphipathic molecules on at least part of the surface of the aqueous droplet or hydrogel object. The outer layer of amphipathic molecules may encapsulate the aqueous droplet or hydrogel object.

Any reaction vessel which may comprise an outer layer of amphipathic molecules may comprise amphipathic molecules which are lipid molecules. The amphipathic molecules may comprise phospholipid molecules. The phospholipid molecules may comprise non-PEGylated phospholipids and PEGylated phospholipids. Where phospholipid molecules comprise non-PEGylated phospholipids and PEGylated phospholipids, from 2.5 to 15 mol % of the phospholipids may be PEGylated phospholipids. Alternatively, from 7.5 to 15 mol % of the phospholipids may be PEGylated phospholipids. Alternatively, from 5 to 15 mol % of the phospholipids are PEGylated phospholipids. Preferably from 10 to 15 mol % of the phospholipids may be PEGylated phospholipids.

Any reaction vessel which may comprise an outer layer of amphipathic molecules comprising PEGylated phospholipids may comprise phospholipids having a PEG group which has a molecular weight of from 1500 to 5000 g/mol, optionally from 1800 to 2200 g/mol.

In any reaction vessel which may comprise an outer layer of amphipathic molecules comprising non-PEGylated phospholipid molecules and PEGylated phospholipid molecules, the non-PEGylated phospholipid molecules may be glycerophospholipids and/or the PEGylated phospholipids may be glycerophospholipids.

In any reaction vessel which may comprise an outer layer of amphipathic molecules comprising non-PEGylated glycerophospholipids, the non-PEGylated phospholipids may be phospholipids of formula (I):

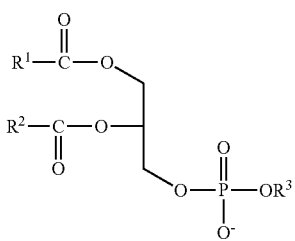

(I)

wherein:
R$^1$ and R$^2$, which are the same or different, are selected from C$_{10}$-C$_{25}$ alkyl groups and C$_{10}$-C$_{25}$ alkenyl groups;
R$^3$ is absent such that OR$_3$ is O$^-$, or R$^3$ is present and is H, CH$_2$CH$_2$N(R$_4$)$_3^+$, a sugar group, or an amino acid group; and
each R$^4$, which is the same or different, is independently selected from H and unsubstituted C$_1$-C$_4$ alkyl.

In any reaction vessel which may comprise an outer layer of amphipathic molecules comprising PEGylated glycerophospholipids the PEGylated phospholipids may be phospholipids of the following formula (II)

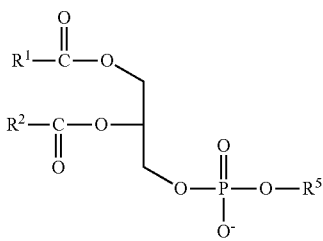

(II)

wherein:
R$^1$ and R$^2$ are as defined above for the phospholipids of formula (I), and R$^5$ is a group which comprises poly(ethylene glycol). R$^5$ may be —CH$_2$CH$_2$NHC(O)—(OCH$_2$CH$_2$)$_q$OCH$_3$, —CH$_2$CH$_2$NHC(O)(CH$_2$)$_3$C(O)—(OCH$_2$CH$_2$)$_q$OCH$_3$, —CH$_2$CH$_2$NHC(O)—(OCH$_2$CH$_2$)$_q$OH, or —CH$_2$CH$_2$NHC(O)(CH$_2$)$_3$C(O)—(OCH$_2$CH$_2$)$_q$OH, wherein q is an integer from 5 to 10,000.

In any reaction vessel which may comprise an outer layer of amphipathic molecules comprising non-PEGylated phospholipids which are glycerophospholipids, the non-PEGylated phospholipids may comprise DPhPC.

In any reaction vessel which may comprise an outer layer of amphipathic molecules comprising PEGylated phospholipids which are glycerophospholipids, the PEGylated phospholipids may comprise DPPE-mPEG2000. The PEGylated phospholipids may comprise from 5 to 15 mol % of DPPE-mPEG2000.

In any reaction vessel which may comprise an outer layer of amphipathic molecules comprising PEGylated phospholipids which are glycerophospholipids and non-PEGylated phospholipids which are glycerophospholipids, the non-PEGylated phospholipids may comprise DPhPC and the PEGylated phospholipids may comprise DPPE-mPEG2000. In such cases the phospholipids may comprise, for example, from 2.5 to 15 mol % of DPPE-mPEG2000, preferably from 5 to 15 mol % of DPPE-mPEG2000.

In any reaction vessel defined or described herein, the aqueous medium may comprise an in vitro transcription system.

In any reaction vessel defined or described herein, the aqueous medium may comprise an in vitro transcription system and an in vitro translation system.

The invention further provides a composition comprising one or more or any of the reaction vessels defined or described herein and a hydrophobic medium, wherein the one or more reaction vessels are disposed in the hydrophobic medium. In any such composition the hydrophobic medium may comprise an oil. The hydrophobic medium may comprise an oil comprising silicone oil, a hydrocarbon, or a fluorocarbon, or a mixture of two or more thereof.

The hydrophobic medium may comprise a mixture of a hydrocarbon and silicone oil. In such a composition, the ratio of hydrocarbon:silicone oil may be, for example, from 50:50 to 20:80 by volume, or from 50:50 to 80:20 by volume, preferably in a ratio of from 50:50 to 40:60 by volume.

In any such composition comprising a hydrocarbon, the hydrocarbon may be a C10-C20 alkane, preferably a hexadecane.

In any such composition, the one or more reaction vessels may comprise a plurality of reaction vessels forming an assembly. In any such composition, the one or more reaction vessels in the assembly may contact at least one other reaction vessel in the assembly.

In any such composition comprising an outer layer of amphipathic molecules on at least part of the surface of the reaction vessel, an interface may be formed between the contacting reaction vessels. In any such composition, the interface may comprises a layer of amphipathic molecules, preferably a bilayer of amphipathic molecules. Alternatively, the interface may not comprise a layer of amphipathic molecules.

In any such composition, a plurality of reaction vessels may be connected so as to form a network of reaction vessels. In any such composition, at least two reaction vessels may be connected via an interface comprising a bilayer of amphipathic molecules, and wherein the aqueous medium of said at least two reaction vessels are in fluid communication via a pore within the bilayer. The pore may be comprised of α-hemolysin (αHL).

The invention also provides an electrochemical circuit comprising any of the reaction vessel-containing compositions defined or described herein.

The invention also provides a method of expressing a transcript, the method comprising: providing any of the reaction vessels or compositions defined or described herein and providing an uncoupling agent to the vessel, the agent being capable of uncoupling the one or more transcription inhibition moieties from the one or more components of the activatable promoter; whereupon the transcript is expressed following uncoupling.

The invention also provides a method of expressing a transcript, the method comprising: contacting any of the activatable promoters defined or described herein with an uncoupling agent, the agent being capable of uncoupling the one or more transcription inhibition moieties from the one or more components of the activatable promoter; whereupon the transcript is expressed following uncoupling.

In any such method, the activatable promoter may be comprised in any of the expression systems or vectors defined or described herein.

In any such method, the cleavable moiety of the activatable promoter may be a photocleavable moiety, and wherein the uncoupling agent may be electromagnetic radiation, optionally wherein the electromagnetic radiation is infra red (IR), preferably wherein the electromagnetic radiation is ultra violet (UV).

In any such method comprising a cleavable moiety of the activatable promoter, the cleavable moiety may comprise a linker. A cleavable moiety may be a photocleavable moiety. The photocleavable moiety may comprise 2-nitrobenzyl. The photocleavable moiety may comprise a linker comprising 2-nitrobenzyl.

The invention also provides a method of producing a peptide, oligopeptide, polypeptide or protein, the method comprising expressing a transcript by any of the methods of expressing a transcript as defined or described herein, and further comprising translating the transcript into a peptide, oligopeptide, polypeptide or protein.

In any such method of producing a polypeptide, the reaction vessel may be any suitable reaction vessel as defined or described herein, and in such cases the aqueous medium may comprise an in vitro transcription and translation system.

The invention also provides a phospholipid mixture, wherein the mixture comprises phospholipids comprising non-PEGylated phospholipids and PEGylated phospholipids.

Any such phospholipid mixture may be a mixture wherein from 2.5 to 15 mol % of the phospholipids are PEGylated phospholipids.

In any such mixture, from 5 to 15 mol % of the phospholipids may be PEGylated phospholipids or from 7.5 to 15 mol % of the phospholipids may be PEGylated phospholipids, preferably from 10 to 15 mol % of the phospholipids may be PEGylated phospholipids.

In any such mixture, the PEGylated phospholipids may comprise a PEG group which has a molecular weight of from 1500 to 5000 g/mol. optionally from 1800 to 2200 g/mol.

In any such mixture, the non-PEGylated phospholipids may be glycerophospholipids and/or the PEGylated phospholipids may be glycerophospholipids.

In any such mixture comprising non-PEGylated glycerophospholipids the non-PEGylated glycerophospholipids are glycerophospholipids of formula (I):

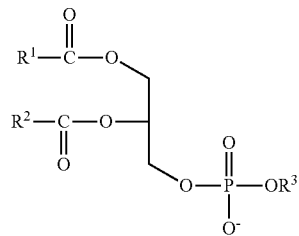

wherein:
$R^1$ and $R^2$, which are the same or different, are selected from $C_{10}$-$C_{25}$ alkyl groups and $C_{10}$-$C_{25}$ alkenyl groups;
$R^3$ is absent such that $OR_3$ is $O^-$, or $R_3$ is present and is H, $CH_2CH_2N(R_4)_3^+$, a sugar group, or an amino acid group; and
each $R^4$, which is the same or different, is independently selected from H and unsubstituted $C_1$-$C_4$ alkyl.

In any such mixture comprising PEGylated glycerophospholipids, the glycerophospholipids are glycerophospholipids of the following formula (II)

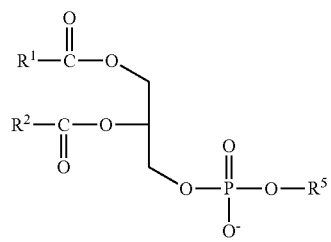

wherein:
$R^1$ and $R^2$ are as defined above for the phospholipids of formula (I), and $R^5$ is a group which comprises poly (ethylene glycol). $R^5$ may be —$CH_2CH_2NHC(O)$—$(OCH_2CH_2)_qOCH_3$, —$CH_2CH_2NHC(O)(CH_2)_3C(O)$—$(OCH_2CH_2)_qOCH_3$, —$CH_2CH_2NHC(O)$—$(OCH_2CH_2)_qOH$, or —$CH_2CH_2NHC(O)(CH_2)_3C(O)$—$(OCH_2CH_2)qOH$, wherein q is an integer from 5 to 10,000.

In any such mixture comprising non-PEGylated phospholipids which are glycerophospholipids, the non-PEGylated glycerophospholipids may comprise DPhPC.

In any such mixture comprising PEGylated phospholipids which are glycerophospholipids, the PEGylated glycerophospholipids may comprise DPPE-mPEG2000. The PEGylated glycerophospholipids may comprise from 2.5 to 15 mol % of DPPE-mPEG2000, preferably from 5 to 15 mol % of DPPE-mPEG2000.

In any such mixture comprising PEGylated phospholipids which are glycerophospholipids and non-PEGylated phospholipids which are glycerophospholipids, the non-PEGylated phospholipids may comprise DPhPC and the PEGylated phospholipids may comprise DPPE-mPEG2000. In such cases the phospholipids may comprise, for example, from 5 to 15 mol % of DPPE-mPEG2000.

The invention also provides an aqueous object comprising an aqueous medium and further comprising an outer layer of a mixture of phospholipid molecules on at least part of the surface of the aqueous object, wherein the mixture of phospholipid molecules is any mixture as defined or described herein. Such an aqueous object may not contain, carry or harbour an activatable promoter as defined or described herein, e.g. may not contain, carry or harbour an expression system or a vector as defined or described herein.

In such an aqueous object, the outer layer of phospholipid molecules may encapsulate the aqueous object. In such an aqueous object, the object may be any aqueous droplet as defined or described herein. In such an aqueous object, the object may be any hydrogel object defined or described herein.

Any such aqueous object may be comprised in a composition comprising one or more of any such aqueous object and a hydrophobic medium, wherein the one or more aqueous objects are disposed in the hydrophobic medium. In such compositions the hydrophobic medium may comprise an oil. The hydrophobic medium may comprise an oil comprising silicone oil, a hydrocarbon, or a fluorocarbon, or a mixture of two or more thereof.

The hydrophobic medium may comprise a mixture of a hydrocarbon and silicone oil. In such a composition, the ratio of hydrocarbon:silicone oil may be, for example, from 50:50 to 20:80 by volume, or from 50:50 to 80:20 by volume, preferably in a ratio of from 50:50 to 40:60 by volume.

In any such composition comprising a hydrocarbon, the hydrocarbon may be a $C_{10}$-$C_{20}$ alkane, preferably a hexadecane.

In any such composition, the one or more aqueous objects may comprise a plurality of aqueous objects forming an assembly. In any such composition, the one or more aqueous objects in the assembly may contact at least one other aqueous object in the assembly.

In such a composition comprising an outer layer of amphipathic molecules on at least part of the surface of the aqueous object, an interface may be formed between the contacting aqueous objects. In any such composition, the interface may comprises a layer of amphipathic molecules, preferably a bilayer of amphipathic molecules. Alternatively, the interface may not comprise a layer of amphipathic molecules.

In any such composition, a plurality of such aqueous objects may be connected so as to form a network of aqueous objects. In any such composition, at least two such aqueous objects may be connected via an interface comprising a bilayer of amphipathic molecules, and wherein the aqueous medium of said at least two aqueous objects are in fluid communication via a pore within the bilayer. The pore may be comprised of α-hemolysin (αHL).

The invention also provides an electrochemical circuit comprising any such composition.

DESCRIPTION OF THE FIGURES

FIG. 10 shows light-activated electrical signal between synthetic cells. (A) Schematic of the synthetic cell pair. One cell contains LA-αHL DNA, the other contains no DNA. Both droplets have electrodes inserted within them to apply a potential and measure the ionic current. Below is an image of the experimental setup. (B) A current is detected only following the expression of αHL following light-activation. (C) Voltage protocol used in B.

FIG. 14 shows recording of electrical communication in 3D-printed synthetic tissues mediated by LA-αHL DNA. (A) Schematic of 3D-printed synthetic tissue containing LA-αHL DNA, which expresses the αHL membrane pore upon light activation. (B) Electrical recordings from a 3D-printed network demonstrates that a current through the synthetic tissues is only detected upon light activation. The voltage protocol used to detect αHL insertion into bilayer is also shown.

FIG. 17 shows restricted microscope illumination of a synthetic tissue. A fluorescence microscope with a field diaphragm (see methods) was used to illuminate a large area (illumination field setting 3), small area (illumination field setting 2) and a single droplet (illumination field setting 1) within a synthetic tissue, where all droplets contain mVenus protein.

FIG. 20 shows maps for the LA-Venus 3D-printed pathway experiment and LA-αHL patterned 3D channel experiment. (A) Channel (map A): Length of 10 droplets and a width of 3 droplets, which is enclosed by the white lines. (B) Outside of channel (map B): A width of 3 droplets and a length of 13 droplets, along with a small square of 5×5 droplets, both of which are enclosed by white lines. A gap of 5 droplets was left between both structures, for where the channel structure was printed. (C) Top of network (map C): An 11×11 droplet square, which is enclosed by white lines. The gap around the outside was to ensure these droplets only landed on the top of the structure.

DETAILED DESCRIPTION OF THE INVENTION

Figure 1A:
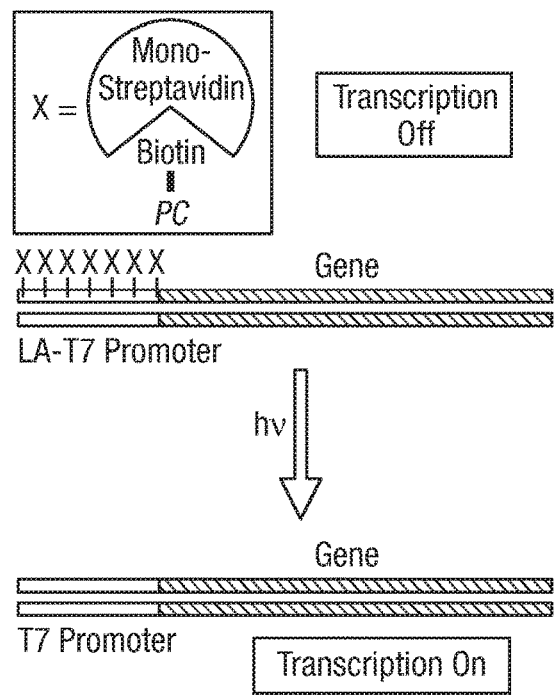
FIG. 1 shows construction and evaluation of a light-activated promoter. (A) T7 RNA polymerase is blocked from binding to the LA-T7 promoter due to the presence of multiple monovalent streptavidin, bound to the DNA through a biotinylated photocleavable linker. Following UV light cleavage of the linker, T7 RNA polymerase is able to transcribe the downstream gene. (B) LA-T7 promoter sequence. Light-grey-coloured Ts (thymines) are replaced with amino-C6-dT modifications and the primary amines of the nucleobase coupled to the PC-Biotin group. (C) Light-activated DNA encoding for mVenus is only expressed upon UV irradiation. There is no significant difference between expression from the LA-DNA (+UV) compared to expression from the amine-only DNA construct. At one hour, the labelling of the lines from lowest to highest fluorescence intensity is as follows: no DNA; LA-DNA (-UV); LA-DNA (+UV); and Amino DNA (+UV).

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a phospholipid" includes two or more instances or versions of such phospholipids, or reference to "a moiety" includes two or more such moieties, or reference to "a nucleotide" includes two or more such nucleotides and the like.

Any numerical parameters as defined herein may be expressed as approximate numerical values, wherein the said numerical value may be plus or minus 10% of the said numerical value unless the context clearly dictates otherwise.

All publications, patents and patent applications cited herein, whether supra or infra, are hereby incorporated by reference in their entirety.

The invention relates to an activatable promoter. The activatable promoter of the invention is also referred to herein as a promoter, unless the context clearly dictates otherwise. The promoter comprises one or more transcription inhibition moieties coupled to one or more components of the promoter. The one or more transcription inhibition moieties inhibit transcription from the promoter. Therefore when the one or more transcription inhibition moieties are uncoupled from the promoter, transcription can be initiated from the promoter. The initiation of transcription may occur promptly after the uncoupling if the required transcriptional machinery is present. Alternatively, if one or more components of the transcriptional machinery are not present when the one or more transcription inhibition moieties are uncoupled, then transcription may be initiated at a later time once the further transcriptional components are provided. For example, the promoter may comprise one or more inducible elements and may thus be an inducible promoter, and the promoter may not have been induced when the one or more transcription inhibition moieties are uncoupled.

The promoter can be any type of promoter. The promoter may be provided in isolated or purified form. The promoter comprises polynucleotide sequences, typically DNA, which initiates and regulates transcription. The promoter can be an inducible promoter where transcription is induced by, for example, an analyte, cofactor, regulatory protein, a repressible promoter where transcription is repressed by, for example, an analyte, cofactor, regulatory protein, or a constitutive promoter.

As defined herein, an "activatable promoter" of the invention, or simply "promoter" of the invention refers to a stretch of polynucleotide sequences which comprises nucleotide promoter sequences that promote transcription. Such nucleotide promoter sequences may for example comprise one or more binding sites for one or more proteins which are required for transcription. Thus, the activatable promoter of the invention can comprise polynucleotide sequences in addition to the nucleotide promoter sequences that promote transcription. Alternatively, the activatable promoter of the invention can consist of nucleotide promoter sequences that promote transcription. Consequently, transcription inhibition moieties may be coupled directly to components of nucleotide promoter sequences which comprise one or more binding sites for one or more proteins which are required for transcription. Alternatively, transcription inhibition moieties may be coupled to components of nucleotide sequences which are outside of a binding site for a protein which is required for transcription but nevertheless such coupling will inhibit transcription e.g. by sterically interfering with the binding of one or more proteins which are required for transcription. The activatable promoter of the invention can be a functional segment of a promoter.

The promoter of the invention can comprise or consist of promoter sequences derived from a prokaryote or eukaryote or other organism. For example, the promoter may comprise or consist of promoter sequences from, or derived from, bacteria, archaea, fungi e.g. yeast, a virus e.g. a bacteriophage, an animal e.g. a mammal, or a plant, or from related systems. The promoter of the invention can comprise or consist of a T7, trc, lac, ara or promoter. T7 promoter sequences, e.g. a T7 promoter, is preferable. The promoter can, for example, comprise or consist of promoter sequences from cytomegalovirus (CMV) immediate early, herpes simplex virus (HSV) thymidine kinase, early and late SV40, long terminal repeats (LTRs) from retrovirus, or mouse metallothionein-I. The promoter can comprise or consist of pol I, pol II or pol II promoter sequences. Examples of suitable pol III promoter sequences include, but are not limited to, U6 and H1 promoters. Examples of suitable pol II promoter sequences include, but are not limited to, the retroviral Rous sarcoma virus (RSV) LTR promoter, the cytomegalovirus (CMV) promoter [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter.

A polynucleotide, such as a nucleic acid, is a polymer comprising two or more nucleotides. The nucleotides can be naturally occurring or artificial or analogues thereof. A nucleotide typically contains a nucleobase, a sugar and at least one linking group, such as a phosphate, 2'O-methyl, 2' methoxy-ethyl, phosphoramidate, methylphosphonate or phosphorothioate group. The nucleobase is typically heterocyclic. Nucleobases include, but are not limited to, purines and pyrimidines and more specifically adenine (A), guanine (G), thymine (T), uracil (U) and cytosine (C). Nucleobases also include, but are not limited to, other natural and non-natural bases. The terms "nucleotide base" and "nucleobase" are used interchangeably herein. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate and can be referred to herein as nucleotide phosphates. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides may be selected from AMP, TMP, GMP, UMP, dAMP, dTMP, dGMP or dCMP.

The nucleotides may contain additional modifications. The modifications may be made to the nucleobase to form nucleotide base analogues. The modifications may be chemical or biochemical, or the nucleotide or nucleobase may be derivatized. In particular, modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine). Modified nucleotides also include, but are not limited to 5-pentynyl-2'-deoxy uridine, 5-(3-aminopropyl)-uridine and 1,6-diaminohexyl-N-5-carbamoylmethyl uridine.

The nucleotides in the polynucleotide may be attached to each other in any manner. The nucleotides may be linked by phosphate, 2'O-methyl, 2' methoxy-ethyl, phosphoramidate, methylphosphonate or phosphorothioate linkages. The nucleotides are typically attached by their sugar and phosphate groups as in nucleic acids. The nucleotides may be connected via their nucleobases as in pyrimidine dimers.

The polynucleotide can comprise a nucleic acid, such as deoxyribonucleic acid (DNA) or a ribonucleic acid (RNA). The polynucleotide may comprise any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains. The polynucleotide may comprise single stranded, double stranded or multi-stranded. The polynucleotide may comprise a gene, a gene fragment, an exon, an intron, genomic DNA, DNA-RNA hybrids, messenger RNA (mRNA), cDNA, recombinant polynucleotides, plasmids, vectors, isolated DNA of any sequence, isolated RNA of any sequence, nucleic acid probes, and primers. The polynucleotide sequence may comprise an open reading frame.

Polynucleotides can be synthesised according to methods well known in the art, as described by way of example in Sambrook et al (1989, Molecular Cloning—a laboratory manual; Cold Spring Harbor Press).

The promoter of the invention comprises one or more transcription inhibition moieties coupled to one or more components of the promoter. The one or more components of the promoter may be any of the features of the promoter described herein. For example, the one or more components can be a nucleotide, nucleobase, phosphate or sugar such as those described herein. Preferably the one or more components of the promoter are bases of nucleotides. There is preferably a plurality of promoter components coupled to a plurality of transcription inhibition moieties.

There may be more than one, i.e. a plurality, of components of the promoter which are coupled to the transcription inhibition moieties. For example, there may be from 2 to 500, 2 to 250, 2 to 150, 2 to 50 or 2 to 10. There may be 2, 3, 4, 5, 6, 7, 8, 9 or 10. There may be one component of the promoter coupled to a transcription inhibition moiety.

The one or more transcription inhibition moieties are capable of inhibiting transcription from the promoter. They may decrease or completely prevent transcription. When coupled to one or more components of the promoter, the transcription inhibition moieties inhibit transcription, for example, by preventing one or more components of the transcriptional machinery from binding and/or performing its function. The binding may be directly or indirectly to the promoter or may be directly or indirectly to a region upstream or downstream of the promoter. The transcription inhibition moieties may inhibit transcription by sterically hindering one or more components of the transcriptional machinery. For example, the transcription inhibition moieties may prevent a protein binding to the promoter or a region upstream or downstream of the promoter. Alternatively or additionally, for example, the transcription inhibition moieties may prevent a protein-protein interaction.

There may be more than one, i.e. a plurality, of transcription inhibiting moieties present in the promoter. For example, there may be from 2 to 500, 2 to 250, 2 to 150, 2 to 50 or 2 to 10. There may be 2, 3, 4, 5, 6, 7, 8, 9 or 10. There may be one transcription inhibiting moiety present in the promoter.

If there is a plurality of transcription inhibition moieties, then there may also be a plurality of the components of the promoter coupled to the transcription inhibition moieties. There may be equal numbers of transcription inhibition moieties and components of the promoter coupled to the transcription inhibition moieties.

Any suitable molecule, or complex of molecules, may act as a transcription inhibition moiety. Suitably, a transcription inhibition moiety should readily be coupled to a component of the promoter using standard techniques known to the skilled person. Suitably, a transcription inhibition moiety should be sufficiently large to be able to interfere with one or more components of the transcription machinery so as to inhibit transcription. The moiety may typically comprise a protein or a complex of a protein and small molecule. However, the moiety could for example comprise any suitable molecule or combination of molecules provided that the molecules (or one of said combination) may be coupled to a component of the promoter using standard techniques and that the molecule or combination of molecules may interfere with one or more components of the transcription machinery so as to inhibit transcription. The transcription inhibition moieties preferably comprise a biotin:streptavidin complex. The streptavidin may be monovalent. The biotin is preferably coupled to the one or more components of the promoter. The transcription inhibition moieties may comprise an upconverting nanoparticle (UCNP). The transcription inhibition moieties may comprise digoxigenin (DIG) in complex with a DIG antibody. The transcription inhibition moieties may comprise both a biotin:streptavidin complex and digoxigenin (DIG) in complex with a DIG antibody.

By the one or more transcription inhibition moieties being "coupled" to one or more transcription inhibition moieties, this means the one or more transcription inhibition moieties are attached to the one or more transcription inhibition moieties in some manner. This attachment may be by covalent or non-covalent bonds. The attachment results in inhibition of the promoter. Conversely, when the one or more transcription inhibition moieties are "uncoupled" from the one or more transcription inhibition moieties, this means the one or more transcription inhibition moieties are sufficiently detached from the one or more transcription inhibition moieties so that the inhibition of transcription is reduced or removed.

The promoter being "configured to be activated" when the one or more transcription inhibition moieties are uncoupled from the promoter means that transcription from the promoter can be enhanced, begin or increase, compared to the inhibited state, once the one or more transcription inhibition moieties are uncoupled. Transcription may thus be increased by over 130 fold, for example up to 200 fold. Transcription may increase by, for instance, from 2 to 200 fold, from 10 to 180 fold, from 50 to 150 fold, or from 100 to 150 fold.

The uncoupling can be as a result of cleavage such as photocleavage. Thus the transcription inhibition moieties are preferably coupled to the one or more components of the promoter via one or more cleavable moieties. The one or more cleavable moieties may preferably be photocleavable. There may be more than one, i.e. a plurality, of cleavable moieties present in the activatable promoter. For example, there may be from 2 to 500, 2 to 250, 2 to 150, 2 to 50 or 2 to 10. There may be 2, 3, 4, 5, 6, 7, 8, 9 or 10. There may be one cleavable moiety present in the promoter. If there is a plurality of transcription inhibition moieties, then there may also be a plurality of cleavable moieties. There may be equal numbers of transcription inhibition moieties and cleavable moieties. There can be equal numbers of components of the promoter coupled to the transcription inhibition moieties, transcription inhibition moieties and cleavable moieties.

Cleavage of the cleavable moieties removes or reduces the inhibition of the promoter and therefore transcription can begin or increase from the promoter. Photocleavage occurs upon contacting the photocleavable moiety with or administration of or provision of electromagnetic radiation such as light, e.g. infra red, ultraviolet etc. Thus the term "light-activated DNA promoter" (LA-DNA promoter) refers to a promoter of the invention which comprises any photocleavable moiety.

Any of the activatable promoters defined or described herein may comprise any suitable photocleavable moiety. For example, the photocleavable moiety may comprise a nitroaryl group. The photocleavable moiety may comprise a nitrobenzyl group, preferably a 2-nitrobenzyl. The photocleavable moiety may comprise a 4-methoxyphenacyl group, a 4,5-dimethoxy-2-nitrobenzyl group or a 3,5-dimethoxy-benzoin group such as those described in Stanton-Humphreys et al., 2012; "Wavelength-orthogonal photolysis of neurotransmitters in vitro"; Chem. Commun.; 48; 657-659.

The photocleavable moiety may comprise a C4'-dialkyl-amine-substituted heptamethine cyanine (as described in Gorka et al. 2014; "A Near-IR Uncaging Strategy Based on Cyanine Photochemistry"; Journal of the American Chemical Society; 136; 14153-14159), for example (modified from Gorka et al. 2014):

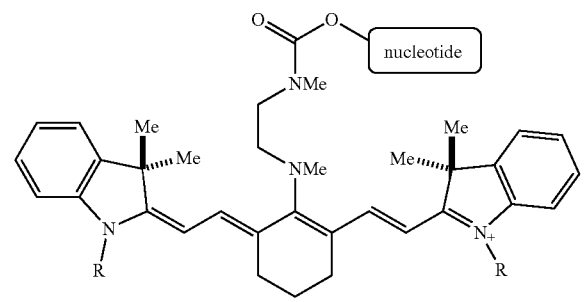

R is n-propyl (—CH$_2$CH$_2$CH$_3$) or —(CH$_2$)$_4$SO$_3^-$. The transcription inhibition moieties may be attached to any suitable group on the C4'-dialkyl-amine-substituted heptamethine cyanine moiety.

The light administration may directly or indirectly result in cleavage. For example, if the photocleavable moieties comprise a nitrobenzyl group and are treated with UV light, the UV light can act on the nitrobenzyl group resulting in cleavage of the photocleavable moieties. Alternatively, the light administration may cause a component which may or may not be part of the photocleavable moieties to release light in the UV-visible light wavelength range. A suitable component is an upconverting nanoparticle (UCNP). The light in the UV-visible light wavelength range can then trigger cleavage of the photocleavable moieties, for example of a nitrobenzyl group. UCNPs take in infrared light to photocleave 2-nitrobenzene.

The wavelength of the electromagnetic radiation will be determined by the moiety being photocleaved and whether or not the moiety is being photocleaved directly or indirectly following electromagnetic radiation administration. The electromagnetic radiation can be in the UV-visible light wavelength range, preferably UV light. The wavelength can be from 10 to 400 nm, 100 to 400 nm, 200 to 400 nm, 300 to 400 nm or 350 to 380 nm. Preferably the wavelength is 365 nm. The light can also be in the near infrared window. The wavelength can be from 650 to 900 nm, 650 to 800 nm, 650 to 750 nm, or 680 to 720 nm.

In any of the activatable promoters defined or described herein the cleavable moieties may further comprise a linker. The linker may couple the one or more transcription inhibition moieties and the one or more cleavable moieties to the one or more components of the promoter. Typically the one or more transcription inhibition moieties will be coupled to a cleavable moiety, the cleavable moiety will further comprise a linker and the linker may be coupled to the one or more components of the promoter, either directly or indirectly. Direct coupling may be for example by bonding the linker to the ring of a purine or pyrimidine base of a nucleotide, as described herein.

The linker may be a diamine linker. The diamine linker may be an alkyl-diamine linker selected from linkers of formula —N(H)(CH$_2$)$_n$N(H)—, wherein n is a positive integer, for instance from 1 to 20 or from 1 to 12, preferably from 1 to 8. The diamine linker is preferably 1,6-diaminohexane (—N(H)(CH$_2$)$_6$N(H)—). For example, when attached to a thymine, the linker and thymine forms a C6-amino-dT or a C6-amino-T. The linker may be an alkylene group —(CH$_2$)$_n$—, wherein n is a positive integer, for instance from 1 to 20 or from 1 to 12, preferably from 1 to 8. The linker may be a —C(H)=C(H)C(O)N(H)(CH$_2$)$_n$N(H)—, wherein n is a positive integer, for instance from 1 to 20 or from 1 to 12, preferably from 1 to 8.

The linker may be formed using a N-Hydroxysulfosuccinimide (NHS) ester such as a biotin NETS-ester. The linker may be formed using isocyanate, maleimide, disulfite, hydrazine or hydrazine.

There may be more than one, i.e. a plurality, of linkers present in the promoter. For example, there may be from 2 to 500, 2 to 250, 2 to 150, 2 to 50 or 2 to 10. There may be 2, 3, 4, 5, 6, 7, 8, 9 or 10. There may be one linker present in the promoter. There are typically the same number of linkers present as transcription inhibition moieties and cleavable moieties. Thus there can be equal numbers of transcription inhibition moieties, cleavable moieties and linkers. There can be equal numbers of components of the promoter coupled to the transcription inhibition moieties, transcription inhibition moieties, cleavable moieties and linkers.

The one or more transcription inhibition moieties coupled to one or more components of the activatable promoter may have the formula COMP-L-PC-X, wherein COMP is the one or more components of the activatable promoter coupled to the one or more transcription inhibition moieties, L is the linker, PC is the one or more cleavable moieties (preferably photocleavable moieties) and X is the one or more transcription inhibition moieties.

Typically the linker is bonded to one of the ring positions in the base. If the base is a purine base, the linker is typically bonded to the 8 position on the purine ring. If the base is a pyrimidine base, the linker is typically bonded to the 5 position on the pyrimidine ring.

The invention also provides an expression system comprising the promoter of the invention. The expression system comprises the promoter which is operably linked to a transcribable open reading frame. The promoter may be operably linked to a gene or gene fragment (e.g. exon or cDNA). The polynucleotide can encode, for example, a peptide, an oligopeptide, a polypeptide, a protein, or an RNA which is not translated, for example non-coding RNA, tRNA, rRNA, snoRNA, microRNA, siRNA, snRNA, exRNA, piRNA, shRNA, scaRNAs or the long ncRNA. The polynucleotide may encode a plurality of, for example, a peptide, protein, non-coding RNA, tRNA, rRNA, snoRNA, microRNA, siRNA, snRNA, exRNA, piRNA, shRNA, scaRNAs and/or the long ncRNA.

The open reading frame or gene or gene fragment (e.g. cDNA) may encode for a protein such as a membrane protein; optionally wherein the membrane protein comprises a pump, a channel, a pore, a receptor protein, a transporter protein, or a protein which effects cell recognition or a cell-to-cell interaction. The membrane protein is preferably an α-hemolysin (αHL) pore protein.

"Operably linked" refers to an arrangement of elements wherein the components so described are configured so as to perform their usual function. Thus, a given regulatory element, such as a promoter, operably linked to a polynucleotide is capable of effecting the expression of that polynucleotide when the appropriate enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

The expression system may include further transcriptional regulatory elements which control expression from the promoter. Regulatory elements include, but are not limited to, additional promoters, enhancers, initiation sites, internal ribosomal entry sites (IRES), and transcription termination signals, such as polyadenylation signals and poly-U sequences. Such regulatory elements are described, for example, in Goeddel, GENE EXPRESSION TECHNOLOGY: METHODS IN ENZYMOLOGY 185, Academic Press, San Diego, Calif. (1990). Examples of enhancers include WPRE, CMV enhancer, RSV enhancer, the R-U5' segment in LTR of HTLV-I (Mol. Cell. Biol., Vol. 8(1), p. 466-472, 1988), SV40 enhancer, and the intron sequence between exons 2 and 3 of rabbit β-globin (Proc. Natl. Acad. Sci. USA., Vol. 78(3), p. 1527-31, 1981). The regulatory elements may direct expression of a transcript from the promoter of the invention in, for example, any reaction vessel (as described herein), such as a host cell, or may direct expression in certain reaction vessels, such as a certain host cell (e.g., tissue-specific regulatory sequences).

The transcriptional machinery include components which enable and/or enhance transcription from a promoter. Transcriptional components are well known to a person skilled in the art. The promoter, expression system and/or vector described herein may be operably configured for use with transcription components. By the expression system being "operably configured for use" with transcriptional components, the expression system can be expressed using the transcriptional components well known to a person skilled in the art such as those described herein.

The transcriptional components may be eukaryotic or prokaryotic transcription components. For example, the transcription components may be from, or derived from, bacteria, archaea, fungi e.g. yeast, a virus e.g. a bacteriophage, an animal e.g. a mammal, or a plant, or from related systems. Transcription components include, for example, the preinitiation complex, polymerase (such as RNA polymerase, e.g., bacterial RNA polymerase (RNAP) or RNA polymerase I, II or III), TATA-binding protein (TBP), Transcription Factor IIA (TFIIA), Transcription Factor IIB (TFIIB), Transcription Factor IID (TFIID), Transcription Factor IIE (TFIIE), Transcription Factor IIF (TFIIF) and Transcription Factor IIH (TFIIH).

Transcriptional reagents comprise any of the transcriptional components or transcriptional regulatory elements described herein.

The vector of the invention comprises the expression system of the invention. The vector is typically a linear double-stranded DNA molecule or a continuous (e.g. circular) double-stranded DNA molecule. The vector may be for example, plasmid, virus or phage vectors provided with an origin of replication, and, optionally, one or more regulatory elements. The vector may be a retrovirus, lentivirus, adenovirus, adeno-associated virus, baculovirus or herpes simplex virus vector. The vector may be a pXT1, pSG5 (Stratagene), pSVK3, pBPV, pMSG, and pSVLSV40 (Pharmacia). Other suitable vectors would be apparent to persons skilled in the art. By way of further example in this regard reference is made to Sambrook et al. The vector may contain one or more selectable marker genes, for example an ampicillin resistance gene.

Vectors may be used in vitro, for example for the production of DNA or RNA or used to transfect or transform a host cell, for example, a mammalian or bacterial host cell. The vectors may be used to allow in vitro expression of a peptide or protein, or a non-coding RNA, such as a siRNA or miRNA. The vectors may also be adapted to be used in vivo, for example, to allow in vivo expression of a peptide or protein, or a non-coding RNA, such as a siRNA or miRNA. The host cell transformed will be chosen to be compatible with the vector used to transform the cell. The host cell may be bacterial such as E. coli. Any cell with a λ DE3 lysogen, for example C41 (DE3), BL21 (DE3), JM109 (DE3), B834 (DE3), TUNER, Origami and Origami B, can express a vector comprising the T7 promoter. The host cell may be an insect cell, such as Sf9 cells. The host cell may be a CHO, HEK293, HeLa, 3T3, HaCaT, or A549 cell.

The vector (e.g. a cloning vector) may be used to replicate the expression system in a compatible host cell. Thus the expression system may be made by introducing the expression system into a replicable vector, introducing the vector into a compatible host cell, and growing the host cell under conditions which bring about replication of the vector. The vector may be recovered from the host cell. Suitable host cells for cloning are known in the art.

The vector may be any suitable expression vector. The expression vector may then be introduced into a suitable host cell. Thus, the expression system can be expressed in a suitable host cell. The host cell can express the expression system at a high level. Suitable host cells for expression are known in the art.

The expression system or vector may additionally comprise a signal peptide sequence. The signal peptide sequence is generally inserted in operable linkage with the promoter such that the signal peptide is expressed and facilitates targeting to a membrane (such as a lipid bilayer) of, or secretion of, a peptide or protein encoded by a coding sequence also in operable linkage with the promoter.

The promoter and/or the other regulatory elements may be selected to be compatible with the environment in which the promoter, expression system or vector is introduced and expressed. For example the promoter, expression system or vector may be introduced and expressed in vitro, ex vivo or in vivo, for example in a reaction vessel as described herein, such as a biological host cell, synthetic cell, text tube, microtitre plate or multiwell plate.

The invention also provides a delivery system which comprises the vector of the invention. The vector may delivered by, for example viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection or nanoparticle-mediated nucleic acid delivery (see, e.g., Panyam et., al Adv Drug Deliv Rev. 2012 Sep. 13. pii: 50169409X(12)00283-9. doi: 10.1016/j.addr.2012.09.023). The delivery system may comprise a yeast system, a lipofection system, a microinjection system, a biolistic system, virosomes, liposomes, immunoliposomes, polycations, lipid:nucleic acid conjugates or artificial virions. The delivery system may comprise a viral delivery system. The choice of delivery system is generally dependent on where the vector is being delivered to (e.g. the type of cell being transformed) and the circumstances under which the delivery is taking place (e.g., in vitro, ex vivo, or in vivo). A general discussion such methods can be found in Ausubel, et al., Short Protocols in Molecular Biology, 3rd ed., Wiley & Sons, 1995.

The invention also provides a method of expressing a transcript. The expression may be enhanced, increased or initiated. The method comprises providing a reaction vessel, e.g. comprising an aqueous object as define herein, or a composition, e.g. comprising an aqueous object as define herein, of the invention and providing an uncoupling agent to the vessel or composition. The uncoupling agent is capable of uncoupling the one or more transcription inhibition moieties from the one or more components of the promoter, and a transcript is expressed following uncoupling. The uncoupling agent can be any agent which is capable of uncoupling the one or more transcription inhibition moieties from the one or more components of the promoter. The uncoupling agent can be an agent which is capable of cleaving the one or more cleavable moieties. Preferably providing the uncoupling agent can result in photocleavage of the one or more photocleavable moieties. For example, the agent may directly or indirectly photocleave the photocleavable moieties. Thus the agent can be electromagnetic radiation such as the types and wavelengths described herein.

The agent may be provided by any suitable means. The way the agent is provided depends in part on the reaction vessel or composition also being provided. For example, whether the reaction vessel is, for example, in vitro, in vivo or ex vivo, will affect how the agent can be provided. A skilled person will be readily able to determine how the agent can be provided. For example, if the agent is electromagnetic radiation, the electromagnetic radiation may be provided by any suitable method or apparatus such as by a light microscope (e.g. fluorescence), optical fibres, LED driven light delivery systems, fixed spot illuminators, galvo-driven spot illuminators, flexible array-based patterned illuminators or polygon grid scanning.

The invention also provides a method of producing a peptide, oligopeptide, polypeptide or protein comprising the method of expressing a transcript of the invention and translating the transcript into a peptide, oligopeptide, polypeptide or protein.

A skilled person will readily know the machinery required for translation of the coding nucleotide.

The components required for transcription are well known to those of skill in the art. The components will typically comprise a polymerase enzyme, a suitable buffer, triphosphate molecules such as ribonucleotide triphosphates, and cofactors such as magnesium ions. The exact components and conditions required will depend upon the circumstances but can readily be ascertained by one of skill in the art.

Typically, the components required for transcription are provided within the aqueous medium of the reaction vessel, or of the aqueous object or of the composition, assembly or network comprising the reaction vessel or aqueous object.

The components required for transcription may be provided as a "cell-free" system or in vitro transcription system. Many such systems are well known to those skilled in the art (for a review see e.g. Beckert, B et al, Synthesis of RNA by in vitro transcription. *Methods Mol. Biol.* 2011; 703: pp 29-41; doi: 10.1007/978-1-59745-248-9_3). For example, systems based on rabbit reticulocyte lysates, wheat germ extract, bacterial or insect lysates or extracts are commonly employed. Systems based on e.g. T7, T3 or SP6 RNA phage polymerase are available. Such systems are available widely from commercial suppliers. Such components may be directly provided within the aqueous medium of the reaction vessel of the invention, or of the aqueous object of the invention or of the composition, assembly or network comprising the reaction vessel or aqueous object of the invention.

Similarly, in situations where translation of the relevant transcript is required, the components required for translation may additionally be supplied. Cell-free systems for in vitro translation are widely available and may be combined with cell-free systems for in vitro transcription. Such systems may comprise components both for in vitro transcription and for in vitro translation.

Such cell-free systems may be made bespoke or are available commercially, e.g. the PURExpress® system from New England Biolabs, Inc. and the 1-Step Human IVT from Thermo Fisher Scientific Inc.

Where the reaction vessel is a biological cell, the components required for transcription and translation may be expressed or pre-contained within the cell, for example the components may be endogenous to the cell, for example a polymerase enzyme may be encoded by DNA integrated within the genome of the cell.

A microfluidic structure is any microfluidic structure known to a person skilled in the art. Microfluidics are discussed further in Whitesides G. M. (2006), "The origins and the future of microfluidics", Nature 442 (7101): 368-373; Seemann Ralf, Brinkmann Martin, Pfohl Thomas, Herminghaus Stephan (2012), "Droplet based microfluidics", Reports on Progress in Physics 75: 016601; Squires T. M., Quake S. R. (2005), "Microfluidics: Fluid physics at the nanoliter scale", Reviews of Modern Physics 77: 977-1026; and Dahl et al. (2015) "Microfluidic Strategies for Understanding the Mechanics of Cells and Cell-Mimetic Systems", Annu Rev Chem Biomol Eng. 2015; 6:293-317.

Synthetic cells are well known to a skilled person. A synthetic cell may be a minimal cell, artificial cell, cell-like system, semi-synthetic cell or cell-mimetic. For example the synthetic cell may comprise a lipid, e.g. phospholipid, monolayer or bilayer. A synthetic cell may be any synthetic cell discussed further in Dahl et al. (2015) "Microfluidic Strategies for Understanding the Mechanics of Cells and Cell-Mimetic Systems", Annu Rev Chem Biomol Eng. 2015; 6:293-317; Murtas (2009) "Artificial assembly of a minimal cell", Mol Biosyst. 2009 November; 5(11):1292-7; Stano (2011) "Minimal cells: relevance and interplay of physical and biochemical factors" Biotechnol J. 2011 July; 6(7):850-9; and Arkin (2001) "Synthetic cell biology"; Curr Opin Biotechnol. 2001 December; 12(6):638-44.

Reagents, e.g. solutions comprising the promoters, expression systems and vectors of the invention, as defined herein, may be comprised within one or more structures herein referred to as a vessel or vessels or as a reaction vessel or reaction vessels. A vessel or reaction vessel as referred to herein may be any suitable receptacle for receiving reagents comprising the promoters, expression systems and vectors of the invention. Thus, a vessel or reaction vessel may be e.g. a test tube, a well of a microtiter plate, an area of an array, an area of a substrate, a cell/compartment etc. within a microfluidic architecture etc. Accordingly, a vessel may be any structure in which, or on which, the promoters of the invention may be operable.

A vessel or reaction vessel may be an aqueous object as further defined herein. An aqueous object, as referred to herein, may be any suitable structure comprising a volume of aqueous medium. Typically, an aqueous object as described herein is an aqueous droplet comprising an aqueous medium, as defined and described herein. Typically, an aqueous object as described herein may also be a hydrogel object as defined and described herein.

An aqueous object, as described herein, such as an aqueous droplet or hydrogel object as defined and described herein may alternatively not contain promoters, expression systems and vectors of the invention, as defined herein.

The aqueous medium within an aqueous object may be any suitable aqueous medium. For instance, the aqueous medium may be pure water, or an aqueous buffer solution, or an aqueous solution of one or more salts. Alternatively, the aqueous medium may comprise a hydrogel. When the aqueous medium may comprise a hydrogel, the aqueous medium may, for instance, comprise agarose and water. Specific hydrogel are described in more detail herein. The concentration of the agarose in water may be less than or equal to 10% w/v agarose. For instance, the concentration of the agarose in said water may be from 0.25 to 5% w/v agarose. Hydrogels other than agarose may also be used. For instance the aqueous medium may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the aqueous medium may comprise a silicone hydrogel or LB (Luria broth) agar.

The aqueous medium may comprise a combination of the above. For example the aqueous medium may comprise a solution and a hydrogel matrix. The solution may be as defined herein. In such an embodiment the solution may e.g. be disposed within a hydrogel matrix. For instance, the solution may be, e.g. pure water, or an aqueous buffer solution, or an aqueous solution of one or more salts.

In certain embodiments wherein an aqueous object, such as an aqueous droplet or hydrogel object, contains an activatable promoter, expression system and/or vector of the invention, as defined herein, the aqueous medium may contain additional reagents required to give functional effect to the activatable promoter, expression system and/or vector. Such additional reagents are discussed herein. The skilled person will appreciate that the activatable promoters, expression systems and/or vectors of the invention may be operated by conventional means. Thus the skilled person will readily appreciate the nature of the additional reagents which are needed to give functional effect to the activatable promoter, expression system and/or vector in the required context.

One important property of the aqueous medium is pH and this can be varied over a wide range. In some embodiments, for instance, the pH of the aqueous medium within the aqueous object or objects may be in the range of from 5 to 9 (or for instance in the range of from 6 to 8) although higher and lower pHs are also possible. The aqueous medium may therefore be an aqueous buffer solution. Any suitable buffer can be employed, depending on the desired pH. The buffer solution may for instance comprise Tris HCl and KCl. In some embodiments the pH of the aqueous buffer solution is from 5 to 9, or for instance from 6 to 8. The nature and concentration of the solutes can be varied to vary the properties of the solution.

In situations where the aqueous objects defined herein harbour the activatable promoters, expression systems and/or vectors of the invention, the skilled person will readily appreciate the pH parameters which are needed to give functional effect to the activatable promoter, expression system and/or vector in the required context.

The amphipathic molecules are usually as herein defined.

In some embodiments, the aqueous object comprises an outer layer of amphipathic molecules around the surface of the aqueous medium.

The amphipathic molecules may be any suitable amphipathic molecule. Usually, the amphipathic molecules will be ones which are capable, when present in a high enough concentration, of forming a bilayer at any one of said interfaces as defined herein. The type of amphipathic molecule that is capable of forming a bilayer may, for instance, depend on additional components of the contacting aqueous objects. The type of amphipathic molecule that is capable of forming a bilayer may, for instance, depend on whether the aqueous object structure is a network, whether the network is comprised of hydrogel and on the presence and nature of any additional components of an aqueous object network. For example, if the aqueous objects are disposed in a hydrophobic medium, the amphipathic molecules may be, for instance, any suitable amphipathic molecules capable of forming a bilayer between contacting aqueous structures, within a hydrophobic medium. The type of amphipathic molecules capable of forming a bilayer within the hydrophobic medium would typically depend on the nature of the hydrophobic medium and the aqueous medium of the aqueous structures, but a wide range of amphipathic molecules is possible. Similarly, if a network further comprises a hydrophobic medium, the amphipathic molecules may be, for instance, any suitable amphipathic molecules capable of forming a bilayer within the hydrophobic medium. The type of amphipathic molecules capable of forming a bilayer within the hydrophobic medium would typically depend on the nature of the hydrophobic medium and the hydrogel of the hydrogel bodies, but a wide range of amphipathic molecules are possible.

Amphipathic molecules are molecules which have both hydrophobic and hydrophilic groups. The outer layer of amphipathic molecules formed on at least part of the surface of the aqueous object usually comprises a monolayer of amphipathic molecules on said at least part of the surface of the aqueous object. The monolayer is typically formed and maintained naturally by the interaction of the hydrophobic and hydrophilic groups with the aqueous medium so that the molecules align on the surface of the aqueous object with the hydrophilic groups facing inwards towards the aqueous medium and the hydrophobic groups facing outwards, for instance towards a hydrophobic medium. Likewise, the layer of amphipathic molecules that may surround the plurality of aqueous objects usually comprises a monolayer of amphipathic molecules which is formed and maintained spontaneously by the interaction of the hydrophobic and hydrophilic groups.

The amphipathic molecules may, for instance, be non-polymeric amphipathic molecules. Alternatively, the amphipathic molecules may be polymeric amphipathic molecules.

An important class of amphipathic molecules which can be used in an aqueous object is lipid molecules. The lipid molecules may be any of the major classes of lipid, including phospholipids, fatty acids, fatty acyls, glycerolipids, glycerophospholipids, sphingolipids, sterol lipids, prenol lipids, saccharolipids and polyketides. Some important examples include phospholipids and fatty acids, for instance phospholipids. The lipid molecules may be naturally occurring or synthetic. Whilst the formation of a bilayer from lipid molecules has been demonstrated the method is expected to be appropriate for any amphipathic molecules.

A common class of hydrophobic group that may be present in an amphipathic molecule is a hydrocarbon group, as for instance in most lipids. However, another suitable kind of hydrophobic group that may be employed is a fluorocarbon group. Thus, a further important class of amphipathic molecule is an amphipathic molecule that comprises at least one fluorocarbon group. An example of such a molecule would be a lipid-like molecule which comprises a hydrophobic fluorocarbon tail and a hydrophilic head group.

The amphipathic molecules of the aqueous object need not be all of the same type. Rather, the amphipathic molecules may in some embodiments be a mixture of two or more different kinds of amphipathic molecule. Another example is that the amphipathic molecules in the respective outer layers of different aqueous objects in an aqueous structure assembly may be of different types so that, if bilayers are formed, the bilayer(s) formed between the different aqueous objects may be asymmetric.

Typically, therefore, the amphipathic molecules comprise lipid molecules. The lipid molecules need not be all of the same type. Thus, the amphipathic molecules may comprise a single type of lipid or a mixture of two or more different lipid molecules. Likewise, when the aqueous object is in contact with another aqueous objects, the lipid compositions of the outer layers of the individual aqueous objects may be the same as or different from one another. Lipid molecules are particularly advantageous because lipid bilayers, or more generally bilayers of amphipathic molecules, are models of cell membranes and tan aqueous object network or assembly may therefore serve as an excellent platform for a range of experimental studies, including for instance as novel platforms for the fundamental study of membrane proteins, or as multi-compartment protocellular chassis for "bottom-up" synthetic biology.

Phospholipids are particularly preferred for reasons outlined above and also because they are a major component of all cell membranes, making aqueous objects comprising phospholipids particularly suitable for synthetic biology applications, as well as for drug delivery. The phospholipids described below may be non-PEGylated phospholipids.

Accordingly, the amphipathic molecules that form an outer layer on at least part of the surface of the aqueous medium of an aqueous object typically comprise phospholipid molecules. The phospholipid molecules may be the same or different, i.e. the amphipathic molecules comprise a single kind of phospholipid, or a mixture of two or more different phospholipids. Phospholipids are well known to the skilled person and many are commercially available, from suppliers such as Avanti Polar Lipids. The phospholipid molecules may be glycerophospholipids or phosphosphingolipids or a mixture of the two. The phospholipid molecules may comprise anionic phospholipids, phospholipids comprising primary amines, choline-containing phospholipids and/or glycosphingolipids. Usually, the amphipathic molecules comprise one or more glycerophospholipids. As the skilled person will appreciate, glycerophospholipids include, but are not limited to, glycerophospholipids having a structure as defined in the following formula (I):

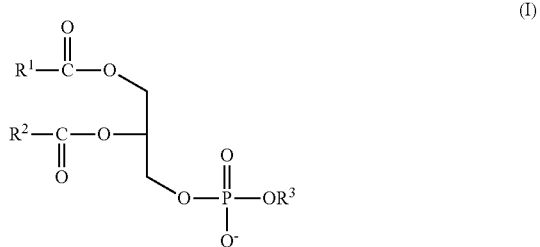

(I)

wherein:
R$^1$ and R$^2$, which are the same or different, are selected from C$_{10}$-C$_{25}$ alkyl groups and C$_{10}$-C$_{25}$ alkenyl groups;
either R$^3$ is absent such that OR$^3$ is O$^-$, or R$^3$ is present and is H, CH$_2$CH$_2$N(R$^4$)$_3^+$, a sugar group, or an amino acid group; and
each R$^4$, which is the same or different, is independently selected from H and unsubstituted C$_1$-C$_4$ alkyl.

Typically, when R$^3$ is CH$_2$CH$_2$N(R$^4$)$_3^+$, each R$^4$, which is the same or different, is selected from H and methyl. As the skilled person will appreciate, when each and every R$^4$ is methyl, the R$^3$ group is a choline group, and when each and every R$^4$ is H, the R$^3$ group is an ethanolamine group.

When R$^3$ is an amino acid group it may for instance be a serine group, i.e. —CH$_2$CH(NH$_2$)(COOH). When R$^3$ is a sugar group, it may for instance be glycerol, i.e. —CH$_2$CHOHCH$_2$OH, or for instance inositol, i.e. —CH(CHOH)$_5$.

Typical examples of R$^1$ and R$^2$ groups are C$_{10}$-C$_{25}$ alkyl groups, including, but not limited to linear C$_{10}$-C$_{25}$ alkyl groups such as, for instance, CH$_3$(CH$_2$)$_{10}$—, CH$_3$ (CH$_2$)$_{12}$—, CH$_3$(CH$_2$)$_{14}$—, CH$_3$(CH$_2$)$_{16}$—, CH$_3$(CH$_2$)$_{18}$—, CH$_3$(CH$_2$)$_{22}$— and branched C$_{10}$-C$_{25}$ alkyl groups such as for instance —CH$_2$—CH(CH$_3$)—(CH$_2$)$_3$—CH(CH$_3$)—(CH$_2$)$_3$—CH(CH$_3$)—(CH$_2$)$_3$—CH(CH$_3$)$_2$.

Further typical examples of R$^1$ and R$^2$ groups are unsubstituted C$_{10}$-C$_{25}$ alkenyl groups, including, but not limited to, CH$_3$(CH$_2$)$_5$CH=CH(CH$_2$)$_7$—, CH$_3$(CH$_2$)$_7$CH=CH(CH$_2$)$_7$—, CH$_3$(CH$_2$)$_4$CH=CHCH$_2$CH=CH(CH$_2$)$_7$—, CH$_3$(CH$_2$)$_4$(CH=CHCH$_2$)$_3$CH=CH(CH$_2$)$_3$—, and CH$_3$CH$_2$CH=CHCH$_2$CH=CHCH$_2$CH=CH(CH$_2$)$_7$—.

As the skilled person will appreciate, the O$^-$ group in the phosphate group adjacent the OR$^3$ group may in some embodiments be protonated, or associated with a suitable cation, for instance a metal cation such as Na$^+$.

Thus, the amphipathic molecules may comprise one or more glycerophospholipids having the structure of formula (I) as defined above.

For instance, the amphipathic molecules may comprise any one or more of the following glycerophospholipids: diphytanoylphosphatidylcholine, diphytanoyl-sn-glycero-3-phosphacholine (DPhPC), diphytanoylphosphatidylethanolamine, 1,2-didecanoyl-sn-glycero-3-phosphocholine, 1,2-dierucoyl-sn-glycero-3-phosphate, 1,2-dierucoyl-sn-glycero-3-phosphocholine, 1,2-dierucoyl-sn-glycero-3-phosphoethanolamine, 1,2-dilinolenoyl-sn-glycero-3-phosphocholine, 1,2-dilauroyl-sn-glycero-3-phosphate, 1,2-dilauroyl-sn-glycero-3-phosphocholine, 1,2-dilauroyl-sn-glycero-3-phosphoethanolamine, 1,2-dilauroyl-sn-glycero-3-phosphoserine, 1,2-dimyristoyl-sn-glycero-3-phosphate, 1,2-dimyristoyl-sn-glycero-3-phosphocholine, 1,2-dimyristoyl-sn-glycero-3-phosphoethanolamine, 1,2-dimyristoyl-sn-glycero-3-phosphoserine, 1,2-dioleoyl-sn-glycero-3-phosphate, 1,2-dioleoyl-sn-glycero-3-phosphocholine, 1,2-dioleoyl-sn-glycero-3-phosphoethanolamine, 1,2-dioleoyl-sn-glycero-3-phosphoserine, 1,2-dipalmitoyl-sn-glycero-3-phosphate, 1,2-dipalmitoyl-sn-glycero-3-phosphocholine, 1,2-dipalmitoyl-sn-glycero-3-phosphoethanolamine (DPPE), 1,2-dipalmitoyl-sn-glycero-3-phosphoserine, 1,2-distearoyl-sn-glycero-3-phosphate, 1,2-di stearoyl-sn-glycero-3-phosphocholine, 1,2-distearoyl-sn-glycero-3-phosphoethanolamine, 1,2-distearoyl-sn-glycero-3-phosphoserine, egg-PC, hydrogenated egg PC, hydrogenated soy PC, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine and 1-stearoyl-2-palmitoyl-sn-glycero-3-phosphocholine, 1,2-diphytanoyl-sn-glycero-3-phosphocholine (DPhPC), 1,2-di stearoyl-sn-glycero-3-phosphocholine (DSPC), 1,2-dipalmitoyl-sn-glycero-3-phosphocholine (DPPC), or 1,2-dipalmitoyl-sn-glycero-3-[phospho-rac-(1-glycerol)] (DPPG), can be employed as the amphiphilic molecules in the aqueous object or network or assembly, or a mixture of one or more thereof. The glycerophospholipid 1,2-dioleoyl-sn-glycero-3-phosphoethanolamine (DOPE) may also be used, and may be used in combination with a pH-sensitive lipid, for instance a fatty acid.

Additionally or alternatively, the amphipathic molecules may comprise a steroid, which steroid comprises an alkyl side-chain. The amphipathic molecules may, for instance, comprise cholesterol, β-sitosterol and lanosterol.

In some embodiments, the amphipathic molecules comprise derivatives of phospholipids. For instance, the amphipathic molecules may comprise a phosphatidylcholine, such as POPC (1-Palmitoyl-2-oleoyl-sn-glycero-3-phosphocholine) or DPPC (1,2-Dipalmitoyl-sn-glycero-3-phosphocholine), or a phosphatidylglycerol, such as POPG (1-palmitoyl-2-oleoyl-sn-glycero-3-phosphoglycerol).

Preferably, the amphipathic molecules comprise DPhPC.

The amphipathic molecules may, for instance, comprise one or more fatty acids, e.g. oleic acid. Fatty acids are of course well known to the skilled person and a wide range of these are commercially available.

The amphipathic molecules may for instance comprise a mixture comprising: (a) one or more phospholipids, and (b) one or more fatty acids.

An alkenyl group is a linear or branched chain hydrocarbon radical comprising one or more double bonds. An alkenyl group may be a C$_{10-25}$ alkenyl group. Examples of C$_{10-25}$ alkenyl groups include those related to C$_{10-25}$ alkyl groups by the insertion of one or more double bonds. Alkenyl groups typically comprise one, two, three or four double bonds. In some cases, an alkenyl group may be a linear alkenyl group.

A phospholipid comprising a PEG group may also be referred to herein as a PEGylated phospholipid. The PEGylated phospholipids may be phospholipids derived from the non-PEGylated phospholipids described above by derivatisation of the non-PEGylated phospholipid with a group comprising a PEG group, for instance a R$^5$ group.

In addition to the amphipathic molecules, the aqueous object, or assembly of aqueous objects or network of aqueous objects may further comprise a PEGylated lipid. PEGylated lipid may be particularly useful when the aqueous object or network/assembly forms part of an aqueous object or network/assembly encapsulate. The term "PEGylated lipid", as used herein, refers to a lipid which has been derivatised with poly(ethylene glycol). For instance, when an aqueous object or network/assembly comprising a plurality of aqueous objects is surrounded by a layer of amphipathic molecules, the layer may further comprise a PEGylated lipid.

The inclusion of one or more PEGylated lipids in the aqueous object or aqueous object network or assembly typically provides stabilisation in vivo, and in particular prolongs the plasma half-life of the aqueous object or aqueous object network or assembly. This means that, when the aqueous object or aqueous object network or assembly contains one or more therapeutic or diagnostic agents, for instance if it is being used as a drug-delivery vehicle, the inclusion of one or more PEGylated lipids may also have the useful effect of prolonging the plasma half-life of the agent within an aqueous object or aqueous object assembly. Such effects have been observed previously when PEGylated lipids are used in liposomal drug formulations. PEGylated lipids are known in the art and are commercially available from suppliers such as NOF Corporation, Japan. Any suitable PEGylated lipid may be employed, including, but not limited to, PEG-phospholipids, diacylglycerol-PEG, cholesterol-PEG derivatives, and mixtures thereof.

In one embodiment, the layer surrounding the plurality of aqueous objects, such as hydrogel objects, of a hydrogel network of the invention further comprises a PEGylated lipid. The peripheral layer may include one or more PEGylated lipids in addition to the amphipathic molecules, for instance multiple copies of the same PEGylated lipid, or a mixture of two or more different classes of PEGylated lipids. Suitable PEGylated lipids include, but are not limited to PEG-phospholipids, diacylglycerol-PEG, cholesterol-PEG derivatives and mixtures thereof.

The poly(ethylene glycol) (PEG) component of the PEGylated lipid may have any one of several different geometries. Thus, it could be substantially linear PEG or branched PEG. The branched PEG may for instance have from three to ten PEG chains emanating from a central core group. Alternatively, the branched PEG could be a star PEG, having from 10 to 100 PEG chains emanating from a central core group. Alternatively, the PEG may be a comb PEG, having multiple PEG chains grafted to a polymer backbone.

The one or more PEGylated lipids employed may for instance comprise a PEG-phospholipid of the following formula (II)

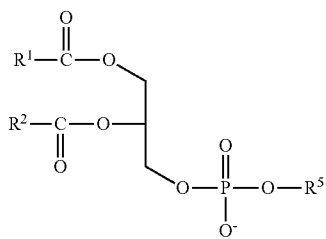

(II)

wherein $R^1$ and $R^2$ are as defined above for the glycerophospholipids of formula (I), and $R^5$ is a group which comprises poly(ethylene glycol).

Preferably, $R^5$ is a group of formula —Y-PEG, wherein:
Y is selected from -alk-, -alk-N($R^N$)—, —C(O)-alk-, -alk-C(O)—, -alk-N($R^N$)—C(O)—, —C(O)—O-alk-, -alk-O—C(O)—;
-alk- is straight chain $C_1$ to $C_6$ alkenyl, preferably ethenyl;
$R^N$ is H or methyl; and
PEG is a poly(ethyleneglycol) group.
Y is preferably —$CH_2CH_2$—NH—C(O)—.

The group which comprises poly(ethylene glycol) may for instance have the formula —$CH_2CH_2NHC(O)$—X, or for instance —$CH_2CH_2NHC(O)(CH_2)_3C(O)$—X wherein X comprises said poly(ethylene glycol). The group X may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

Thus, $R^5$ may for instance be —$CH_2CH_2NHC(O)$—$(OCH_2CH_2)_qOCH_3$, —$CH_2CH_2NHC(O)(CH_2)_3C(O)$—$(OCH_2CH_2)_qOCH_3$, —$CH_2CH_2NHC(O)$—$(OCH_2CH_2)_qOH$, or —$CH_2CH_2NHC(O)(CH_2)_3C(O)$—$(OCH_2CH_2)_qOH$, wherein q is a positive integer. The integer q may for instance be from 5 to 10,000, or for instance from 10 to 1,000. Typically, q is from 10 to 1,000, preferably from 30 to 60.

Alternatively, $R^5$ may be —$(CH_2CH_2O)_qCH_3$ or —$(CH_2CH_2O)_qH$, wherein q is a positive integer. The integer q may for instance be from 5 to 10,000, or for instance from 10 to 1,000, preferably from 10 to 1,000, more preferably from 30 to 60.

The PEGylated phospholipids may comprise a PEG group, and the PEG group may have the formula a —(O—$CH_2CH_2)_q$—O—R group, wherein R is H or methyl and q is a positive integer. The integer q may for instance be from 5 to 10,000, or for instance from 10 to 1,000, preferably from 10 to 1,000, more preferably from 30 to 60. The PEG group is typically an mPEG group. In an mPEG group, R is methyl.

Typically, references to molecular weights of PEG groups are references to the number average molecular weight in the phospholipids comprising a PEG group as a whole. For instance, the number average molecular weight of the PEG groups in the phospholipids is from 1500 to 5000 g/mol, preferably from 1800 to 2200 g/mol, for instance about 2000 g/mol.

Typically, $R^1$ and $R^2$ are each independently groups such that compounds of formula $R^1COOH$ and $R^2COOH$ would be fatty acids selected from caprylic acid (C8), pelargonic acid (C9), capric acid (C10), undecylic acid (C11), lauric acid (C12), tridecylic acid (C13), myristic acid (C14), pentadecanoic acid (C15), palmitic acid (C16), margaric acid (C17), stearic acid (C18), nonadecylic acid (C19), arachidic acid (C20), heneicosylic acid (C21), behenic acid (C22), tricosylic acid (C23), lignoceric acid (C24), pentacosylic acid (C25), α-linolenic acid (C18:3), stearidonic acid (C18:4), eicosapentaenoic acid (C20:5), docosahexaenoic acid (C22:6), linoleic acid (C18:2), γ-linolenic acid (C18:3), dihomo-γ-linolenic acid (C20:3), arachidonic acid (C20:4), adrenic acid (C22:4), palmitoleic acid (C16:1), vaccenic acid (C18:1), paullinic acid (C20:1), oleic acid (C18:1), elaidic acid (Ctrans-18:1), gondoic acid (C20:1), erucic acid (C22:1), nervonic acid (C24:1), mead acid (20:3), phytanic acid (3,7,11,15-tetramethyl hexadecanoic acid).

Additionally or alternatively, the one or more PEGylated lipids may comprise a diacylglycerol-PEG of formula (III)

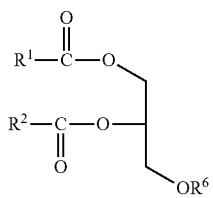

(III)

wherein $R^1$ and $R^2$ are as defined above for the glycerophospholipids of formula (I), and $R^6$ is a group which comprises poly(ethylene glycol).

The poly(ethylene glycol) may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^6$ may for instance be —$(CH_2CH_2O)_qCH_3$, —$(CH_2CH_2O)_qH$, —$CH_2CH_2NHC(O)$—$(OCH_2CH_2)_qOCH_3$, —$CH_2CH_2NHC(O)$—$(OCH_2CH_2)_qOH$, —$CH_2CH_2NHC(O)(CH_2)_3C(O)$—$(OCH_2CH_2)_qOCH_3$ or —$CH_2CH_2NHC(O)(CH_2)_3C(O)$—$(OCH_2CH_2)_qOH$
wherein q is a positive integer. The integer q may for instance be from 5 to 10,000, or for instance from 10 to 1,000.

Additionally or alternatively, the one or more PEGylated lipids may comprise a cholesterol-PEG derivative of formula (IV)

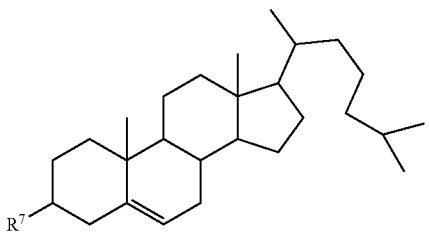

(IV)

wherein $R^7$ is a group which comprises poly(ethylene glycol).

Again, the poly(ethylene glycol) may comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^7$ may for instance be —(OCH$_2$CH$_2$)$_q$OH or —(OCH$_2$CH$_2$)$_q$OCH$_3$ wherein q is a positive integer. The integer q may for instance be from 5 to 10,000, or for instance from 10 to 1,000.

Polyglycerine may be used instead of poly(ethylene glycol).

In certain preferred embodiments the amphipathic molecules of the invention may comprise a mixture of non-PEGylated phospholipids and PEGylated phospholipids. The non-PEGylated phospholipids and PEGylated phospholipids may be any of the non-PEGylated phospholipids and PEGylated phospholipids described herein.

Such a mixture may comprise phospholipids comprising non-PEGylated phospholipids and PEGylated phospholipids, and wherein from 2.5 to 15 mol % of the phospholipids are PEGylated phospholipids. Preferably, from 5 to 15 mol % of the phospholipids may be PEGylated phospholipids. More preferably, from 7.5 to 15 mol % of the phospholipids may be PEGylated phospholipids. Even more preferably, from 10 to 15 mol % of the phospholipids may be PEGylated phospholipids.

In such mixtures the PEGylated phospholipids may comprise a PEG group which has a molecular weight of from 1500 to 5000 g/mol, optionally a molecular weight of from 1800 to 2200 g/mol.

In such mixtures the non-PEGylated phospholipids may be glycerophospholipids and/or the PEGylated phospholipids may be glycerophospholipids.

In such mixtures the non-PEGylated phospholipids are phospholipids of formula (I):

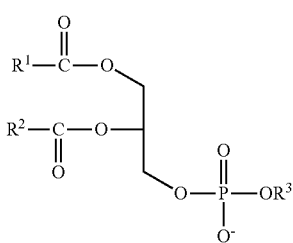

(I)

wherein:
$R^1$ and $R^2$, which are the same or different, are selected from $C_{10}$-$C_{25}$ alkyl groups and $C_{10}$-$C_{25}$ alkenyl groups;
$R^3$ is absent such that OR$^3$ is O$^-$, or $R^3$ is present and is H, CH$_2$CH$_2$N(R$^4$)$_3^+$, a sugar group, or an amino acid group; and
each $R^4$, which is the same or different, is independently selected from H and unsubstituted $C_1$-$C_4$ alkyl.

In such mixtures the PEGylated phospholipids may be phospholipids of the following formula (II)

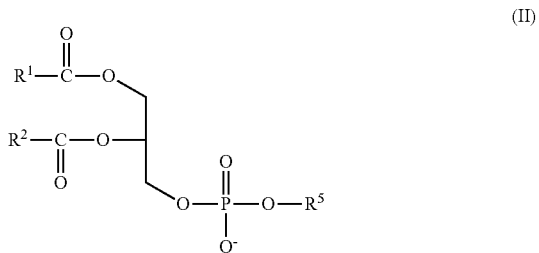

(II)

wherein:
$R^1$ and $R^2$ are as defined above for the phospholipids of formula (I), and $R^5$ is a group which comprises poly(ethylene glycol).
$R^5$ may be —CH$_2$CH$_2$NHC(O)—(OCH$_2$CH$_2$)$_q$OCH$_3$, —CH$_2$CH$_2$NHC(O)(CH$_2$)$_3$C(O)—(OCH$_2$CH$_2$)$_q$OCH$_3$, —CH$_2$CH$_2$NHC(O)—(OCH$_2$CH$_2$)$_q$OH, or —CH$_2$CH$_2$NHC(O)(CH$_2$)$_3$C(O)—(OCH$_2$CH$_2$)$_q$OH, wherein q is an integer from 5 to 10,000.

The PEGylated phospholipids may comprise a PEG group, and the PEG group may have the formula a —(O—CH$_2$CH$_2$)$_q$—O—R group, wherein R is H or methyl and q is a positive integer. The integer q may for instance be from 5 to 10,000, or for instance from 10 to 1,000, preferably from 10 to 1,000, more preferably from 30 to 60.

In any such mixtures, the non-PEGylated phospholipids may comprise DPhPC.

In any such mixtures, the PEGylated phospholipids may comprise DPPE-mPEG2000.

In any such mixtures, the phospholipids may comprise DPhPC and DPPE-mPEG2000, and wherein the phospholipids comprise from 2.5 to 15 mol % of DPPE-mPEG2000. Preferably, from 5 to 15 mol % of the phospholipids may be DPPE-mPEG2000. More preferably, from 7.5 to 15 mol % of the phospholipids may be DPPE-mPEG2000. Even more preferably, from 10 to 15 mol % of the phospholipids may be DPPE-mPEG2000, for instance 10 or 15 mol % of the phospholipids may be DPPE-mPEG2000.

Aqueous objects as defined herein comprising an aqueous medium may further comprise an outer layer of a mixture of phospholipid molecules on at least part of the surface of the aqueous object, wherein the mixture of phospholipid molecules is a mixture of non-PEGylated phospholipids and PEGylated phospholipids as defined above. The outer layer of phospholipid molecules may encapsulate the aqueous object. The aqueous object, or reaction vessel, may be any aqueous droplet defined herein or any hydrogel object as defined herein Any such aqueous object(s), or reaction vessel(s), may be disposed in a hydrophobic medium. The hydrophobic medium may comprise an oil. The oil may comprise a silicone oil, a hydrocarbon, or a fluorocarbon, or a mixture of two or more thereof. The hydrophobic medium may comprise a mixture of a hydrocarbon and silicone oil. The hydrophobic medium may comprise a mixture of a hydrocarbon and silicone oil comprising a ratio of hydrocarbon:silicone oil of from 80:20 to 20:80 by volume, or from 70:30 to 30:70 by volume. The ratio of hydrocarbon:silicone oil is preferably in a ratio of from 60:40 to 40:60 by volume, for instance 50:50 to 40:60. The ratio is preferably 50:50, 40:60 or 45:55 by volume. The hydrocarbon may be a C10-C20 alkane, preferably a hexadecane.

The concentration of amphipathic molecules may be any suitable concentration.

Typically, the concentration of amphipathic molecules is less than or equal to 15 mg mL$^{-1}$. For instance, the concentration of amphipathic molecules may be from greater than 0 to 10 mg mL$^{-1}$. Usually, the concentration of amphipathic molecules is from 0.25 mg mL$^{-1}$ to 10 mg mL$^{-1}$, for instance, from 0.25 mg mL$^{-1}$ to 5 mg mL$^{-1}$. More typically, the concentration of amphipathic molecules is from 0.25 mg mL$^{-1}$ to 2.5 mg mL$^{-1}$, for instance, from 0.25 mg mL$^{-1}$ to 1.5 mg mL$^{-1}$.

In some embodiments, the concentration of amphipathic molecules is about 1 mg mL$^{-1}$.

The inventors have furthermore found that the concentration of amphipathic molecules can be changed in order to control whether or not an interface between aqueous objects comprises a bilayer of amphipathic molecules. High concentrations ensure an interface will comprise a bilayer of amphipathic molecules. Increases in the concentration of amphipathic molecules may therefore be used to increase the number of interfaces comprising a bilayer of amphipathic molecules and decrease the number of interfaces that do not comprise a bilayer of amphipathic molecules. Decreasing the concentration of amphipathic molecules may be used to decrease the number of interfaces comprising a bilayer of amphipathic molecules. For example, decreasing the concentration of amphipathic molecules may be used to increase the number of interfaces at which two aqueous objects, e.g. hydrogel bodies, are in direct contact.

As the skilled person will appreciate, the concentration of amphipathic molecules required for the formation of a bilayer at an interface may depend upon the size and shape of the aqueous object, e.g. hydrogel body.

Further, changing the concentration of amphipathic molecules is not the only way to control whether or not an interface comprises a bilayer of amphipathic molecules. For example, a bilayer of amphipathic molecules between two aqueous objects, e.g. hydrogel objects, in a network may be removed by pushing together the two objects, in order to "squeeze out" the bilayer from between the two objects and/or prevent a bilayer from being formed between the objects. Thus, the concentration of amphipathic molecules may not be the only factor that dictates whether a bilayer is formed.

Typically, the concentration of amphipathic molecules is less than or equal to 15 mg mL$^{-1}$. For instance, the concentration of amphipathic molecules may be from 0 to 10 mg mL$^{-1}$.

In some embodiments, the concentration of amphipathic molecules is usually equal to or greater than 0.5 mg mL$^{-1}$. For instance, the concentration of amphipathic molecules may be equal to or greater than 5 mg mL$^{-1}$. Usually, the concentration of amphipathic molecules is from 0.5 mg mL$^{-1}$ to 15 mg mL$^{-1}$, for instance, from 5 mg mL$^{-1}$ to 15 mg mL$^{-1}$. In order for a bilayer to form at an interface, the concentration of amphipathic molecules usually needs to be equal to or greater than 1 mg mL$^{-1}$, for instance equal to or greater than 5 mg mL$^{-1}$.

In other embodiments, the concentration of amphipathic molecules is from 0.5 to 10 mg mL$^{-1}$. Usually, the concentration of amphipathic molecules is from 5 to 10 mg mL$^{-1}$. The inventors have found that these concentration ranges are favourable for stabilising aqueous object networks, particularly hydrogel networks, that comprise at least one interface that comprises a bilayer of amphipathic molecules and at least one other interface that does not comprise a bilayer of amphipathic molecules. Likewise, these concentration ranges have been found to favour aqueous object networks, particularly hydrogel networks, which comprise at least one interface that comprises a bilayer of amphipathic molecules, and at least one other interface at which the hydrogel body of one hydrogel object is in direct contact with the hydrogel body of another hydrogel object. In this case, the concentration of the amphipathic molecules may therefore be from 5 to 10 mg mL$^{-1}$.

In a further embodiment, the concentration of amphipathic molecules is less than or equal to 5 mg mL$^{-1}$, for instance, less than or equal to 2 mg mL$^{-1}$. These concentration ranges often favour networks in which the interfaces do not comprise bilayers.

The concentrations of amphipathic molecules referred to in the previous paragraphs are typically the concentrations of the amphipathic molecules in the hydrophobic medium, i.e. in the hydrophobic medium in which the plurality of aqueous, e.g. hydrogel, objects is disposed.

When a hydrophilic material is placed in a medium comprising amphipathic molecules, the hydrophilic component of the amphipathic molecules will be attracted to the hydrophilic material. Thus a layer of amphipathic molecules will form on at least part of the surface of the hydrophilic material. Typically, the medium is a hydrophobic medium. When the concentration of amphipathic molecules in the medium is high enough, the layer will usually be a monolayer that covers the entire surface of the hydrophilic material. The concentration of amphipathic molecules required to form a monolayer will depend on factors such as the surface area of the hydrophilic material and whether or not there are other hydrophilic materials in the same medium. There may be other factors that influence whether a monolayer of amphipathic molecules is formed. For instance, if the hydrophilic material has a particularly intricate shape, it may only be possible for a layer to form on part of the surface of the hydrophilic material.

In the present invention, the individual aqueous objects such as droplets and hydrogel objects comprise a hydrophilic material. As discussed below, the aqueous objects and networks thereof are usually disposed in a hydrophobic medium and this hydrophobic medium typically comprises amphipathic molecules. If so, amphipathic molecules in the bulk hydrophobic phase form an outer layer of amphipathic molecules on at least part of the surface of the aqueous object, e.g. hydrogel object. When the aqueous object comprises a hydrogel object, the entire surface or at least part of the surface of the body of the hydrogel object may comprise an outer layer of amphipathic molecules. In other embodiments the body of a hydrogel object may comprise no outer layer of amphipathic molecules. Typically, when the aqueous object comprises an aqueous droplet the entire surface of aqueous droplet may comprise an outer layer of amphipathic molecules.

Typically, the aqueous object, or aqueous object network or assembly is disposed in a hydrophobic medium and the concentration of amphipathic molecules is the concentration of amphipathic molecules in the hydrophobic medium.

Additionally or alternatively, when the aqueous objects, or aqueous object networks or assemblies are formed, the aqueous medium of the aqueous objects, networks or assemblies may comprise amphipathic molecules. The concentration of amphipathic molecules may therefore be the concentration of amphipathic molecules in the aqueous medium.

The hydrophobic medium may be selected from a wide range of materials. The hydrophobic medium may comprise a single hydrophobic compound. Alternatively, it may comprise a mixture of two or more different hydrophobic compounds. The hydrophobic medium may, for instance, be selected to affect the buoyancy of the aqueous object or aqueous object network or assembly and the speed of formation of the layer of amphipathic molecules around at least part of the aqueous object after the aqueous object is first introduced into the hydrophobic medium or around at least part of each aqueous object in a network or assembly when preparing the network or assembly.

The hydrophobic medium is typically an oil. The oil may be a single, pure, compound, or the oil may comprise a mixture of two or more compounds. It is usually desirable that the oil does not significantly destabilize any bilayers formed.

The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils.

Any suitable silicone oil may be used. For instance, the oil may comprise silicon oil DC200 (a polymer comprising monomer units of —O—Si(CH$_3$)$_2$—), poly(dimethylsiloxane) (PDMS), hydroxy terminated, or PDMS 200.

Additionally or alternatively, the oil may comprise a hydrocarbon. When the oil comprises a hydrocarbon it may comprise a single hydrocarbon compound, or a mixture of two or more hydrocarbons.

In some embodiments, the oil is a mixture comprising: (a) one or more hydrocarbons, and (b) one or more silicone oils. The hydrocarbon may, for instance, be any suitable liquid hydrocarbon. Whether a particular hydrocarbon is liquid will depend upon the temperature of the hydrophobic medium. Thus the term liquid hydrocarbon refers to a hydrocarbon that is a liquid at the temperature that the hydrophobic medium is at. Typically, the hydrophobic medium will be at room temperature. However, in some embodiments, the hydrophobic medium may be above or below room temperature.

In some embodiments, the oil may comprise a solid. A solid hydrocarbon may, for instance, be used in combination with a silicone oil. The oil may, for instance, be a mixture of solids that dissolve to form a liquid.

When the oil comprises a hydrocarbon, the hydrocarbon may be branched or unbranched, for example a hydrocarbon having from 5 to 40 carbon atoms, or from 5 to 30 carbon atoms (although hydrocarbons of lower molecular weight would require control of evaporation). Preferably, the hydrocarbon is a liquid at the operating temperature of the aqueous object, network or assembly used in the invention. Suitable examples include alkanes or alkenes, such as hexadecane, decane, pentane or squalene. Usually, the oil comprises a hydrocarbon.

Typically the hydrocarbon is an unsubstituted $C_{10}$-$C_{20}$ alkane, for instance hexadecane.

Shorter alkanes may be suitable, for instance, in assemblies for which buoyancy effects are less important and whose outer layer of amphipathic molecules, on at least part of the surface of the aqueous object, network or assembly, may form more quickly.

In some embodiments the hydrocarbon is a longer-chain hydrocarbon, such as an unsubstituted $C_{15}$-$C_{40}$ alkane. For instance, an unsubstituted $C_{16}$-$C_{30}$ alkane chain, such as squalene.

In one embodiment, the hydrophobic medium comprises an unsubstituted $C_{10}$-$C_{20}$ alkane and the amphipathic molecules comprise one or more glycerophospholipids. For instance, the hydrophobic medium may comprise hexadecane and the outer layer of amphipathic molecules may comprise DPhPC.

Other types of oil are possible. For example the oil may be a fluorocarbon. This might be useful for the study of some systems, for example to minimise loss of a particular membrane protein or analyte from an aqueous object, network or assembly or to control gas content such as oxygen. Because fluorocarbons can be both hydrophobic and lipophobic, an oil phase that comprises fluorocarbons can usefully prevent the adhesion of aqueous object, networks or assemblies to surfaces.

In another embodiment, the hydrocarbon is a bromo-substituted $C_{10}$-$C_{30}$ alkane, or for instance a bromo-substituted $C_{10}$-$C_{20}$ alkane, e.g. bromododecane. Although bromododecane was found to require long incubation times for the formation of an outer layer of amphipathic molecules, on at least part of the surface of the aqueous object, network or assembly, this oil should be more suitable for other aqueous objects, networks or assemblies whose outer layer of amphipathic molecules, on at least part of the surface of the aqueous object, network or assembly, may incubate more quickly.

Typically, the oil comprises silicone oil or a hydrocarbon. Any suitable silicone oil may be employed. Usually, the silicone oil is as herein defined.

Silicone oil is advantageous on account of its density being close to that of water, which ensures that an aqueous object, such as a droplet, is approximately neutrally buoyant in water. The silicone oil may for instance be poly phenyl methyl siloxane, which has a density of about 1 g·cm$^{-3}$.

The hydrocarbon typically has from 5 to 30 carbon atoms (a $C_5$-$C_{30}$ hydrocarbon), more typically from 10 to 30 carbon atoms (a $C_{10}$-$C_{30}$ hydrocarbon). Typically, it is an alkane or an alkene. Thus, the hydrocarbon may be a $C_5$-$C_{30}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. In one embodiment it is squalene. In a preferred embodiment, the hydrocarbon is an unsubstituted $C_5$-$C_{20}$ alkane, preferably an unsubstituted $C_{10}$-$C_{20}$ alkane. The hydrocarbon may for instance be squalene, hexadecane or decane. However, in some embodiments the hydrocarbon may be substituted with a halogen atom, for instance bromine.

In some embodiments, the hydrophobic medium comprises a mixture of silicone oil and a hydrocarbon. Such mixtures have been found to provide advantageously low incubation times for stable objects, such as droplets, to be formed. The silicone oil and hydrocarbon in the mixture may be as further defined above. Typically, the hydrocarbon is an unsubstituted $C_{10}$-$C_{20}$ alkane, preferably hexadecane. The silicone oil and hydrocarbon mixture typically has a density close to that of water, to ensure an aqueous object, such as a droplet, has approximately neutral buoyancy in aqueous media; it may for instance be poly phenyl methyl siloxane. Usually, the volume ratio of the silicone oil to the hydrocarbon is equal or greater than 0.5:1. The volume ratio of the silicone oil to the hydrocarbon may for instance be from 0.5:1 to 5:1, for instance about 1:1. In some embodiments, the volume ratio of the silicone oil to the hydrocarbon is equal or greater than 5:1.

The hydrophobic medium employed may, for instance, have a density close to that of water, for instance a density of about 1 g·cm$^{-3}$, such that an aqueous object, such as a droplet, is approximately neutrally buoyant in water.

In one embodiment, the hydrophobic medium comprises both silicone oil and hexadecane. Typically the silicone oil is poly phenyl methyl siloxane. The volume ratio of the silicone oil to the hexadecane is typically equal or greater than 0.5:1, for instance from 0.5:1 to 5:1. It may for instance be about 1:1. In some embodiments, the volume ratio of the silicone oil to the hydrocarbon is equal or greater than 5:1.

Preferably, the hydrophobic medium comprises hexadecane. In some embodiments, the hydrophobic medium further comprise silicone oil.

Typically, the hydrophobic medium comprises hexadecane and the amphipathic molecules comprise DPhPC. More typically, the hydrophobic medium comprises hexadecane, the amphipathic molecules comprise DPhPC and the aqueous medium comprises an aqueous buffer solution.

Usually, the hydrophobic medium comprises hexadecane, the amphipathic molecules comprise DPhPC, the aqueous medium comprises an aqueous buffer solution and the magnetic material, if included, comprises nickel.

In some hydrogel embodiments, the hydrophobic medium comprises hexadecane, the amphipathic molecules comprise DPhPC and the hydrogel in the hydrogel bodies comprises agarose. Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

The aqueous object may comprise a hydrogel object. The hydrogel object has a hydrogel body.

The body of the hydrogel object comprises a mass of hydrogel and may be any shape. Accordingly, the hydrogel body may be any regular or irregular shape, or any polygon. When the hydrogel body is a polygon, it may be convex or non-convex.

Usually the hydrogel body is a three-dimensional shape. It may thus be any three-dimensional shape. As the skilled person will appreciate, a three-dimensional shape may have three dimensions that are all the same order of magnitude, it may have one dimension that is at least an order of magnitude larger or smaller than the other two dimensions, or all three dimensions of the shape may be of different orders of magnitude.

The hydrogel body shape may, for instance, be spherical or a shape comprising two or more sides. In some embodiments, the hydrogel shape comprises from 1 to 50 sides, for instance from 1 to 15 sides. The hydrogel shape may, for example, be a 2-sided shape such as a hemisphere; a 3-sided shape such as a cylinder, a bended cylinder, or a 3-sided wire; a 5-sided shape such as a triangular prism; a 6-sided shape such as a cuboid; or a 14-sided shape such as a cross-shape.

Typically, the hydrogel body is spherical, cross-shaped, cuboid, crescent-shaped, prism-shaped, cylindrical, wire-shaped or a shape which has a triangular, pentagonal, hexagonal, heptagonal, octagonal, nonagonal, decagonal, undecagonal, dodecagonal, square or rectangular face.

It follows that the hydrogel object may also be any shape.

Two or more individual hydrogel objects may be comprised in a hydrogel network. Individual hydrogel bodies in the hydrogel network may be any shape. It thus follows that different hydrogel objects in a hydrogel network of the invention may be all the same shape or the hydrogel network may comprise hydrogel objects that are a variety of different shapes. When the hydrogel network comprises different-shaped hydrogel objects, the hydrogel objects need not necessarily all have different shapes. Thus, for instance, in a network comprising five hydrogel objects one of the hydrogel objects may be cross-shaped and four of the hydrogel objects may be crescent shaped.

The hydrogel of the hydrogel body may comprise any suitable hydrogel. The hydrogel typically comprises a high weight percent of water.

Usually, the hydrogel comprises agarose. Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

Hydrogels other than agarose may also be used. For instance the hydrogel body may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the hydrogel body may comprise a silicone hydrogel or LB (Luria broth) agar.

In some embodiments wherein the aqueous object comprises a hydrogel object, at least one hydrogel body comprises a hydrophilic material and a hydrophobic material. The hydrophilic material is typically agarose. The hydrogel body comprising a hydrophilic material and a hydrophobic material may, for example, be a spherical hydrogel body made up of a hemisphere of a hydrophilic material and a hemisphere of a hydrophobic material, and may therefore be considered to have two faces. A hydrogel object comprising a hydrogel body comprising a hydrophilic material and a hydrophobic material has therefore been termed a "Janus particle".

Within a network of aqueous objects, which may be e.g. a network of aqueous droplets or a network of hydrogel objects, each of said aqueous objects may contact another of said aqueous objects. The boundary that is shared between contacting aqueous objects, at the point of contact between the objects, is referred to herein as an interface. Thus, each of said aqueous object in the network may contact another of said aqueous objects to form an interface between that aqueous object and the other aqueous object. An interface is thus formed when part of the outer layer of one aqueous object contacts part of the outer layer of another aqueous object.

As the skilled person will appreciate, two aqueous objects may share a single interface, or two or more interfaces. For instance, if the aqueous object network comprises a hydrogel network comprising a hydrogel wire, the hydrogel wire may be in contact with another hydrogel object at two points to form two separate interfaces (as shown e.g. in FIG. 10a of International patent application publication number WO 2014/064459; the contents of which are incorporated herein by reference). Similarly, if the aqueous object network comprises a hydrogel network comprising a crescent-shaped hydrogel object the crescent-shape may be in contact with another hydrogel object at two points to form two separate interfaces (as shown e.g. in FIG. 5c of WO 2014/064459). Complementary regions of two hydrogel objects may, for instance, fit together in a lock-and-key arrangement with more than one interface forming between the two hydrogel objects. For instance, two cross-shaped hydrogel objects may fit together in a lock-and-key arrangement (as shown e.g. in FIG. 5e of WO 2014/064459).

Typically, an aqueous object such as a hydrogel object not in contact with another aqueous object such as a hydrogel object will comprise a complete monolayer of amphipathic molecules. When two such aqueous objects comprising a monolayer of amphipathic molecules are brought together, a bilayer of amphipathic molecules will quickly form at the interface between the two aqueous objects. The bilayer forms as it is an energetically more favourable configuration for the amphipathic molecules to adopt. The shape of the bilayer formed will be the shape with the lowest free surface energy. As discussed below, the size of the bilayer can be adjusted by pushing the aqueous objects together or pulling the aqueous objects apart. Further, the bilayer can be removed, for example, by pushing the aqueous objects together and effectively squeezing out the bilayer.

Thus a bilayer may be formed when two aqueous objects come together. The aqueous objects may, for instance, be brought together using a micromanipulator. Each aqueous object comprises an outer layer of amphipathic molecules, on at least part of the surface of the aqueous object. Providing that the concentration of amphipathic molecules is high enough, when the two aqueous objects come together, the amphipathic molecules at the interface spontaneously form a bilayer. The present inventors have found that the presence or absence of a bilayer between any two aqueous objects may be controlled, for example, by pushing two aqueous objects together or pulling them apart and/or by increasing or decreasing the concentration of amphipathic molecules surrounding the aqueous bodies. Likewise, the area of the bilayer can be controlled, for example, by pushing two aqueous objects together or pulling them apart and/or by increasing or decreasing the concentration of amphipathic molecules surrounding the aqueous objects. Typically, the plurality of aqueous objects, such as aqueous droplets or hydrogel objects is disposed in a hydrophobic medium and thus the concentration of amphipathic molecules will typically be the concentration of amphipathic molecules in the hydrophobic medium.

When the network of aqueous objects comprises a hydrogel network comprising a Janus particle, only the amphipathic molecules in contact with the hydrophilic material of the Janus particle are able to form a bilayer of amphipathic molecules with a neighbouring hydrogel object. This is because of the orientation of the amphipathic molecules around the surface of the hydrogel body of the Janus particle. The amphipathic molecules attracted to the hydrophilic material of the Janus particle will be orientated with their head groups nearest the hydrophilic surface. The amphipathic molecules attracted to the hydrophobic material of the Janus particle will be orientated with their head groups away from the hydrophilic surface. Thus, the amphipathic molecules attracted to the hydrophobic material of the Janus particle are not able to form a bilayer of amphipathic molecules with a neighbouring hydrogel object.

It is possible to detect the formation of a bilayer by measuring the specific capacitance at the interface. A standard voltage protocol may be used.

An aqueous object network may comprise one interface, or it may comprise two or more interfaces. Any of the interfaces in the aqueous object network may comprise a bilayer of amphipathic molecules. The bilayers may be formed as discussed above. Similarly, any of the interfaces in the network may not comprise a bilayer of amphipathic molecules. Bilayers will not be formed, for instance, when the two aqueous objects at the interface are pushed together with enough force to effectively squeeze out the amphipathic molecules at the interface, or when the concentration of amphipathic molecules is too low to form a bilayer. Thus, when the aqueous object network comprises two or more interfaces it is possible, for instance, that: (i) all of the interfaces in the network comprise a bilayer of amphipathic molecules; (ii) none of the interfaces in the network comprises a bilayer of amphipathic molecules; or (iii) at least one of the interfaces comprises a bilayer of amphipathic molecules and at least one of the interfaces does not comprise a bilayer of amphipathic molecules.

When there is no bilayer of amphipathic molecules at an interface between two aqueous objects, the two objects may, or may not, be in direct contact with each other at the interface. The interface may for instance comprise a layer of a material or a compound other than a bilayer of amphipathic molecules. There may, for instance, be a thin layer of an aqueous medium (e.g. a thin layer of water, or a thin layer of an aqueous solution) between the two objects.

Wherein the aqueous object is a hydrogel object, typically the surface of the hydrogel object at the molecular level is not completely smooth. The agarose polymer chains of an agarose hydrogel object, for instance, usually do not lie flat along the edge of the hydrogel body, but rather create a "fuzzy edge" to the hydrogel body. Thus, when there is no bilayer of amphipathic molecules at an interface between two contacting hydrogel objects, the two hydrogel objects may be in direct contact with each other at the interface, and the agarose polymer chains at the edge of one hydrogel body will interact to a certain extent with the agarose polymer chains at the edge of the adjacent hydrogel body. The chains from different objects may for instance intermingle and become entangled with each other to a certain extent. However, as the skilled person will appreciate, the extent to which such polymer chains become intermingled or entangled with each other and interact at the interface will be significantly less than the degree of chain entanglement, bonding and interaction within the bulk of a hydrogel object. The agarose polymer chains within the bulk of a hydrogel body will form significantly stronger intermolecular interactions with each other, and will be significantly more entangled, than the chains of the two different hydrogel objects at the interface between the objects. The fact that the interactions are stronger in the bulk of a hydrogel object than between two different hydrogel objects contributes to the strengths of the hydrogel objects and helps them to retain their shape. It also explains why two or more different hydrogel objects can be placed adjacent to one another, in direct contact with each other, without merging to form a single object. It also explains why two or more directly-contacting hydrogel objects may be pulled apart again easily, and, if they are pulled apart, why they will generally come apart again at the original interface.

Accordingly, when there is no bilayer of amphipathic molecules at an interface between two hydrogel objects, the two hydrogel objects may be in direct contact with one another at the interface. In some embodiments, the hydrogel objects at the interface may be in direct contact at some points of the interface and not at others. This may occur, for example, when one or both of the hydrogel objects has an uneven surface and/or when there is a thin layer of aqueous medium between the hydrogel objects at only part of the interface.

The inventors have found that the presence of a bilayer between two hydrogel objects delimits the individual hydrogel objects to a greater extent. This delimitation can be observed, for example, by studying the transport of a dye through the hydrogel network. Usually, no dye will be transported across an interface that comprises a bilayer of amphipathic molecules.

Figure 7A:
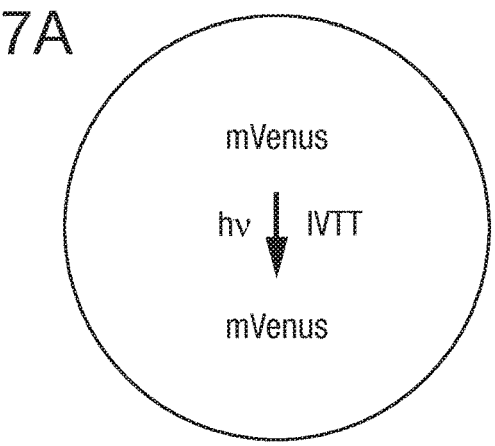
FIG. 7 shows expression from amine-only mVenus DNA and LA-mVenus DNA in synthetic cells. (A) Schematic of a synthetic cell containing amine-only mVenus DNA. (B) Synthetic cells containing amine-only DNA express protein with or without light activation. (C) Fluorescence intensity line profile of B. The +UV line is to the right at above 400 (D) Schematic of a synthetic cell containing LA-mVenus DNA. (E) Synthetic cells containing LA-mVenus DNA expressed mVenus (white/light-grey) upon light activation. (F) Fluorescence intensity line profile of E. Top line is +UV and bottom line next to X-axis is -UV.
Figure 7B:
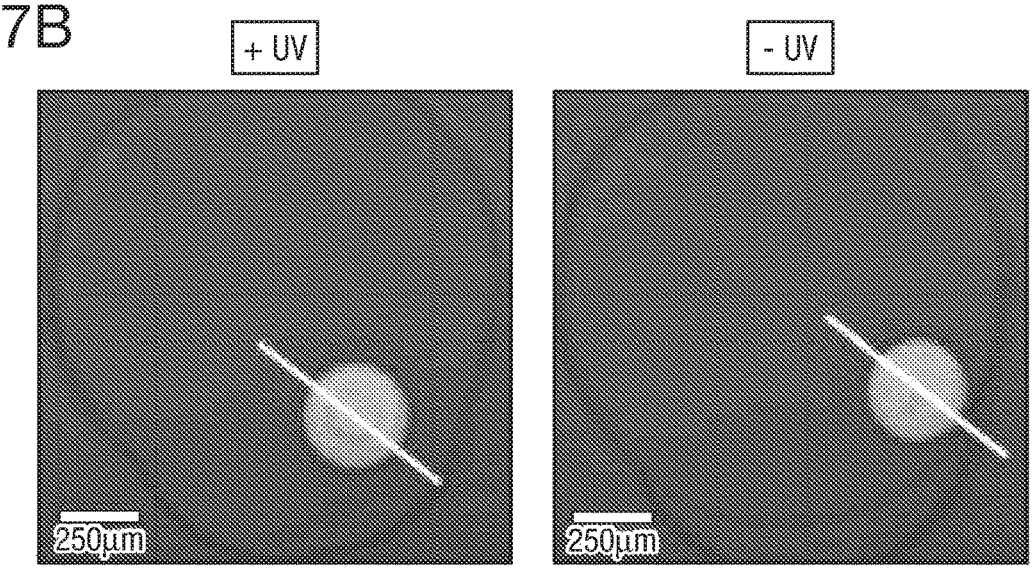
Figure 7C:
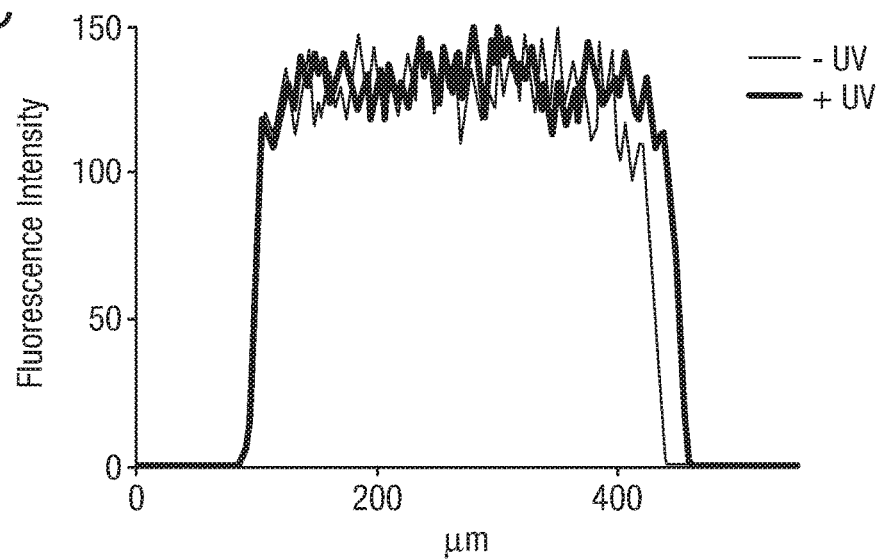
Figure 7D:
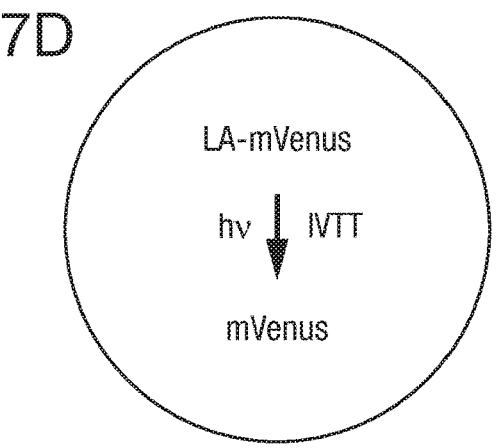
Figure 7E:
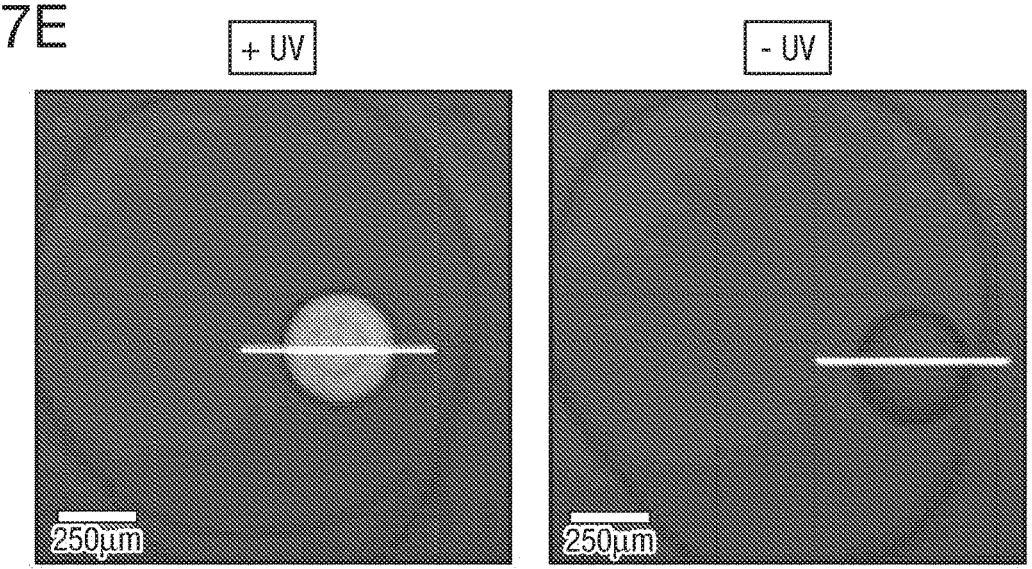
Figure 7F:
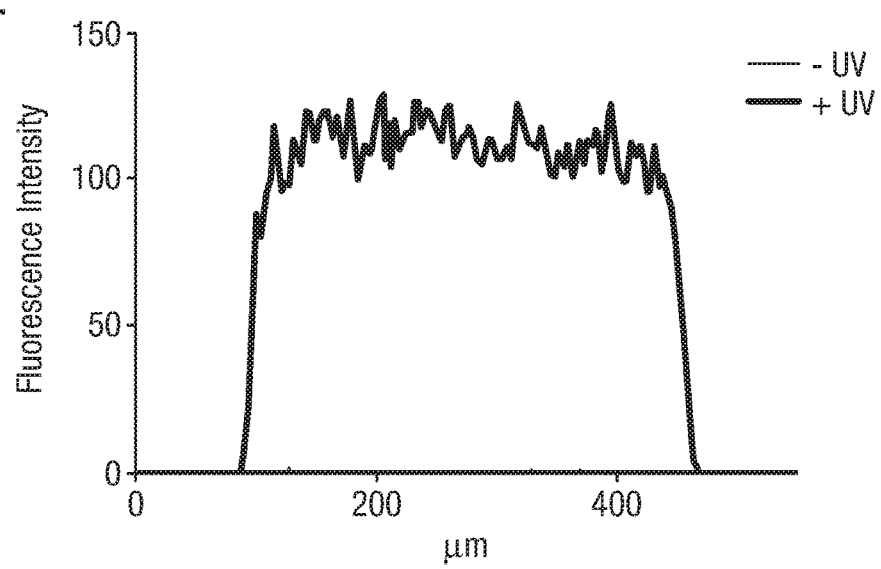
Figure 8B:
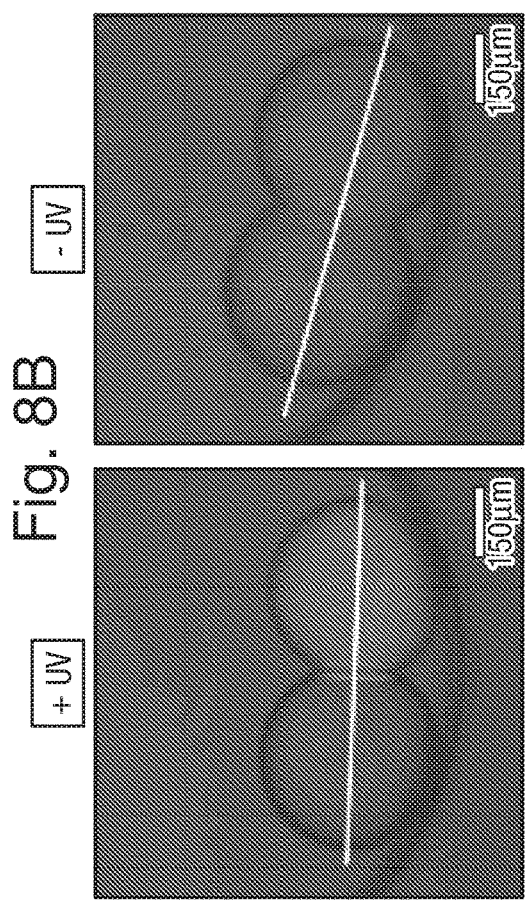
FIG. 8 shows light-activated expression from LA-αHL-GFP DNA in a pair of synthetic cells forming a DIB. (A) Schematic of the synthetic cell pair. One cell contains LA-αHL-GFP DNA, the other contains no DNA. The αHL-GFP fusion protein pore protein will localise to the bilayer when expressed. (B) When LA-αHL-GFP DNA activated in a synthetic cell neighboring another containing no DNA the αHL-GFP fusion membrane pore protein locates to the bilayer. No expression is observed without light activation. (C) Fluorescence intensity line profile of B. Top line is +UV and bottom line is −UV. (D) Rotated 3D projection of a z-stack of αHL-GFP DNA, as expressed in B, demonstrates that αHL-GFP becomes located throughout the flat interface bilayer.
Figure 8D:
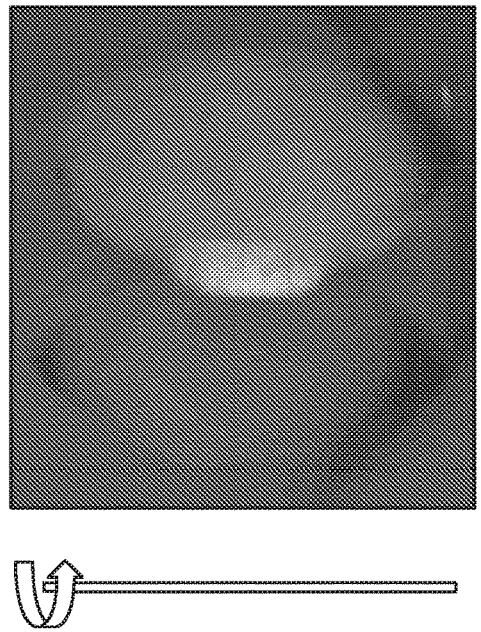
Figure 8A:
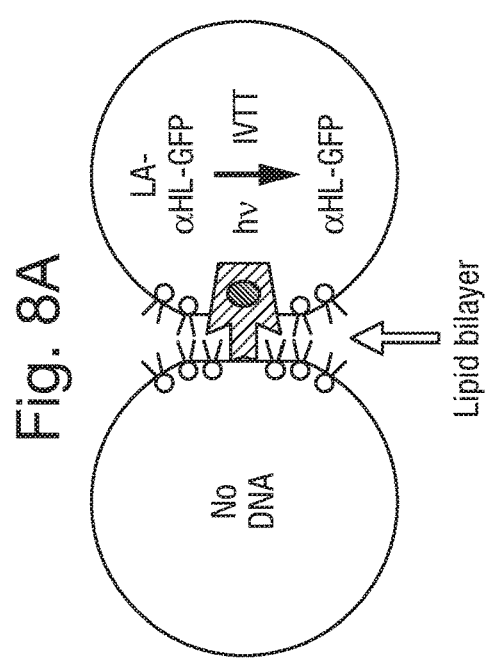
Figure 8C:
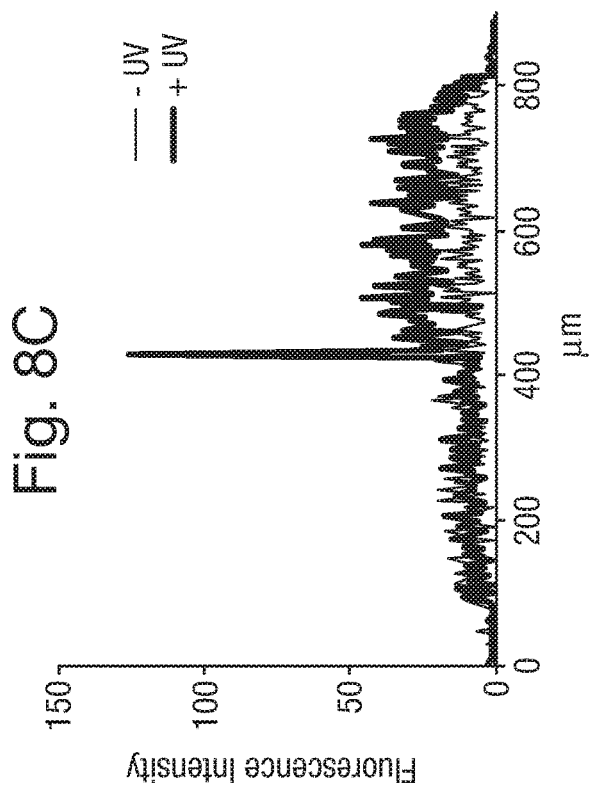

A hydrogel network may further comprise one or more hydrogel objects which do not have an outer layer of amphipathic molecules. For instance it may further comprise a hydrogel object which consists only of a hydrogel body. The further hydrogel object may not be in contact with the plurality of hydrogel objects. The further hydrogel object may be set apart from the plurality of hydrogel objects and thus may be a "stand-alone" hydrogel object. An example of a further hydrogel object set apart from the plurality of hydrogel objects is shown e.g. in FIG. 7c of WO 2014/064459. A further hydrogel object, together with the plurality of hydrogel objects may thus, for instance, be used to form a switch or as part of a switch. Alternatively, the further hydrogel object(s) may be in contact with the plurality of hydrogel objects. For instance, the further hydrogel objects may be surrounded by hydrogel objects of the hydrogel network, such that each surface of the further hydrogel object is in contact with a hydrogel object of the hydrogel network and each interface that the further hydrogel object forms with the hydrogel objects of the hydrogel network is an interface that does not comprise a bilayer of amphipathic molecules.

Independently of whether or not an interface comprises a bilayer of the amphipathic molecules, the area of the interface between the contacting hydrogel objects will typically depend upon the shapes of the hydrogel bodies at said interface. Thus, if the interface is formed between the flat faces of two different hydrogel objects, the area will usually be larger than if the interface is formed between a hydrogel object that is a sphere and a flat surface of another hydrogel object.

Typically, in a hydrogel network in accordance with the invention, said plurality of hydrogel objects comprises a first hydrogel object and a second hydrogel object, wherein each of the first and second hydrogel objects comprises a hydrogel body, and an outer layer of amphipathic molecules, on at least part of the surface of the hydrogel body, wherein the first hydrogel object contacts the second hydrogel object to form a said interface between the first and second objects. When the hydrogel network comprises three or more hydrogel objects, subject to the condition that the first hydrogel object contacts the second hydrogel object, the first and second hydrogel objects may be anywhere within the hydrogel network.

In some embodiments, the interface between the first and second objects comprises a bilayer of the amphipathic molecules. The bilayer separates the two hydrogel objects such that they are not in direct contact with each other at the interface.

Alternatively, the interface between the first and second objects may not comprise a bilayer of amphipathic molecules. The hydrogel bodies of the first and second objects may, for instance, be in direct contact with each other at the interface between them. Alternatively, the interface may, for instance, comprise a thin layer of a hydrophobic or hydrophilic medium, or another polymer, between the two hydrogel objects.

When the interface between the first and second objects does not comprise a bilayer of amphipathic molecules the first object or the second object may, for instance, be a Janus particle. As discussed above, the amphipathic molecules on the surface of the hydrophobic material of the Janus particle are not able to form a bilayer of amphipathic molecules.

In some embodiments, the hydrogel body of the first hydrogel object is in direct contact with the hydrogel body of the second object, at the interface between the first and second objects.

Usually, in a hydrogel network in accordance with the invention, said plurality of hydrogel objects further comprises a third hydrogel object, wherein the third hydrogel object comprises a hydrogel body, and an outer layer of amphipathic molecules, on at least part of the surface of the hydrogel body, wherein the first or second hydrogel object contacts the third hydrogel object to form a said interface between the contacting hydrogel objects, between the first or second hydrogel object and the third hydrogel object.

Typically, the first hydrogel object contacts the third hydrogel object to form a said interface between the first and third hydrogel objects, and wherein the second hydrogel object contacts the third hydrogel object to form a said interface between the second and third hydrogel objects.

Thus, in some embodiments, the network comprises three or more of said hydrogel objects, and a plurality of said interfaces between contacting hydrogel objects.

As mentioned above, the hydrogel network may comprise one interface, or it may comprise two or more interfaces. Typically, the hydrogel network comprises at least n of said hydrogel objects, and at least n−1 of said interfaces between contacting hydrogel objects, wherein n is equal to or greater than 2. The integer n may be equal to or greater than 3. More typically, n is equal to or greater than 4.

The hydrogel network may be a three-dimensional network.

In some embodiments, when the hydrogel network comprises at least n of said hydrogel objects, the network may comprise n or more than n interfaces, wherein n is as herein defined, it being understood that two hydrogel objects may in some embodiments share more than one interface, and that any one hydrogel object can be in contact with (and therefore form an interface with) more than one other hydrogel object.

The integer n can in principle be very high, for instance in the order of millions. This is because the hydrogel bodies may be very small and there is no upper limit on the size of the hydrogel network. Such networks, which can in principle comprise millions of hydrogel bodies, may, for instance, be useful for preparing prototissue (i.e. an aggregate of protocells, also known as minimal tissue). In some embodiments, therefore, the integer n may be as high as several million, for instance up to about 10,000,000, or for instance up to about 5,000,000.

In other embodiments, n may be several hundred, for instance up to about 500, or for instance up to about 400. The integer n may for instance be an integer of from 2 to 500, or an integer of from 3 to 500. n may be an integer of from 2 to 400. In other embodiments, n may be an integer of from 2 to 300, or an integer of from 3 to 200. More typically n is from 2 to 200. In other embodiments, however, n is an integer of from 2 to 50, or an integer of from 3 to 50. n may for instance be from 2 to 20, or from 2 to 10.

In some embodiments, at least one of the interfaces between contacting hydrogel objects comprises a bilayer of amphipathic molecules. Typically, at least two of the interfaces between contacting hydrogel objects comprise a bilayer of amphipathic molecules.

In one embodiment, each of the interfaces between contacting hydrogel objects comprises a bilayer of amphipathic molecules.

Alternatively, in some embodiments, e.g. hydrogel embodiments, at least one of the interfaces between contacting hydrogel objects does not comprise a bilayer of amphipathic molecules. This may be achieved, for example, by displacement of an existing bilayer at the interface of the contacting hydrogel objects. Usually, at least two of the interfaces between contacting hydrogel objects does not comprise a bilayer of amphipathic molecules. In some embodiments, at least half of the interfaces between contacting hydrogel objects do not comprise a bilayer of amphipathic molecules. When, in the hydrogel networks in accordance with the invention as described herein, an interface between contacting hydrogel objects does not comprise a bilayer of amphipathic molecules, the hydrogel bodies of the hydrogel objects may be in direct contact with each other at the interface or the interface may comprise a layer of a material or a compound other than a bilayer of amphipathic molecules, such as a thin layer of a hydrophobic or hydrophilic medium, or another polymer, between the two hydrogel objects. The hydrophobic medium may be as further defined herein.

Thus, in some embodiments, the hydrogel body of one hydrogel object is in direct contact with the hydrogel body of another hydrogel object at at least one of said interfaces between contacting hydrogel objects.

For instance, at at least two of said interfaces between contacting hydrogel objects, the hydrogel body of a hydrogel object may be in direct contact with the hydrogel body of another hydrogel object.

In some embodiments, none of the interfaces between contacting hydrogel objects comprise a bilayer of amphipathic molecules. In these embodiments, the hydrogel bodies of the hydrogel object may be in direct contact with one another or the interface may comprise a thin layer of some other material or compound, for example a thin layer of a hydrophobic medium such as an oil. The hydrophobic medium or oil may be as further defined herein.

Thus, in some embodiments, at each of the interfaces between contacting hydrogel objects, the hydrogel body of one said hydrogel object may be in direct contact with the hydrogel body of another said hydrogel objects.

In some instances, it may be advantageous for all of the interfaces between contacting hydrogel objects in the hydrogel network of the invention to comprise a bilayer of amphipathic molecules. A bilayer can act as a barrier to prevent diffusion of substances from one hydrogel body to the next hydrogel body, and can advantageously therefore help to contain or "store" particular chemicals within particular hydrogel bodies. On the other hand, the bilayers may be modified to allow the network to be functionalised in a variety of ways. For example, a membrane protein may be inserted into the bilayer enabling the flow of information across a network. Alternatively, it may be advantageous for none of the interfaces between contacting hydrogel objects to comprise a bilayer of amphipathic molecules. The absence of a bilayer provides advantages such as improved (faster) transport of ions through the network. There may also be instances for which it may be advantageous for the hydrogel network to comprise at least one interface comprising a bilayer of amphipathic molecules and at least one interface that does not comprise a bilayer of amphipathic molecules. Such systems are particularly advantageous because they can provide a combination of the advantages mentioned above for systems with, and systems without, bilayers. Networks in which some of the interfaces comprise bilayers and others do not can be particularly useful as electrochemical circuits, as described in the Examples, and in synthetic biology.

Accordingly, in some embodiments, at least one of the interfaces between contacting hydrogel objects comprises a bilayer of amphipathic molecules, and at least one other of the interfaces between contacting hydrogel objects does not comprise a bilayer of amphipathic molecules. In some embodiments, two or more of the interfaces between contacting hydrogel objects comprise a bilayer of amphipathic molecules, and/or two or more of the other interfaces between contacting hydrogel objects do not comprise a bilayer of amphipathic molecules.

For instance, in a hydrogel network in accordance with the invention, at least one of the interfaces between contacting hydrogel objects may comprise a bilayer of amphipathic molecules, and, at at least one other of the interfaces between contacting hydrogel objects, the hydrogel body of one hydrogel object may be in direct contact with the hydrogel body of another hydrogel object. In some embodiments, two or more of the interfaces between contacting hydrogel objects comprise a bilayer of amphipathic molecules, and/or at two or more of the other interfaces between contacting hydrogel objects, the hydrogel bodies at those interfaces are in direct contact with each other.

In hydrogel networks in accordance with the invention, the plurality of hydrogel objects is typically surrounded by a layer of the amphipathic molecules.

The layer of amphipathic molecules surrounding the plurality of hydrogel objects is usually made up of the outer layers of amphipathic molecules of the hydrogel objects in the network. The outer layers of amphipathic molecules may comprise one type of amphipathic molecule or may comprise two or more different types of amphipathic molecules. Thus the layer of amphipathic molecules surrounding the plurality of hydrogel objects may comprise one type of amphipathic molecule or may comprise two or more different types of amphipathic molecules.

In some embodiments of the hydrogel network of the invention, one or more of the hydrogel objects comprises: (a) said hydrogel body, and (b) said outer layer of amphipathic molecules around at least part of the surface of the hydrogel body, wherein the outer layer of amphipathic molecules covers at least 50% of the area of the surface of the hydrogel body.

The outer layer of amphipathic molecules of a hydrogel object does not necessarily cover the whole of the surface of the hydrogel body. For instance, when the hydrogel body of one hydrogel object is in direct contact with the hydrogel body of another hydrogel object, there will be no outer layer of amphipathic molecules that covers the entire surface of either hydrogel body. This is because no such outer layer of amphipathic molecules will be present at the interface between the contacting hydrogel bodies. Similarly, when two hydrogel bodies are pushed together so as to squeeze out the bilayer of amphipathic molecules between them, there may be no amphipathic molecules present at the interface between the objects, and therefore the outer layer of amphipathic molecules will not cover the entire surface of either hydrogel body. Thus, the portion of the surface area of the hydrogel body that is covered by an outer layer of amphipathic molecules may be dictated by the interface(s) which the hydrogel object forms with other hydrogel objects in the network, and by other factors such as the shape of the hydrogel bodies.

Typically, each hydrogel object in the hydrogel network comprises: (a) said hydrogel body, and (b) said outer layer of amphipathic molecules around at least part of the surface of the hydrogel body, wherein the outer layer of amphipathic molecules covers at least 50% of the area of the surface of the hydrogel body.

In some embodiments, one or more of the hydrogel objects in the hydrogel network comprises: (a) said hydrogel body, and (b) said outer layer of amphipathic molecules around the whole of the surface of the hydrogel body. For instance, in a hydrogel network in which all of the hydrogel objects are in contact with each other to form bilayers at the interfaces, typically all of those hydrogel objects will comprise an outer layer of amphipathic molecules around the whole of the surface of the hydrogel body.

Thus, in some embodiments, all of the hydrogel objects in the hydrogel network comprise: (a) said hydrogel body, and (b) said outer layer of amphipathic molecules around the whole of the surface of the hydrogel body.

If, for instance, the only interfaces in the network are interfaces comprising a bilayer of amphipathic molecules, then the hydrogel bodies of the hydrogel objects in the network will typically comprise a said outer layer of amphipathic molecules around the whole of the surface of the hydrogel body. Thus, in a hydrogel network in which all of said interfaces comprise a bilayer of amphipathic molecules, usually all of the hydrogel objects in the hydrogel network comprise said hydrogel body, and said outer layer of amphipathic molecules around the whole of the surface of the hydrogel body.

Usually, in a hydrogel network in accordance with the invention, the hydrogel body of at least one of said hydrogel objects is molded. Typically, the hydrogel body of two or more of said hydrogel objects are molded, for instance, at least three may be molded. In some embodiments, at least half of the hydrogel bodies are molded. For instance, all of the hydrogel bodies may be molded.

If a hydrogel body is molded, it may be molded by any suitable method. Typically, a template will be used to produce the molded hydrogel body. For instance, a PMMA (poly(methyl methacrylate)) mold may be used.

Typically, the hydrogel body of at least one of said hydrogel objects is a molded three-dimensional hydrogel shape. Usually, two or more of said hydrogel bodies are molded three-dimensional hydrogel shapes. For instance at least three of said hydrogel bodies may be molded three-dimensional hydrogel shapes. In some embodiments, at least half of the hydrogel bodies are molded three-dimensional hydrogel shapes. For instance, the hydrogel body of each of said hydrogel objects may be a three-dimensional hydrogel shape.

The hydrogel body may be as herein defined.

As mentioned above, the hydrogel body may be any three-dimensional shape. Typically, the three-dimensional shape is spherical, cross-shaped, cuboid, crescent-shaped, prism-shaped, cylindrical, wire-shaped or a shape which has a triangular, pentagonal, hexagonal, square or rectangular face.

The assembly of hydrogel objects in the hydrogel network may be controlled by any suitable methods. Shape, surface energy or molecular recognition may be used to control the assembly. Additionally or alternatively, the assembly of hydrogel objects in the hydrogel network may, for instance, be controlled by the use of stimuli such as temperature, pH, light, chemicals, ions, and magnetic and electrical fields, by the use of surfaces with switchable properties, or by manual manipulation.

The hydrogel bodies in the network may be any suitable combination of shapes. Further, the arrangement of hydrogel objects in the network can be arranged and/or rearranged to control the assembly of hydrogel objects. For example, the arrangement may be manipulated, for instance manually manipulated. If the arrangement is manipulated manually, a needle, for instance a steel needle, is typically used.

In some embodiments, hydrogel body of at least one of said hydrogel objects is in the shape of a wire. For instance, two or more of said hydrogel objects are in the shape of a wire. In some embodiments at least half of the hydrogel bodies are in the shape of a wire, for instance, all of the hydrogel bodies may be in the shape of a wire.

The wire-shaped hydrogel object may, in some embodiments, have a diameter of less than or equal to 10 mm, for instance, less than or equal to 5 mm. For instance, the wire-shaped hydrogel object may have a diameter of from 0.005 mm to 2 mm, for instance from 0.5 mm to 2 mm. For instance, the wire-shaped hydrogel object may have a diameter of about 0.5 mm. Alternatively, it may have a diameter of from about 1 mm to about 2 mm.

In some embodiments, the wire-shaped hydrogel object will have a length of equal to or greater than 0.5 mm, for instance, equal to or greater than 2 mm. The length of the wire-shaped hydrogel object is usually its largest dimension. The largest dimension is usually as defined herein below.

The diameter of a wire shaped hydrogel object will usually be less than the length of that hydrogel object. Typically, of course, it will be substantially less, for instance, less than a quarter of the length of the hydrogel object, or less than a tenth of the length of the hydrogel object.

As mentioned above, a hydrogel body may be any shape. A hydrogel body may also be any suitable size. Different hydrogel bodies in the hydrogel network may be the same size or a variety of different sizes. Typically, at least one of the hydrogel bodies has a diameter of less than or equal to 50 mm.

When the hydrogel object is a sphere, the diameter of the hydrogel object is the diameter of the sphere. When the hydrogel object is a cylindrical, the diameter is equal to the diameter of either of the circular faces of the cylinder. When the hydrogel object is a wire-shape, the diameter is equal to the diameter of the cross-section of the wire-shape, wherein the cross-section is taken at right angles to the length of the wire-shape. When the hydrogel object is a shape other than a sphere, cylinder or wire-shape the diameter of the hydrogel object is the diameter of a sphere that has the same volume as the hydrogel object.

In some embodiments, at least one of the hydrogel bodies has a diameter of less than or equal to 20 mm, preferably less than or equal to 5 mm. Typically, at least one of the hydrogel bodies has a diameter of from 0.1 mm to 50 mm, for instance, 0.5 mm to 20 mm. Usually, two or more of the hydrogel bodies have a diameter of less than or equal to 20 mm, preferably less than or equal to 5 mm. Typically, two or more of the hydrogel bodies have a diameter of from 0.1 mm to 50 mm, for instance, 0.5 mm to 20 mm. For instance, at least half of the hydrogel bodies may have a diameter of less than or equal to 20 mm, preferably less than or equal to 5 mm. Typically, at least half of the hydrogel bodies have a diameter of from 0.1 mm to 50 mm, for instance, 0.5 mm to 20 mm. In some embodiments, each of the hydrogel bodies has a diameter of less than or equal to 20 mm, preferably less than or equal to 5 mm. Typically, each of the hydrogel bodies have a diameter of from 0.1 mm to 50 mm, for instance, 0.5 mm to 20 mm.

In some embodiments, the largest dimension of at least one of the hydrogel bodies is less than or equal to 100 mm, for instance, less than or equal to 50 mm. Usually, the largest dimension of at least one of the hydrogel bodies is less than or equal to 25 mm, for instance, less than 5 mm. The largest dimension of at least one of the hydrogel bodies may, for instance, be from 0.1 to 100 mm. Usually, the largest dimension of at least one of the hydrogel bodies is from 0.5 to 50 mm, for instance, from 0.5 to 25 mm. The largest dimension of at least one of the hydrogel bodies may, for example, be from 0.5 to 5 mm. For example, when the hydrogel network comprises at least one wire-shaped hydrogel body, the largest dimension of the wire-shaped hydrogel body (or bodies) in the network may be as defined above. In the case of a wire-shaped hydrogel body, the largest dimension will typically be the length of the wire shape when placed in a straight line. Similarly, the largest dimension of a cylindrical hydrogel body will usually be the length of the cylinder i.e. the distance between the two circular faces of the cylinder. In some embodiments, the largest dimension of two or more or the hydrogel bodies present in the network is the largest dimension as defined above. For instance, the largest dimension of at least half of the hydrogel bodies in the network may be as define above. In some embodiments, the largest dimension of each and every one of the hydrogel bodies in the hydrogel network is as defined above.

When the hydrogel body is shaped other than wire-shaped, the volume of the hydrogel body is typically at least 0.001 $mm^3$, for instance at least 0.005 $mm^3$. More typically, the volume of the hydrogel body is typically at least 0.008 $mm^3$. The hydrogel body usually has dimensions (length, width and height) of at least 0.1 mm×at least 0.1 mm×at least 0.1 mm. For instance, the hydrogel body may have dimensions of at least 0.175 mm (length)×at least 0.175 mm (width)×at least 0.175 mm (height), for instance, dimensions of at least 0.2 mm (length)×at least 0.2 mm (width)×at least 0.2 mm (height).

Typically, the hydrogel body comprises a hydrogel comprising agarose. Thus, typically, the hydrogel comprises said agarose and water. The concentration of the agarose in the water is usually less than or equal to 10% w/v agarose. For instance the concentration of the agarose may be less than or equal to 5% w/v agarose. Usually, the concentration of the agarose in the water is about 1% w/v agarose.

Hydrogels other than agarose can also be used. For instance the hydrogel body may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the hydrogel body may comprise a silicone hydrogel or LB (Luria broth) agar.

Individual hydrogel bodies in the hydrogel network may comprise the same hydrogel or different hydrogels. Thus the hydrogel of each hydrogel body in the hydrogel network may be the same or different.

Usually, the concentration of the agarose in said water is from 0.25 to 5% w/v agarose. For instance, the concentration of the agarose in said water may be from 0.5 to 2% w/v agarose.

The agarose may, for instance, be a low melt agarose.

In some embodiments, at least one of said plurality of hydrogel objects of the hydrogel network of the invention is a Janus particle comprising: (a) a hydrogel body comprising a hydrophilic material and a hydrophobic material, and (b) an outer layer of amphipathic molecules, on at least part of the surface of the hydrogel body.

The hydrophilic material of the Janus particle may, for instance, comprise agarose. For example, hydrophilic material of the Janus particle may comprise agarose and water. The concentration of the agarose in the water may be less than or equal to 10% w/v agarose. For instance, the concentration of the agarose may be less than or equal to 5% w/v agarose. The concentration of the agarose in the water may, for instance, be about 1% w/v agarose.

Typically, when the hydrogel network of the invention comprises a Janus particle, the outer layer of amphipathic molecules, on at least part of the surface of the hydrogel body, is an outer layer on the hydrophilic material of the hydrogel body.

The Janus particle may be any shape. The hydrogel body of the Janus particle may, for instance, be any regular or irregular shape, or any polygon. When the hydrogel body is a polygon, it may be convex or non-convex. The hydrogel body of the Janus particle may, for instance, be a molded three-dimensional hydrogel shape. Typically, the three-dimensional shape is spherical, cross-shaped, cuboid, crescent-shaped, prism-shaped, cylindrical, wire-shaped or a shape which has a triangular, pentagonal, hexagonal, square or rectangular face.

The hydrogel body comprising a hydrophilic material and a hydrophobic material may, for example, be a spherical hydrogel body made up of a hemisphere of a hydrophilic material and a hemisphere of a hydrophobic material. Alternatively, the hydrophobic material may be in the centre of the Janus particle, and surrounded by the hydrophilic material. However, any suitable arrangement of at least one hydrophilic material and at least one hydrophobic material may be used. The Janus particle may, for instance, comprise a first hydrophilic material, a hydrophobic material and a second hydrophilic material, wherein (i) the first and second hydrophilic materials may be the same or different; and (ii) the first and second hydrophilic materials are not in contact with each other. Similarly, the Janus particle may, for instance, comprise a first hydrophobic material, a hydrophilic material and a second hydrophobic material, wherein (i) the first and second hydrophobic materials may be the same or different; and (ii) the first and second hydrophobic materials are not in contact with each other.

The Janus particle thus allows compartments to be formed within the hydrogel body. Individual compartments may, for instance, be used as a store for a small molecule, such as a dye or a magnet, a sensor molecule, a therapeutic agent or a diagnostic agent. This may, for example, permit a concentration gradient to form within the hydrogel body. If a concentration gradient were to form, this may lead to the diffusion of small molecules, such as dyes or magnets, sensor molecules, therapeutic agents or diagnostic agents to diffuse from one compartment within the Janus particle to another compartment within the Janus particle.

In one embodiment, when the hydrogel network comprises a Janus particle, the hydrophilic material is on one side of the hydrogel body and the hydrophobic material is on the other side of the hydrogel body.

The hydrogel network may comprise two or more Janus particles. Thus, the hydrogel network may comprise two or more hydrogel objects comprising: (a) a hydrogel body comprising a hydrophilic material and a hydrophobic material, and (b) an outer layer of amphipathic molecules, on at least part of the surface of the hydrogel body. For instance, the hydrogel network may comprise two, three or four hydrogel objects comprising: (a) a hydrogel body comprising a hydrophilic material and a hydrophobic material, and (b) an outer layer of amphipathic molecules, on at least part of the surface of the hydrogel body.

As mentioned above, the hydrogel body may comprise agarose. In some embodiments, the agarose may, for instance, be dissolved in a buffer solution. The hydrogel body may be freely chosen for the purpose or use of the hydrogel network, or for the experiment to be performed using the hydrogel network. The hydrogel of each hydrogel body in the hydrogel network may be the same or different. One important property is pH and this can be varied over a wide range. In some embodiments, for instance, the pH of the aqueous medium within the hydrogel objects may be in the range of from 3 to 9 (or for instance in the range of from 5 to 9) although higher and lower pHs are also possible. In one embodiment, the pH of the aqueous medium within the hydrogel objects may be in the range of from 6 to 8. The hydrogel body may therefore comprise an aqueous buffer solution. Any suitable buffer can be employed, depending on the desired pH. The buffer solution may for instance comprise Tris HCl, with KCl. In some embodiments the pH of the aqueous buffer solution is from 3 to 9, or for instance from 5 to 9. In some embodiments the pH of the aqueous buffer solution is from 6 to 8. The nature and concentration of the solutes can be varied to vary the properties of the solution. As noted previously, where the hydrogel body may support the promoters, expression systems and/or vectors of the invention, the skilled person will readily adjust the pH accordingly.

In some embodiments, the hydrogel network further comprises one or more further hydrogel objects, which further hydrogel objects comprise a hydrogel body.

Such a further hydrogel object does not necessarily comprise an outer layer of amphipathic molecules. Also, a further hydrogel object may or may not be in contact with any of the other hydrogel objects in the hydrogel network. A further hydrogel object may, for instance, be in contact with at least one of the other hydrogel objects in the hydrogel network but not in contact with any amphipathic molecules. This situation may arise, for example, if the further hydrogel object is surrounded by other hydrogel objects, and the interfaces between further hydrogel objects and the other objects do not comprise any amphipathic molecules. For example, the network may comprise a cube of 27 spherical hydrogel objects (three 3×3 layers) with the "further hydrogel object" occupying the central position, and the interface between the further hydrogel object and the other hydrogel objects may not comprise any layer of amphipathic molecules.

Alternatively, the "further hydrogel object" may be a "stand alone" hydrogel object which is not actually in contact with any of the other hydrogel objects in the network. See for instance, FIG. 7 b-e of WO2014064459, in which such a "stand alone" object is present.

Techniques such as soft lithography can be used to produce aqueous objects such as droplets and hydrogel objects having particularly small dimensions.

Very small aqueous objects may, for instance, be produced by disposing, for example, aqueous fluids, or liquid or melted hydrogel, from a syringe or needle.

The aqueous object or aqueous object networks or assemblies described herein may form part of an encapsulate, for instance a droplet encapsulate. Such an encapsulate, e.g. a droplet encapsulate, may be referred to as a "multisome". The encapsulate generally comprises: a volume (such as a drop) of a hydrophobic medium; a peripheral layer of amphipathic molecules around the surface of the volume of hydrophobic medium; and an aqueous object (e.g. droplet or hydrogel object), aqueous object network or assembly within the peripheral layer, wherein the aqueous object, aqueous object network or aqueous object assembly is as defined herein. Typically, the encapsulate is disposed in a bulk hydrophilic medium, and the peripheral layer of amphipathic molecules is at the interface between the bulk hydrophilic medium the hydrophilic medium. In some embodiments the droplet, or at least one of the droplets in the droplet assembly, comprises a magnetic material. The amphipathic molecules which form the peripheral layer of the encapsulate may, for instance, be provided in the hydrophobic medium or in the bulk hydrophilic medium.

The encapsulate, or "multisome", may, for example, communicate with the external environment through membrane proteins in the peripheral layer. In addition, membrane proteins may allow structures such as droplets or hydrogel objects within the same multisome to communicate with each other. This in principle allows multisomes to sense their environment, process information, and contingently deliver materials to the surroundings. The encapsulates may be produced by the methods described in GB patent application number 1119032.9 and U.S. patent application No. 61/592,062. The disclosures in GB 1119032.9 and U.S. 61/592,062 are incorporated herein by reference.

Processes in accordance with the invention may, for instance, be used to bring an aqueous object, such as a droplet, into contact with another aqueous object, such as another droplet. Typically, the other structure comprises (a) an aqueous medium and (b) an outer layer of amphipathic molecules around the surface of the aqueous medium. In some embodiments, the other structure may further comprise a magnetic material disposed in the aqueous medium. Typically, the magnetic material disposed in the aqueous medium of the droplet(s) comprises a paramagnetic or a superparamagnetic material, or a paramagnetic or a superparamagnetic metal, such as iron. In some embodiments, the magnetic material disposed in the aqueous medium of the aqueous object(s) comprises a magnetic bead. The magnetic bead may, for instance, comprise magnetic particles. Usually, the magnetic material disposed in the aqueous medium of the aqueous object(s) comprises a biocompatible magnetic material, such as a biocompatible magnetic bead. Any suitable magnetic bead may be used. For instance, magnetic beads commercially available from, for instance, Clontech, Promega, Invitrogen and NEB, may be used.

The boundary that is shared between contacting aqueous objects, such as droplets, at the point of contact between the objects, is referred to herein as an interface. An interface is formed when part of the outer layer of an aqueous object contacts part of the outer layer of another aqueous object. When the aqueous object is brought into contact with the other aqueous object, a bilayer of amphipathic molecules will quickly from at the interface between the two objects. The bilayer comprises amphipathic molecules from the outer layer of amphipathic molecules around the surface of the aqueous medium of each aqueous object at the interface. The bilayer forms as it is an energetically more favourable configuration for the amphipathic molecules to adopt. The shape of the bilayer formed will be the shape with the lowest free surface energy.

The aqueous medium of the other aqueous object is typically an aqueous medium as defined herein.

The amphipathic molecules of the other aqueous object are usually amphipathic molecules as defined herein.

Typically, when the aqueous object is brought into contact with another aqueous object, a bilayer of amphipathic molecules is formed at an interface between each of the contacting aqueous objects. Once at the second location the aqueous object may therefore be in contact with another aqueous object and an aqueous object assembly comprising two aqueous objects has been formed.

In some embodiments, the other aqueous object may be in contact with one or more further aqueous objects. There may, for instance, be a bilayer of amphipathic molecules at each interface between each of the contacting aqueous objects.

At least one of said bilayers disposed between aqueous objects, such as droplets or hydrogel objects, may further comprise a membrane protein. The membrane protein may be of any type. The use of integral membrane proteins has been demonstrated, but it is equally expected that peripheral membrane proteins could be used. The membrane protein may for instance be a membrane pump, channel and/or pore, to allow for precise control over the exchange of material, and electrical communication, between the aqueous objects in an aqueous object network or assembly. When the aqueous object assembly forms part of an encapsulate, the membrane protein allows for precise control over the exchange of material, and electrical communication, between the assembly and an external solution. The membrane protein could for instance be an αHL pore. However, any suitable membrane protein can be used including the two major classes that is β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction. The bilayer at an interface between contacting aqueous objects, may comprise more than one membrane protein. For instance, a particular bilayer may contain multiple copies of the same membrane protein, or two or more different classes of membrane proteins. Where more than one class is present, the bilayer may contain multiple copies of each different class.

Suitable membrane proteins which allow for exchange of materials and electrical communication are known and readily available to the skilled person; many such proteins are either commercially available or can be prepared by known methods. For instance, WT αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al. Method. Enzymol. 475, 591-623, 2010). Also, Bayley, H. et al. Droplet interface bilayers. Mol. BioSyst. 4, 1191-1208 (2008) lists several proteins that were tested for insertion into droplet interface bilayers made in bulk oil.

When a bilayer comprises a membrane protein, said bilayer might comprise two or more membrane proteins. The membrane proteins may be the same or different. The number of membrane proteins in a bilayer may be determined by analysing the conductivity within an aqueous object assembly.

When there are two or more bilayers, each bilayer may further comprise a membrane protein, wherein each of said membrane proteins is as herein defined. For instance, each bilayer may further comprise a membrane protein, wherein each of said membrane proteins is as herein defined.

Aqueous objects can exchange chemical species with each other through membrane proteins incorporated in the bilayer between the objects. Suitable membrane proteins include, but are not limited to, pumps, channels and/or pores, receptor proteins, transporter proteins, for instance an α-hemolysin (αHL) pore. Thus, an aqueous object assembly may be capable of trafficking materials such as chemical compounds through the network, from object to object, as well as to and from the external environment. Complex transport systems can be built up in this way. The transport system comprises an aqueous object assembly such as a droplet assembly.

A aqueous object assembly may, for instance, act as a sensor module, capable of sensing the presence of a particular chemical in the external environment, for instance, or capable of sensing light. Thus, the aqueous object may comprise a sensor molecule. The sensor molecule can be present in the aqueous medium of the aqueous objector in the bilayer. In the case of a hydrogel object, the sensor molecule can be present in the hydrogel body. The sensor molecule may be a molecule which is sensitive to the presence of a particular chemical (for instance a target analyte), or it may be a light-sensitive molecule.

Usually, the concentration of membrane proteins is equal to or greater than 10 ng mL$^{-1}$. For instance, the concentration of membrane proteins is equal to or greater than 50 ng mL$^{-1}$. Typically, the concentration of membrane proteins is from 10 ng mL$^{-1}$ to 2000 μg mL$^{-1}$, for instance from 50 ng mL$^{-1}$ to 1000 μg mL$^{-1}$. More typically, the concentration of membrane proteins is from 75 ng mL$^{-1}$ to 900 μg mL$^{-1}$, for instance from 80 ng mL$^{-1}$ to 85 μg mL$^{-1}$. In some embodiments, the concentration of membrane proteins is about 83 μg mL$^{-1}$. In other embodiments, the concentration of membrane proteins is about 830 ng mL$^{-1}$. In a further embodiment, the concentration of membrane proteins is about 83 ng mL$^{-1}$.

Typically, the concentration of membrane proteins is the concentration of membrane proteins in the aqueous medium of the aqueous object, when the aqueous object is formed. When an aqueous object, such as a droplet comprising a membrane protein is contacted with another droplet (which may or may not comprise a membrane protein), a bilayer of amphipathic molecules if formed at the interface. That bilayer typically comprises a membrane protein. Therefore a membrane protein initially in the aqueous medium may move to the bilayer.

When the aqueous object, such as a droplet is in contact with another aqueous object, such as a droplet, the concentration of membrane proteins in the droplet and the other droplet may be the same or different. Further, when the aqueous object is part of an aqueous object assembly, the concentration of membrane proteins in each object of the assembly may be the same or different.

When the membrane protein comprise αHL, at least one of bilayers may comprise a blocker of αHL such as γ-cyclodextrin (γCD).

Typically, the concentration of the blocker of αHL is equal to or greater than 10 for instance equal to or greater than 25 μM. Usually, the concentration of the blocker of αHL is from 10 μM to 50 for instance from 25 μM to 40 μM.

The aqueous object, such as a droplet, may, in some embodiments, comprise other materials, compounds or substances. For instance, the aqueous object may comprise a small molecule, such as a dye, or a magnet. Suitable dyes include, but are not limited to, xylene cyanol FF, orange G, pyranine, fluorescein and 5-cTAMRA (5-carboxytetramethylrhodamine). Alternatively, the aqueous object may comprise a sensor molecule, for instance a sensor molecule that it sensitive to a particular chemical or is a light-sensitive molecule. As a further alternative, the aqueous object may comprise a therapeutic agent, such as a prodrug, or a diagnostic agent, such as a contrast agent.

Wherein the aqueous object comprises a droplet typically, the droplet has a volume of less than or equal to 1500 nL. More typically, the droplet has a volume of from 100 nL to 1500 nL. For instance, the droplet may have a volume of from 300 nL to 900 nL. Usually, the droplet has a volume of from 300 nL to 900 nL for instance, from 400 nL to 800 nL. For instance, the droplet may have a volume of about 400 nL or about 800 nL.

When the droplet is in contact with another droplet, the volume of the droplet and the other droplet may be the same or different. For instance, each droplet may have a volume of less than or equal to 1500 nL. Typically, each droplet has a volume of from 100 nL to 1500 nL. For instance, each droplet may have a volume of from 300 nL to 900 nL. Usually, each droplet has a volume of from 300 nL to 900 nL for instance, from 400 nL to 800 nL. For instance, each droplet may have a volume of about 400 nL or about 800 nL.

If the droplet forms part of a droplet assembly, the droplets in the droplet assembly may be of the same volume or may be of different volumes. Typically, each droplet has a volume of less than or equal to 1500 nL. More typically, each droplet has a volume of from 100 nL to 1500 nL. For instance, each droplet may have a volume of from 300 nL to 900 nL. Usually, each droplet has a volume of from 300 nL to 900 nL for instance, from 400 nL to 800 nL. For instance, each droplet may have a volume of about 400 nL or about 800 nL, preferably from about 50 to about 100 pL.

Aqueous objects as described herein, particularly aqueous droplets and hydrogel objects may be moved relative to each other using magnetic materials. Typically, magnetic materials are disposed in the aqueous medium of aqueous objects and aqueous objects may then be moved using a magnet.

The magnet may be any suitable magnetic material. Usually, the magnetic material is a permanent magnet, for instance, a ferromagnet or a ferrimagnet. Alternatively, the magnet may be an electromagnet.

Typically, the magnet comprises a transition metal, such as nickel, iron or cobalt, or a rare earth metal, such as neodymium or samarium. More typically, the magnet comprises neodymium.

The size of the magnet will depend on a number of factors such as the magnetic material in the droplets and the distance over which a magnetic attraction is required. The magnet may, for instance, have a volume of from 0.5 $mm^3$ to 10 $mm^3$. Typically, the magnet has a volume of from 1 $mm^3$ to 5 $mm^3$, for instance, of from 1 $mm^3$ to 2 $mm^3$. Usually, the magnet is a cube with dimensions of from 1 to 2 mm, for instance a cube with dimensions of approximately 1.2 mm.

Typically, the magnetic material disposed in the aqueous medium of the aqueous object(s), typically droplet(s), comprises a paramagnetic or a superparamagnetic material, for instance a paramagnetic or a superparamagnetic metal, such as iron.

In some embodiments, the magnetic material disposed in the aqueous medium of the object(s)/droplet(s) comprises a magnetic bead. The magnetic bead may, for instance, comprise magnetic particles.

Usually, the magnetic material disposed in the aqueous medium of the object(s)/droplet(s) comprises a biocompatible magnetic material, such as a biocompatible magnetic bead.

Any suitable magnetic bead may be used. For instance, magnetic beads commercially available from, for instance, Clontech, Promega, Invitrogen and NEB, may be used.

In some embodiments, the magnetic bead comprises magnetic particles with an organic group such as a metal-chelating group, such as nitrilotriacetic acid (NTA), attached. The organic component may, for instance, comprise a group selected from —C(=O)O—, —C—O—C—, —C(=O), —NH—, —C(=O)—NH, —C(=O)—$CH_2$—I, —S(=O)$_2$— and —S—. The organic component may comprise a metal chelating group, such as NTA (nitrilotriacetic acid). Usually, a metal such as nickel or cobalt is also attached to the metal-chelating group. Magnetic beads of this sort are commonly used for capturing His-tagged proteins, but are also suitable for use in the process and the produce of the present invention.

Thus, in some embodiments, the magnetic bead may further comprise Ni-NTA or Co-NTA, for instance, a Ni-NTA magnetic bead may be used, or a Co-NTA magnetic bead.

As the skilled person will appreciate, moving the magnet relative to the first location may comprise: (a) moving the magnet towards the object/droplet whilst keeping the object/droplet stationary; (b) moving the object/droplet towards the magnet whilst keeping the magnet stationary; or (c) moving the magnet towards the object/droplet and moving the object/droplet towards the magnet.

The magnet may be positioned and controlled using any suitable method. Typically, the magnet is connected to a rod, for instance, a glass rod.

Moving the droplet typically comprises moving the rod. For instance, the rod may be moved by a micromanipulator.

The movement of the magnet may be automated. For instance, when the magnet is an electromagnet, the movement of the magnet may be automated.

The object/droplet is typically disposed in a hydrophobic medium.

Moving the object/droplet may comprise moving the hydrophobic medium. As the hydrophobic medium is usually contained in a container, this usually comprises moving a container containing the hydrophobic medium. The hydrophobic medium may, for instance, be as defined herein.

In the step of (ii) moving the magnet relative to the first location whilst maintaining said magnetic attraction there must be a magnetic attraction between the object/droplet and the magnet throughout the step. However, the magnitude of the magnetic attraction may vary. For instance, the distance between the object/droplet and the magnet may be reduced, thus increasing the magnetic force. Alternatively, the distance between the object/droplet and the magnet may be increased, thus decreasing the magnetic force.

Typically, the step of (ii) moving the magnet relative to the first location moves the magnet in a direction away from the first location whilst maintaining said magnetic attraction, and thereby causing the object/droplet to move away from said first location and towards a second location. Provided that the magnetic attraction is maintained and the object/droplet is moved away from said first location and towards a second location, the magnet may be moved in any direction away from the first location.

The magnetic material may be any suitable magnetic material. Usually, the magnetic material is a permanent magnet, for instance, a ferromagnet or a ferrimagnet. Typically, the magnet comprises a transition metal, such as nickel, iron or cobalt, or a rare earth metal, such as neodymium or samarium. More typically, the magnet comprises neodymium.

Alternatively, the magnet may be an electromagnet. When the magnet is an electromagnet, the process typically further comprises a step of switching on the electromagnet by allowing a current to flow through the wires of the electromagnet.

As illustrated in e.g. International patent application publication WO2014/064461, the inventors have utilised two broad methods, both of which utilise a droplet, as an example of an aqueous object, comprising a magnetic material disposed in the aqueous medium, to be particularly effective for moving a droplet. The methods have been termed the levitation method and the carrier method. The contents of patent application publication WO2014/064461 is incorporated herein by reference.

The two methods have several overlapping features but there are differences between them.

In the carrier method, a first droplet comprising a magnetic bead is typically attracted to a magnet. The movement of the first droplet is controlled by the relative movement of the magnet. Usually, if the first droplet is brought into contact with a second droplet a bilayer of amphipathic molecules simultaneously forms at the interface of the first and second droplets, which bilayer couples the droplets together. The second droplet does not necessarily comprise a magnetic material. Moving the first droplet also moves the second droplet. The movement of the second droplet may therefore also be controlled by the movement of the magnet, even though the second droplet may not comprise a magnetic material. Once the second droplet has been relocated, it may be decoupled from the droplet comprising the magnetic material. Two or more droplets may be coupled together and moved simultaneously.

Typically, in the levitation method, the droplet may be moved in any direction (e.g. left or right, backwards or forwards, up or down), and the step of (i) exposing a droplet to said magnetic field causes the droplet to move away from said first location and towards the magnet. Typically, each droplet moved using the levitation method comprises a magnetic material.

In some embodiments, the step of (i) exposing a droplet to said magnetic field comprises moving said magnet relative to the droplet which is situated at the first location, in a direction towards the droplet, and thereby causing the droplet to be attracted to said magnet by magnetic attraction. For instance, in both the levitation method and the carrier method the droplet is typically attracted to said magnet by magnetic attraction.

The skilled person will appreciate that the distance between the droplet and the magnet required for there to be a magnetic attraction between them will, of course, depend upon factors such as the size of magnetic field of the magnet and the magnetic material disposed in the aqueous medium of the droplet.

Usually, the levitation method uses the magnetic attraction of the droplet to the magnet to cause the droplet to move away from the first location towards the magnet. Therefore, in some embodiments, in the process of the invention, the step of (i) exposing a droplet to said magnetic field causes the droplet to move away from said first location and towards the magnet.

The magnetic force required to move away from said first location and towards the magnet will, for instance, depend upon the density of the medium through which the droplet is moved and the weight of the droplet. For instance, if the droplet is moved vertically through a medium that has a density of approximately 0.75 times the density of water, a force of approximately 0.25 times the weight of the droplet in air must usually be applied.

Typically, the droplet is disposed in a hydrophobic medium and the magnet is above the hydrophobic medium. When the magnet is a permanent magnet, the magnet is typically above the hydrophobic medium.

Alternatively, the droplet may be disposed in a hydrophobic medium and the magnet may also be in the hydrophobic medium. For instance, when the magnet is an electromagnet, the magnet may be above the hydrophobic medium or in the hydrophobic medium. The hydrophobic medium may, for instance, be as further defined herein.

In some embodiments, the magnetic bead comprises magnetic particles with an organic group such as a metal-chelating group, such as nitrilotriacetic acid (NTA), attached. The organic component may, for instance, comprise a group selected from —C(=O)O—, —C—O—C—, —C(=O), —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as nickel or cobalt is also attached to the metal-chelating group. Magnetic beads of this sort are commonly used for capturing His-tagged proteins, but are also suitable for use in the process and the produce of the present invention. Typically, the magnetic bead may comprises a Ni-NTA or a Co-NTA magnetic bead, for instance, a Ni-NTA magnetic bead.

Accordingly, in the process of the invention, the step of (iii) disposing the droplet at said second location comprises bringing the droplet into contact with another droplet so that a bilayer of amphipathic molecules is formed at an interface between contacting droplets.

The skilled person will appreciate that any of these methods employing magnetic materials may be applied to aqueous structures which are not in the form of droplets.

Usually, the hydrophobic medium is contained by a container. A surface of the container that is in contact with the oil may be a rough surface or a smooth surface.

Typically, the aqueous object/droplet at the first location is disposed on a surface. The surface may be a rough surface or a smooth surface. Whether the surface is a rough surface or a smooth surface typically depends on factors such as whether or not the aqueous object/droplet should be able to move across the surface easily. For instance, in the carrier method, the aqueous object/droplet usually only moves the aqueous object/droplet within a single plane. This will typically mean that the aqueous object/droplet is moved across the bottom surface of the container, in any direction. A smooth surface will facilitate this movement. However, for the levitation method, the step of (i) exposing an aqueous object/droplet to said magnetic field causes the aqueous object/droplet to move away from said first location and towards the magnet. As the aqueous object/droplet is typically not being moved across the surface a smooth surface is not necessarily required. As an alternative to a smooth surface, the inventors have found that a patterned surface may be advantageous. The use of a patterned surface may, for instance, help to position the aqueous object/droplet at a particular location. The use of a patterned surface may also help to maintain the position of other aqueous structures/droplets that are not the aqueous object/droplet originally at the first location. For example, the use of a patterned surface may facilitate the disassembly of an aqueous object/droplet assembly. Such disassembly is discussed below.

Accordingly, the aqueous object/droplet at the first location is disposed on a patterned surface or a smooth surface. A patterned surface is typically a textured surface.

As discussed above, the aqueous object/droplet is usually disposed in a hydrophobic medium, which hydrophobic medium is contained by a container. Therefore, a surface of the container in contact with the aqueous object/droplet is usually a patterned surface or a smooth surface.

The patterned surface may be designed taking into account the dimensions of the aqueous object/droplet and/or other aqueous structures/droplets that may be in contact with the surface. For example, the pattern may be designed to allow an aqueous object/droplet or structures/droplets to rest within a dip in the surface.

The difference in height between the highest and lowest points of the patterned surface is typically equal to or greater than 0.05 mm, for instance equal to or greater than 0.1 mm. Usually, the difference in height between the highest and lowest points of the patterned surface is from 0.05 to 0.5 mm, for instance, from 0.1 to 0.4 mm. The difference in height between the highest and lowest points of the patterned surface may, for instance, be about 0.2 mm.

In some embodiments, the aqueous object/droplet is disposed on a surface comprising a pillar or a well. Typically, the aqueous object/droplet is disposed on a surface comprising two or more pillars or two or more wells.

Typically, the height of the pillar or the depth of the well is equal to or greater than 0.05 mm, for instance equal to or greater than 0.1 mm. Usually, the height of the pillar or the depth of the well from 0.05 to 0.5 mm, for instance, from 0.1 to 0.4 mm. The height of the pillar or the depth of the well may, for instance, be about 0.2 mm.

When the surface comprises two or more pillars, the distance between two pillars may, for instance, be from 0.25 mm to 1.25 mm, for instance from 0.5 mm to 1 mm. Typically, the distance between two pillars is about 0.7 mm. The distance between two pillars is measured from the centre of one pillar to the centre of the other.

When the surface comprises two or more wells, the distance between two wells may, for instance, be from 0.25 mm to 1.25 mm, for instance from 0.5 mm to 1 mm. Usually, distance between two wells is about 0.7 mm. The distance between two wells is measured from the centre of one well to the centre of the other.

The surface may be any suitable surface. For instance, the surface may comprise glass or plastic. Typically, the surface comprises a polymer, such as PDMS (poly(dimethylsiloxane)).

When the surface is a patterned surface, the patterning of the surface may be achieved by any suitable method. For instance, the surface may be etched or milled. Alternatively, the surface may be formed using a template, which template is produced using a process comprising techniques such as etching or milling. Molds may, for instance, comprise a polymer such as PMMA (poly(methyl methacrylate)).

In one embodiment, a PMMA chip is patterned with pillars, which pillars are micromachined on a CNC machine. Usually, the mold is used as a template to mold the surface.

In some embodiments, the step of (i) exposing an aqueous object/droplet to said magnetic field causes the aqueous object/droplet to rise to the top of the hydrophobic medium. Typically, the aqueous object/droplet will rise towards the magnet.

When the hydrophobic medium is in a container, this will mean that the aqueous object/droplet rises towards the top of the container. The depth of the hydrophobic medium may be adjusted so that, when the magnet is moved relative to the aqueous object/droplet, the magnetic field of the magnet is sufficient to attract the aqueous object/droplet and move the aqueous object/droplet away from the first location and towards the magnet. Usually, the field strength is insufficient for the aqueous object/droplet to overcome the surface tension of the hydrophobic medium. The aqueous object/droplet therefore usually remains immersed in the hydrophobic medium.

The movement of the magnet relative to the first location may, for instance, comprise moving the magnet using a micromanipulator.

The movement of the magnet relative to the first location may be automated.

Alternatively, the movement of the magnet relative to the first location may comprise moving the aqueous object/droplet using a micromanipulator. When the aqueous object/droplet is disposed in a hydrophobic medium, which is contained in a container, the movement of the magnet relative to the first location may comprise moving the container using a micromanipulator.

In some embodiments, the step of (ii) moving the magnet relative to the first location moves a single aqueous object/droplet. For instance, both the levitation method and the carrier method may be used to move a single aqueous object/droplet. In these embodiments the step of (i) exposing an aqueous object/droplet which is situated at a first location to a magnetic field of a magnet, causes a single aqueous object/droplet to be attracted to said magnet by magnetic attraction.

Typically, in a process in accordance with the invention, the step of (iii) disposing the aqueous object/droplet at said second location comprises ceasing to expose the aqueous object/droplet to said magnetic field at or near said second location.

For instance, the step of (iii) disposing the aqueous object/droplet at said second location may comprise ceasing to expose the aqueous object/droplet to said magnetic field near said second location and allowing the aqueous object/droplet to arrive at said second location.

The aqueous object/droplet may, for instance, arrive at said second location by falling through the hydrophobic medium under gravity.

As mentioned above, in some embodiments, in a process in accordance with the invention, the step of (i) exposing an aqueous object/droplet to said magnetic field causes the aqueous object/droplet to move away from said first location and towards the magnet. Typically, in these embodiments, the step of (iii) disposing the aqueous object/droplet at said second location comprises ceasing to expose the aqueous object/droplet to said magnetic field at or near said second location. Usually, the step of (iii) disposing the aqueous object/droplet at said second location may comprise ceasing to expose the aqueous object/droplet to said magnetic field near said second location and allowing the aqueous object/droplet to arrive at said second location. For instance, the aqueous object/droplet may arrive at said second location by falling through the hydrophobic medium under gravity.

Usually, the step of ceasing to expose the aqueous object/droplet to said magnetic field comprises moving the magnet away from the aqueous object/droplet. Typically the magnet is a permanent magnet and ceasing to expose the aqueous object/droplet to said magnetic field usually requires the magnet to be moved away from the aqueous object/droplet so that the aqueous object/droplet is no longer attracted to the magnet.

Alternatively, when the magnet is an electromagnet, the step of ceasing to expose the aqueous object/droplet to said magnetic field may comprise switching off the electromagnet. Typically, the electromagnet is switched off by stopping the current from flowing through the wires of the electromagnet.

The aqueous structures may be produced by any suitable method, as exemplified below by reference to droplets. For instance, when the aqueous structure is a droplet the droplet may be produced by injecting or pipetting a composition comprising the aqueous medium into a suitable medium, such as a hydrophobic medium. In some embodiments, the droplet is produced using a microfluidic device. Techniques such as soft-lithography may be used to produce a droplet. A droplet may, for instance, be molded. In some embodiments PMMA molds may be used to produce a droplet. Soft-lithography may, for instance, be used to produce a droplet comprising a hydrogel. Alternatively, a droplet may be produced using photolithograph. A photomask may, for instance, be used to define a pattern through which the light (such as UV light) can pass. Photolithography may, for instance, be used to produce a droplet comprising a photocurable polymer. For instance, photolithography may be used to produce a droplet comprising a hydrogel.

The skilled person will appreciate that methods such as described above are widely applicable and may be used in the manufacture of aqueous structures that are different in form to droplets.

In some embodiments, the aqueous object/droplet at the first location forms a bilayer with another aqueous object/droplet and the step of (i) exposing an aqueous object/droplet to said magnetic field causes the droplet to move away from the other droplet.

As mentioned above, when two aqueous object/droplets are brought together, a bilayer of amphipathic molecules will spontaneously from at the interface between the two objects. When the aqueous object/droplet moves away from the other aqueous object/droplet, both aqueous structures/droplets retain their outer layer of amphipathic molecules on at least part of the surface of the aqueous medium but the bilayer that was present at the interface is not maintained.

Typically, therefore, when the first aqueous object/droplet moves away from the second aqueous object/droplet, the bilayer between the aqueous object/droplet and the other aqueous object/droplet separates.

The other aqueous object/droplet may comprise a magnetic material. Typically, the magnetic material disposed in the aqueous medium of the aqueous object(s)/droplet(s) comprises a paramagnetic or a superparamagnetic material, or a paramagnetic or a superparamagnetic metal, such as iron. In some embodiments, the magnetic material disposed in the aqueous medium of the aqueous object(s)/droplet(s) comprises a magnetic bead. The magnetic bead may, for instance, comprise magnetic particles. Usually, the magnetic material disposed in the aqueous medium of the aqueous object(s)/droplet(s) comprises a biocompatible magnetic material, such as a biocompatible magnetic bead. Any suitable magnetic bead may be used. For instance, magnetic beads commercially available from, for instance, Clontech, Promega, Invitrogen and NEB, may be used.

In some embodiments, the aqueous object/droplet at the first location forms a bilayer with each of two or more other aqueous object(s)/droplets and the step of (i) exposing an aqueous object/droplet to said magnetic field causes the aqueous object/droplet to move away from the other aqueous object/droplets. For instance, the aqueous object/droplet at the first location may form a bilayer with each of two, three or four other aqueous object/droplets and the step of (i) exposing an aqueous object/droplet to said magnetic field causes the aqueous object/droplet to move away from the other aqueous object/droplets.

Usually, when the aqueous object/droplet moves away from the other aqueous object/droplets, each bilayer between the aqueous object/droplet and the other aqueous object/droplets separates.

The other aqueous object/droplets may each independently comprise a magnetic material. The magnetic material may, for instance, be as defined herein.

Typically, the step of (ii) moving the magnet relative to the first location comprises moving the magnet using a micromanipulator.

The movement of the magnet relative to the first location may be automated.

Alternatively, the movement of the magnet relative to the first location may comprise moving the droplet using a micromanipulator. When the aqueous object/droplet is disposed in a hydrophobic medium, which is contained in a container, the movement of the magnet relative to the first location may comprise moving the container using a micromanipulator.

In some embodiments, the step of (ii) moving the magnet relative to the first location moves a single aqueous object/droplet. In these embodiments the step of (i) exposing an aqueous object/droplet which is situated at a first location to a magnetic field of a magnet, causes a single aqueous object/droplet to be attracted to said magnet by magnetic attraction.

Usually, in processes in accordance with the invention, the step of (iii) disposing the aqueous object/droplet at said second location comprises ceasing to expose the aqueous object/droplet to said magnetic field at or near said second location.

For instance, the step of (iii) disposing the aqueous object/droplet at said second location may comprise ceasing to expose the aqueous object/droplet to said magnetic field near said second location and allowing the aqueous object/droplet to arrive at said second location. The aqueous object/droplet may, for instance, arrive at said second location by falling through the hydrophobic medium under gravity.

As mentioned above, in some embodiments, in processes in accordance with the invention, the step of (i) exposing an aqueous object/droplet to said magnetic field causes the aqueous object/droplet to move away from said first location and towards the magnet. Typically, in these embodiments, the step of (iii) disposing the aqueous object/droplet at said second location comprises ceasing to expose the aqueous object/droplet to said magnetic field at or near said second location. Usually, the step of (iii) disposing the aqueous object/droplet at said second location may comprise ceasing to expose the aqueous object/droplet to said magnetic field near said second location and allowing the aqueous object/droplet to arrive at said second location. For instance, the aqueous object/droplet may arrive at said second location by falling through the hydrophobic medium under gravity.

Usually, the step of ceasing to expose the aqueous object/droplet to said magnetic field comprises moving the magnet away from the aqueous object/droplet. Typically the magnet is a permanent magnet and ceasing to expose the aqueous object/droplet to said magnetic field usually requires the magnet to be moved away from the aqueous object/droplet so that the aqueous object/droplet is no longer attracted to the magnet.

Alternatively, when the magnet is an electromagnet, the step of ceasing to expose the aqueous object/droplet to said magnetic field may comprise switching off the electromagnet. Typically, the electromagnet is switched off by stopping the current from flowing through the wires of the electromagnet.

The aqueous medium may be any suitable aqueous medium. For instance, the aqueous medium may be as defined herein.

As mentioned above, when two aqueous object/droplets are in contact with each other, a bilayer forms at the interface between the contacting aqueous object/droplets. By controlling the aqueous medium of the aqueous object/droplets and the concentration of amphipathic molecules on the surface of the aqueous object/droplet it is possible to fuse together two contacting aqueous object/droplets. The inventors have found that droplets, for example, may be fused together when the concentration of amphipathic molecules is relatively low. Typically, the droplets can be fused together when the concentration of amphipathic molecules is from $0.1$ mg mL$^{-1}$ to $1$ mg mL$^{-1}$, for instance $0.1$ mg mL$^{-1}$ to $0.75$ mg mL$^{-1}$. Usually, the droplets can be fused together when the concentration of amphipathic molecules is about $0.5$ mg mL$^{-1}$.

Accordingly, in some embodiments, the step of (iii) disposing the aqueous object/droplet at said second location comprises contacting the aqueous object/droplet with a second droplet and fusing the aqueous object/droplet with the second aqueous object/droplet to form a new aqueous object/droplet from the first and second aqueous object/droplets.

The second aqueous object/droplet may or may not comprise a magnetic material. Typically, when the step of (iii) disposing the aqueous object/droplet at said second location comprises contacting the aqueous object/droplet with a second aqueous object/droplet and fusing the aqueous object/droplet with the second aqueous object/droplet to form a new aqueous object/droplet from the first and second aqueous object/droplets, the second does not comprise a magnetic material.

Usually, when the new aqueous object/droplet is formed, the process of the invention further comprises a step of moving the magnet relative to the second location in a direction away from the second location whilst maintaining said magnetic attraction, and thereby causing the aqueous object/droplet to move away from said second location and towards a third location.

The third location may be the same location as the first location, or it may be a different location.

Typically, the step of moving the magnet relative to the second location, causing the aqueous object/droplet to move away from said second location and towards a third location, comprises moving the magnet using a micromanipulator.

The movement of the magnet relative to the second location may be automated.

Alternatively, the movement of the magnet relative to the first location may comprise moving the aqueous object/droplet using a micromanipulator. When the aqueous object/droplet is disposed in a hydrophobic medium, which is contained in a container, the movement of the magnet relative to the first location may comprise moving the container using a micromanipulator.

Usually, the step of moving the magnet relative to the second location moves the new aqueous object/droplet formed from the first and second aqueous object/droplets.

The step of fusing the aqueous object/droplet with the second aqueous object/droplet to form a new aqueous object/droplet is typically used in the carrier method but may also be used in the levitation method. The second aqueous object/droplet may, for instance, be in contact with one or more other aqueous object/droplets. The process may, for instance, be used to separate the second aqueous object/droplet from the other aqueous object/droplet(s).

Accordingly, typically, the new aqueous object/droplet formed from the first and second aqueous object/droplets contacts a third aqueous object/droplet through a bilayer (i.e. the new aqueous object/droplet formed from the first and second aqueous object/droplets forms a bilayer with a third aqueous object/droplet) and the step of moving the magnet relative to the second location causes the new aqueous object/droplet to move away from the third aqueous object/droplet. As the new aqueous object/droplets moves away from the third aqueous object/droplet the bilayer breaks.

When the process in accordance with the invention further comprises a step of moving the magnet relative to the second location, the process usually also further comprises disposing the aqueous object/droplet at said third location.

Typically, the step of disposing the aqueous object/droplet at said third location comprises ceasing to expose the aqueous object/droplet to said magnetic field at or near said third location.

Usually, the step of ceasing to expose the aqueous object/droplet to said magnetic field comprises moving the magnet away from the aqueous object/droplet. Typically the magnet is a permanent magnet and ceasing to expose the aqueous object/droplet to said magnetic field usually requires the magnet to be moved away from the aqueous object/droplet so that the aqueous object/droplet is no longer attracted to the magnet.

Alternatively, when the magnet is an electromagnet, the step of ceasing to expose the aqueous object/droplet to said magnetic field may comprise switching off the electromagnet. Typically, the electromagnet is switched off by stopping the current from flowing through the wires of the electromagnet.

Also provided by the invention is an aqueous object/droplet assembly which is obtainable by a process as defined herein. Such an aqueous object/droplet assembly as described herein and below may refer e.g. to an aqueous droplet assembly or e.g. to an assembly of hydrogel objects. Thus reference to aqueous object(s) embraces hydrogel object(s).

As mentioned above, processes in accordance with the invention may be used in the production of an aqueous object/droplet assembly. The aqueous object/droplet assembly is typically in a hydrophobic medium. The hydrophobic medium may, for instance, be a hydrophobic medium as defined herein.

The aqueous object/droplet assembly may form part of an encapsulate, for instance an aqueous object/droplet encapsulate. The process may be used to form an encapsulate comprising an aqueous object/droplet assembly. The encapsulate may, for instance, comprise: a volume (such as a drop) of a hydrophobic medium; a peripheral layer of amphipathic molecules around the surface of the volume; and an aqueous object/droplet assembly within the peripheral layer, wherein the aqueous object/droplet assembly is as defined herein.

A volume of said hydrophobic medium, with the aqueous object/droplet assembly disposed therein, may, for instance, be introduced into a bulk hydrophilic medium, such as an aqueous medium. The volume of said hydrophobic medium may be a drop of said hydrophobic medium.

The amphipathic molecules which form the peripheral layer of the encapsulate may, for instance, be provided in the hydrophobic medium or in the bulk hydrophilic medium. The encapsulate may, for example, be used when the hydrogel network is for use in a biological system.

The invention further provides an aqueous object/droplet assembly comprising a plurality of aqueous object/droplets wherein each aqueous object/droplet comprises an aqueous medium and an outer layer of amphipathic molecules around the surface of the aqueous medium, and wherein at least one of the plurality of aqueous object/droplets comprises a magnetic material disposed in the aqueous medium.

The magnetic material may be as further defined hereinabove for the process of the invention. Thus, typically, the magnetic material disposed in the aqueous medium of the aqueous object/droplet(s) comprises a paramagnetic or a superparamagnetic material, or a paramagnetic or a superparamagnetic metal, such as iron.

In some embodiments, the magnetic material disposed in the aqueous medium of the aqueous object/droplet(s) comprises a magnetic bead. The magnetic bead may, for instance, comprise magnetic particles.

Usually, the magnetic material disposed in the aqueous medium of the aqueous object/droplet(s) comprises a biocompatible magnetic material, such as a biocompatible magnetic bead.

Any suitable magnetic bead may be used. For instance, magnetic beads commercially available from, for instance, Clontech, Promega, Invitrogen and NEB, may be used.

In some embodiments, the magnetic bead comprises magnetic particles with an organic group such as a metal-chelating group, such as nitrilotriacetic acid (NTA), attached. The organic component may, for instance, comprise a group selected from —C(=O)O—, —C—O—C—, —C(=O), —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as nickel or cobalt is also attached to the metal-chelating group. Magnetic beads of this sort are commonly used for capturing His-tagged proteins, but are also suitable for use in the process and the produce of the present invention.

Typically, the magnetic bead may comprises a Ni-NTA or a Co-NTA magnetic bead, for instance, a Ni-NTA magnetic bead.

In some embodiments, the magnetic material is other than FeCo. Thus, the magnetic material may not comprise Fe. In some embodiments, the magnetic material does not comprise Fe and does not comprise Co.

Each aqueous object/droplet in the plurality of aqueous object/droplets will be in contact with at least one other aqueous object/droplet in the plurality of aqueous object/droplets. As discussed for the process of the invention, the boundary that is shared between contacting aqueous object/droplets at the point of contact between the objects, is referred to herein as an interface. Typically, a bilayer of amphipathic molecules is formed at an interface between contacting aqueous object/droplet. More typically, a bilayer of amphipathic molecules is formed at an interface between each of the contacting aqueous object/droplets in the plurality of aqueous object/droplets.

The aqueous object/droplet assembly may, for instance, comprise at least n of said aqueous object/droplets, and at least n-1 of said interfaces between contacting aqueous object/droplets, wherein n is equal to or greater than 2. The integer n may be equal to or greater than 3. More typically, n is equal to or greater than 4.

The integer n can in principle be very high, for instance in the order of millions. This is because the aqueous object/droplets may be very small and there is no upper limit on the size of the aqueous object/droplet assembly. Such assemblies, which can in principle comprise millions of aqueous object/droplets, may, for instance, be useful for preparing prototissue (i.e. an aggregate of protocells). In some embodiments, therefore, the integer n may be as high as several million, for instance up to about 10,000,000, or for instance up to about 5,000,000.

In other embodiments, n may be several hundred, for instance up to about 500, or for instance up to about 400. The integer n may for instance be an integer of from 2 to 500, or an integer of from 3 to 500. n may be an integer of from 2 to 400. In other embodiments, n may be an integer of from 2 to 300, or an integer of from 3 to 200. More typically n is from 2 to 200. In other embodiments, however, n is an integer of from 2 to 50, or an integer of from 3 to 50. n may for instance be from 2 to 20, or from 2 to 15.

Typically, the plurality of aqueous object/droplets comprises three or more aqueous object/droplets.

The magnetic assembly process defined herein may be automated. For example, for large aqueous object/droplet assemblies, such as when n is equal to or greater than 1000, or even equal to or greater than 5000, the magnetic assembly process defined herein would typically be automated. Any suitable method of automation may be used. The movement of the magnet may, for instance, be automated.

Usually, in the aqueous object/droplet assembly of the invention at least two of said plurality of aqueous object/droplets comprise a membrane protein and at least one of said plurality of aqueous object/droplets does not comprise a membrane protein.

The membrane protein may, for instance, be a membrane protein as defined herein for the process of the invention.

In some embodiments, the plurality of aqueous object/droplets comprises five or more aqueous object/droplets, for instance, from 5 to 50 aqueous object/droplets. The plurality of aqueous object/droplets may comprise nine or more aqueous object/droplets, for instance, from 9 to 20 aqueous object/droplets. For instance, the plurality of aqueous object/droplets may comprise from 9 to 14 aqueous object/droplets.

Typically, at least two of said plurality of aqueous object/droplets comprise a membrane protein. For instance, from 2 to 50 of said plurality of aqueous object/droplets comprise a membrane protein. In some embodiments, from 2 to 10 of said plurality of aqueous object/droplets comprise a membrane protein. For instance, from 2 to 8 of said plurality of aqueous object/droplets comprise a membrane protein.

In some embodiments, in the aqueous object/droplet assembly of the invention, at least one of said plurality of aqueous object/droplets comprises αHL and at least one of said plurality of aqueous object/droplets comprises a blocker of αHL. For instance, when the membrane protein comprises αHL, at least one of said plurality of aqueous object/droplets comprises a blocker of αHL, such as γ-cyclodextrin (γCD). Typically, the concentration of the blocker of αHL is equal to or greater than 10 μM, for instance equal to or greater than 25 μM. Usually, the concentration of the blocker of αHL is from 10 μM to 50 μM, for instance from 25 μM to 40 μM.

The aqueous object/droplet assembly may be a 2D assembly or a 3D assembly. Thus, the aqueous object/droplet assembly may comprise one or more layers of aqueous object/droplets. For instance, the aqueous object/droplet assembly may comprise from 1 to 10 layers of aqueous object/droplets. Typically, the aqueous object/droplet assembly comprises from 1 to 5 layers of aqueous object/droplets, for instance, one, two or three layers of aqueous object/droplets.

In some embodiments, the aqueous object/droplet assembly is a 3D assembly.

When the process of magnetic manipulation is automated (for instance when the movement of the magnet is automated) the number of layers of aqueous object/droplets may be even larger. For example, the aqueous object/droplet assembly may comprise from 1 to 10000 layers of aqueous object/droplets, for instance, from 1 to 1000 layers.

Usually, the aqueous object/droplet assembly of the invention comprises at least two layers of aqueous object/droplets. For instance, the aqueous object/droplet assembly may comprise two or three layers of aqueous object/droplets.

Typically, at least one of said plurality of aqueous object/droplets has a volume of less than or equal to 1500 nL. More typically, at least one of said plurality of aqueous object/droplets has a volume of from 100 nL to 1500 nL. For instance, at least one of said plurality of aqueous object/droplets may have a volume of from 300 nL to 900 nL. Usually, at least one of said plurality of aqueous object/droplets has a volume of from 300 nL to 900 nL for instance, from 400 nL to 800 nL. For instance, at least one of said plurality of aqueous object/droplets may have a volume of about 400 nL or about 800 nL.

In some embodiments, two or more of said plurality of aqueous object/droplets has a volume of less than or equal to 1500 nL. Typically, two or more of said plurality of aqueous object/droplets has a volume of from 100 nL to 1500 nL. For instance, two or more of said plurality of aqueous object/droplets may have a volume of from 300 nL to 900 nL. Usually, two or more of said plurality of aqueous object/droplets has a volume of from 300 nL to 900 nL for instance, from 400 nL to 800 nL. For instance, two or more of said plurality of aqueous object/droplets may have a volume of about 400 nL or about 800 nL.

Typically, each of said plurality of aqueous object/droplets has a volume of less than or equal to 1500 nL. More typically, each of said plurality of aqueous object/droplets has a volume of from 100 nL to 1500 nL. For instance, each of said plurality of aqueous object/droplets may have a volume of from 300 nL to 900 nL. Usually, each of said plurality of aqueous object/droplets has a volume of from 300 nL to 900 nL for instance, from 400 nL to 800 nL. For instance, each of said plurality of aqueous object/droplets may have a volume of about 400 nL or about 800 nL.

The aqueous object/droplets in the aqueous object/droplet assembly may be of the same volume or may be of different volumes. For instance, when the aqueous object/droplet assembly comprises two or more layers, the aqueous object/droplets in one layer of the aqueous object/droplet assembly may be a first volume and the aqueous object/droplets in another layer of the aqueous object/droplet assembly may be a second volume, wherein the first and second volumes are the same or different. If the aqueous object/droplet assembly comprises aqueous object/droplets of different volumes, this may have an effect on whether or not the neighbouring aqueous object/droplets are in contact with each other and thus whether or not there is an interface between the neighbouring aqueous object/droplets. If there is no interface, no bilayer is formed. This is illustrated e.g. in FIG. 13 of WO 2014/064461.

Accordingly, in some embodiments the aqueous object/droplet assembly of the invention comprises a first aqueous object/droplet of a first volume and a second aqueous object/droplet of a second volume, wherein the first and second volumes are different. Typically, the first aqueous object/droplet is in a first layer and the second aqueous object/droplet is in a second layer.

The aqueous object/droplets in the aqueous object/droplet assembly may be packed by any suitable packing arrangement. Suitable packing arrangements include, by are not limited to, cubic close packing and hexagonal close packing (as illustrated e.g. in FIG. 13 of WO 2014/064461).

The plurality of aqueous object/droplets may be of any shape. For instance, the plurality of aqueous object/droplets may form a parallelepiped shape, such as a cuboid, a flower shape or a pyramidal shape. In some embodiments, the plurality of aqueous object/droplets forms a pyramidal shape.

In some embodiments, the aqueous object/droplet assembly comprises a first plurality of aqueous object/droplets and a second plurality of aqueous object/droplets wherein: (a) the aqueous medium of the aqueous object/droplets of the first plurality of aqueous object/droplets comprises a membrane protein; and (b) the aqueous medium of the aqueous object/droplets of the second plurality of aqueous object/droplets does not comprise a membrane protein. The membrane protein is typically a membrane protein as defined herein for the process of the invention.

The aqueous medium of the aqueous object/droplets in the first plurality of aqueous object/droplets may, for instance, comprise a concentration of at equal to or greater than 10 ng mL$^{-1}$ of a membrane protein, for instance, equal to or greater than 50 ng mL$^{-1}$ of a membrane protein. Typically, the aqueous medium of the aqueous object/droplets in the first plurality of aqueous object/droplets comprises from 10 ng mL$^{-1}$ to 2000 µg mL$^{-1}$ of a membrane protein, for instance, from 50 ng mL$^{-1}$ to 1000 µg mL$^{-1}$. More typically, the aqueous medium of the aqueous object/droplets in the first plurality of aqueous object/droplets comprises from 75 ng mL$^{-1}$ to 900 µg mL$^{-1}$.

In another embodiment, the aqueous object/droplet assembly comprises a first plurality of aqueous object/droplets and a second plurality of aqueous object/droplets wherein: (a) the aqueous medium of the aqueous object/droplets of the first plurality of aqueous object/droplets comprises a first concentration of a membrane protein; and (b) the aqueous medium of the aqueous object/droplets of the second plurality of aqueous object/droplets comprises a second concentration of the membrane protein, wherein the first concentration is greater than the second concentration.

In some embodiments, the aqueous object/droplet assembly comprises a first plurality of aqueous object/droplets and a second plurality of aqueous object/droplets wherein: (a) the aqueous medium of the aqueous object/droplets of the first plurality of aqueous object/droplets comprises a concentration of at least 50 ng mL$^{-1}$ of a membrane protein; and (b) the aqueous medium of the aqueous object/droplets of the second plurality of aqueous object/droplets comprises a concentration of less than 50 ng mL$^{-1}$ of the membrane protein. Usually, the membrane protein is a membrane protein as defined herein for the process of the invention.

For instance, the aqueous object/droplet assembly may comprise a first plurality of aqueous object/droplets and a second plurality of aqueous object/droplets wherein: (a) the aqueous medium of the aqueous object/droplets of the first plurality of aqueous object/droplets comprises a concentration of at least 50 ng mL$^{-1}$ of a membrane protein, for instance, at least 100 ng mL$^{-1}$; and (b) the aqueous medium of the aqueous object/droplets of the second plurality of aqueous object/droplets comprises a concentration of less than 5 ng mL$^{-1}$ of the membrane protein, for instance, less than 1 ng mL$^{-1}$.

In some embodiments, the aqueous object/droplet assembly comprises a first plurality of aqueous object/droplets and a second plurality of aqueous object/droplets wherein: (a) a bilayer of amphipathic molecules is formed at an interface between each of the contacting aqueous object/droplets in the first plurality of aqueous object/droplets and each bilayer between each of the contacting aqueous object/droplets in the first plurality of aqueous object/droplets comprise a membrane protein; and (b) a bilayer of amphipathic molecules is formed at an interface between each of the contacting aqueous object/droplets in the second plurality of aqueous object/droplets and none of the bilayers between each of the contacting aqueous object/droplets in the second plurality of aqueous object/droplets comprise the membrane protein.

Typically, the aqueous object/droplet assembly comprises a first plurality of aqueous object/droplets and a second plurality of aqueous object/droplets wherein: (a) a bilayer of amphipathic molecules is formed at an interface between each of the contacting aqueous object/droplets in the first plurality of aqueous object/droplets and each bilayer between each of the contacting aqueous object/droplets in the first plurality of aqueous object/droplets comprise a membrane protein; and (b) a bilayer of amphipathic molecules is formed at an interface between each of the contacting aqueous object/droplets in the second plurality of aqueous object/droplets and none of the bilayers between each of the contacting aqueous object/droplets in the second plurality of aqueous object/droplets comprise a membrane protein.

In another embodiment, the aqueous object/droplet assembly comprises a first plurality of aqueous object/droplets and a second plurality of aqueous object/droplets wherein: (a) a bilayer of amphipathic molecules is formed at an interface between each of the contacting aqueous object/droplets in the first plurality of aqueous object/droplets and the bilayers between the contacting aqueous object/droplets in the first plurality of aqueous object/droplets comprise a first concentration of the membrane protein; and (b) a bilayer of amphipathic molecules is formed at an interface between each of the contacting aqueous object/droplets in the second plurality of aqueous object/droplets and the bilayers between the contacting aqueous object/droplets in the second plurality of aqueous object/droplets comprise a second concentration of the membrane protein, wherein the first concentration is greater than the second concentration.

Droplets and other aqueous objects can exchange chemical species with each other through membrane proteins incorporated in the bilayer between the aqueous object/droplets. Suitable membrane proteins include, but are not limited to, pumps, channels and/or pores, receptor proteins, transporter proteins, for instance an α-hemolysin (αHL) pore. Thus, an aqueous object/droplet assembly may be capable of trafficking materials such as chemical compounds through the network, from object to object, as well as to and from the external environment. Complex transport systems can be built up in this way.

An aqueous object/droplet assembly may, for instance, act as a sensor module, capable of sensing the presence of a particular chemical in the external environment, for instance, or capable of sensing light. Thus, the aqueous object/droplet may in some embodiments comprise a sensor molecule. The sensor molecule can be present in the aqueous medium of the aqueous object/droplet or in the bilayer. The sensor molecule may be a molecule which is sensitive to the presence of a particular chemical (for instance a target analyte), or it may be a light-sensitive molecule.

In some embodiments, the aqueous object/droplet assembly comprises a first plurality of aqueous object/droplets and a second plurality of aqueous object/droplets, wherein the aqueous object/droplets in the first plurality of aqueous object/droplets are in communication with one another via the membrane proteins.

Usually, the aqueous object/droplet assembly comprises a first plurality of aqueous object/droplets and a second plurality of aqueous object/droplets, wherein the aqueous object/droplets in the first plurality of aqueous object/droplets are in communication with one another via the membrane proteins and the aqueous object/droplets in the second plurality of aqueous object/droplets are not in communication with one another via the membrane proteins.

The aqueous object/droplet assembly may, for instance, be a 3D assembly. Such a functional 3D assembly, capable of transmitting electrical signals along defined paths, is analogous to a tissue, and can form the basis of a model system with a higher number of aqueous object/droplets mimicking a neuronal tissue.

At least one of the aqueous object/droplets in the first plurality of aqueous object/droplets and/or the second plurality of aqueous object/droplets may, in some embodiments, comprise other materials, compounds or substances. For instance, at least one of the aqueous object/droplets in the first plurality of aqueous object/droplets and/or the second plurality of aqueous object/droplets may comprise a small molecule, such as a dye, or a magnet. Suitable dyes include, but are not limited to, xylene cyanol FF, orange G, pyranine, fluorescein and 5-cTAMRA (5-carboxytetramethylrhodamine). Alternatively, the aqueous object/droplet may comprise a sensor molecule, for instance a sensor molecule that is sensitive to a particular chemical or is a light-sensitive molecule. As a further alternative, at least one of the aqueous object/droplets in the first plurality of aqueous object/droplets and/or the second plurality of aqueous object/droplets may comprise a therapeutic agent, such as a prodrug, or a diagnostic agent, such as a contrast agent.

By using 3D networks of aqueous object/droplets containing different molecules to perform specific functions, akin to the differentiated cells of biological tissues, the aqueous object/droplet assemblies of the invention may be used in the building of functional synthetic minimal tissues. The ability to switch rapidly between aqueous object/droplet configurations, afforded by the present invention, does not occur naturally, and will add to the versatility of synthetic minimal tissues.

The aqueous object/droplet assembly of the invention is typically stable for at least one day, for instance at least two days. The aqueous object/droplet assembly may, for instance, be stable for at least 3 or at least 4 days.

The aqueous structures/droplets of the aqueous object/droplet assembly may be produced by any suitable method or a combination of suitable methods.

For instance, the aqueous structures/droplets may be produced by injecting or pipetting a composition comprising the aqueous medium into a suitable medium, such as a hydrophobic medium.

In some embodiments, the aqueous structures/droplets of the aqueous object/droplet assembly are produced using a microfluidic device. A microfluidic device may, for instance, be used to produce at least n of said droplets, wherein n is equal to or greater than 2. The integer n may be equal to or greater than 3. More typically, n is equal to or greater than 4. As discussed above n can, in principle, be very high. In some embodiments, therefore, the integer n may be as high as several million, for instance up to about 10,000,000, or for instance up to about 5,000,000. In other embodiments, n may be several hundred, for instance up to about 500, or for instance up to about 400. The integer n may for instance be an integer of from 2 to 500, or an integer of from 3 to 500. n may be an integer of from 2 to 400. In other embodiments, n may be an integer of from 2 to 300, or an integer of from 3 to 200. More typically n is from 2 to 200. In other embodiments, however, n is an integer of from 2 to 50, or an integer of from 3 to 50. It may for instance be from 2 to 20, or from 2 to 15.

Techniques such as soft-lithography may be used to produce one or more of the aqueous structures/droplets of the aqueous object/droplet assembly. One or more aqueous structures/droplets may, for instance, be molded. In some embodiments, PMMA molds may be used to produce one or more aqueous structures/droplets. Soft-lithography may, for instance, be used to produce one of more aqueous structures/droplets comprising a hydrogel. Mold may, for instance, be used when the aqueous object/droplet comprises a hydrogel.

One or more aqueous object/droplets of the aqueous object/droplet assembly may be produced using photolithograph. A photomask may, for instance, be used to define a pattern through which the light (such as UV light) can pass. Photolithography may, for instance, be used to produce one of more aqueous structures/droplets comprising a photocurable polymer. Photolithography may, for instance, be used when the aqueous object/droplet comprises a hydrogel.

At least one of the plurality of aqueous structures/droplets in the aqueous object/droplet assembly comprises a magnetic material disposed in an aqueous material. In some embodiments at least a quarter of the aqueous structures/droplets in the aqueous object/droplet assembly comprise a magnetic material, for instance, at least half of the aqueous object/droplets in the aqueous object/droplet assembly may comprise a magnetic material. In some embodiments, all of the aqueous structures/droplets in the aqueous object/droplet assembly comprise a magnetic material. The number of aqueous object/droplets in the aqueous object/droplet assembly that comprise a magnetic material may, for instance, depend on the process used to produce the aqueous object/droplet assembly. For instance, if the levitation method is used to produce the aqueous object/droplet assembly at least half of the aqueous object/droplets may comprise a magnetic material, for instance, all of the aqueous object/droplets may comprise a magnetic material.

The aqueous object/droplet assembly of the invention may form part of a aqueous object/droplet encapsulate. The encapsulate may, for instance, comprise: a volume (for instance a drop) of a hydrophobic medium; a peripheral layer of amphipathic molecules around the surface of the volume; and an aqueous object/droplet assembly within the peripheral layer, wherein the aqueous object/droplet assembly is an aqueous object/droplet assembly as defined herein. The volume of hydrophobic medium, with the aqueous object/droplet assembly disposed therein, may be provided in a bulk hydrophilic medium, such as an aqueous medium. The volume of hydrophobic medium may be a drop of said hydrophobic medium.

Typically, the hydrophilic medium is an aqueous medium.

The inventors have found that a process as defined herein in accordance with the invention may be used to assemble an aqueous object/droplet assembly. The aqueous object/droplet assembly may be a 2D or 3D assembly of aqueous object/droplets. The aqueous object/droplet assembly may, for instance, be an aqueous object/droplet assembly as defined herein for the aqueous object/droplet assembly of the invention.

An advantage of the present invention is that it allows complex 3D structures to be created in a controlled manner. Information may, for example, be passed from one aqueous object/droplet to another within the aqueous object/droplet assembly, for instance, via membrane proteins. By moving from a 2D assembly to a 3D assembly, the number of intercommunicating aqueous structures/droplets can be increased. As discussed in relation to droplets in International patent application publication WO 2014/064461, the contents of which is incorporated herein by reference, the Manhattan distance between the furthest spaced aqueous structures/droplets in an N aqueous object/droplet 2D network can be increased from $\sqrt{N}$ in a 2D assembly to $\sqrt[3]{N}$ in a 3D assembly.

The process in accordance with the invention may be used to build up an assembly of aqueous structures/droplets.

There are number of different ways in which the process may be used to assemble an aqueous object/droplet assembly. The disclosure of International patent application publication WO 2014/064461 demonstrates some of the ways in which the process may be used to assemble an aqueous object/droplet assembly.

Example 1 of WO 2014/064461, for instance, demonstrates the use of the levitation method to form a droplet assembly. By repeating the process, each repetition moving at least one droplet comprising a magnetic material, a droplet assembly may be assembled. For example, each repetition of the process may move a single droplet. Alternatively, at least one of the repetitions of process may move two or more droplets.

Further, Example 3 of WO 2014/064461 shows how the carrier method may be used to form a droplet assembly. For instance, the step (iii) disposing the droplet at said second location may bring the droplet into contact with another droplet. The other droplet may or may not comprise a magnetic material. Typically a bilayer forms at the interface between the droplet and the other droplet. The process of the invention may be repeated. The first repetition may, for example, bring the two droplets connected by a bilayer into contact with a third droplet. Thus the repetition of the process moves more than one droplet.

An aqueous object/droplet assembly may be assembled using a combination of the levitation method and the carrier method.

The inventors have also found that processes in accordance with the invention may be used to disassemble an aqueous object/droplet assembly. Both the levitation method and the carrier method may be used to disassemble an aqueous object/droplet assembly. When the process is used to disassemble a 2D or 3D structure comprising droplets, the droplet at the first location is initially in contact with another droplet. The droplet may, for instance, form a bilayer with the other droplet.

The use of the process to disassemble a droplet assembly is illustrated in Examples 2 and 4 of WO 2014/064461.

Example 2 of WO 2014/064461 illustrates the use of the levitation method to disassemble a droplet assembly. The droplet at the first location is a droplet in the droplet assembly. As mentioned above, typically when the levitation method is used the droplet, when at the first location, will be disposed on a patterned surface. At least one of the other droplets in the droplet assembly will also be disposed on a patterned surface. As discussed in Example 2 of WO 2014/064461, the patterned surface helps to hold the other droplets in place so that only the droplet is moved in the process. As the skilled person will appreciate, as the number of droplets in the droplet assembly decreases, it typically becomes more difficult to remove further droplets.

Disassembly is illustrated in Example 4 of WO 2014/064461. In this method the droplet is fused to a droplet in the droplet assembly, thus the droplet at the first location is not a droplet in the droplet assembly. The inventors have found that fusion of the droplet with another droplet typically becomes easier when the concentration of amphipathic molecules is reduced. Fusion may, for instance, take less than or equal to 120 seconds, for instance from 3 to 29 seconds.

The aqueous object/droplet assembly may form part of an encapsulate, for instance an aqueous object/droplet encapsulate. The droplet encapsulate generally comprises: a volume (such as a drop) of a hydrophobic medium; a peripheral layer of amphipathic molecules around the surface of the volume; and a aqueous object/droplet assembly within the peripheral layer, wherein the aqueous object/droplet assembly is as defined herein. The amphipathic molecules which form the peripheral layer of the encapsulate may, in processes in accordance with the invention, be provided in the hydrophobic medium or in the bulk hydrophilic medium.

The use of processes in accordance with the invention to assemble and disassemble an aqueous object/droplet assembly has been discussed above. As the skilled person will appreciate, these processes may also be used to rearrange an aqueous object/droplet assembly. This may, for example, comprise removal of an aqueous object/droplet or aqueous structures/droplets from the assembly, moving the aqueous object(s)/droplet(s) and disposing the aqueous object(s)/droplet(s) so that the aqueous object(s)/droplet(s) make contact with a different aqueous object/droplet within the assembly. This is illustrated e.g. in FIG. 9 of WO 2014/064461.

Figure 11A:
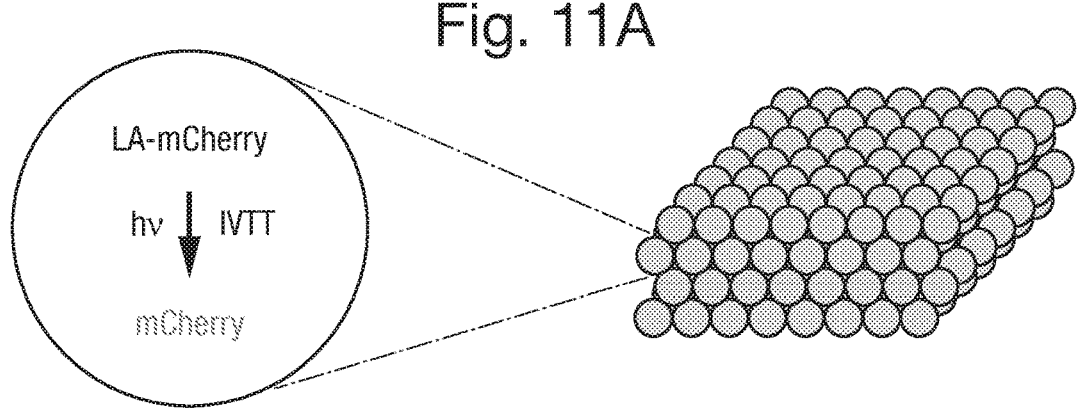
FIG. 11 shows light-activated expression from LA-mCherry DNA in synthetic tissues. (A) Schematic of a synthetic cell that will express mCherry after light activation. (B) 3D-printed synthetic tissues containing LA-mCherry DNA express mCherry (white/light-grey) upon light activation. (C) Fluorescence intensity line profile of B. Top line is +UV and bottom line next to X-axis is −UV.
Figure 11B:
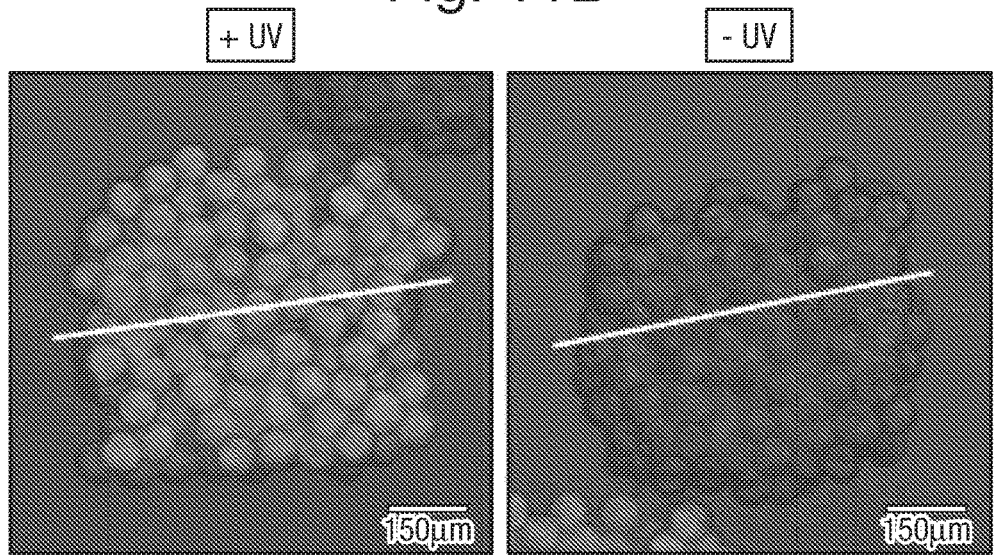
Figure 11C:
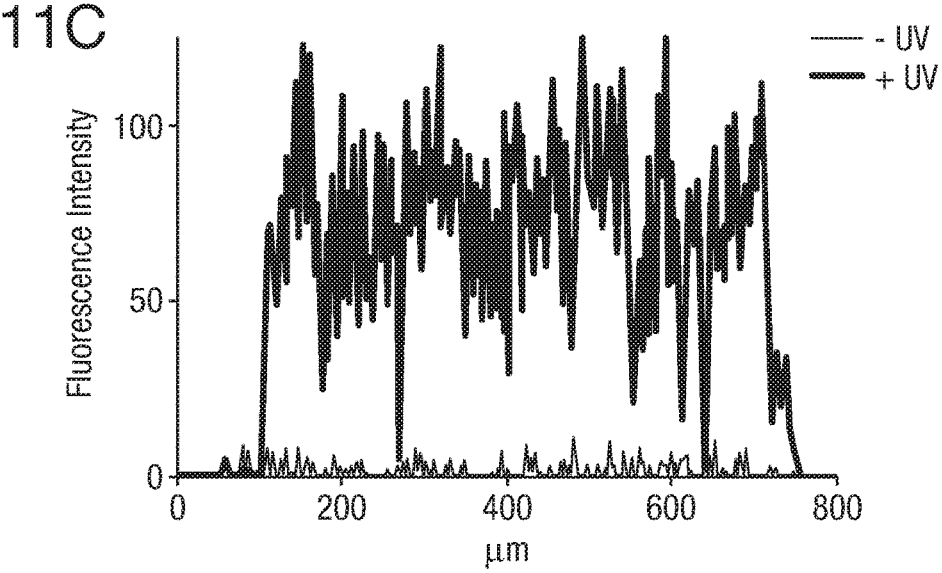

Alternatively, processes in accordance with the invention, as described herein, may be used to move a plurality of aqueous object(s)/droplets from a first location to a second location simultaneously. The movement of a plurality of aqueous object(s)/droplets (without levitation) is illustrated e.g. in FIG. 11 of WO 2014/064461. The inventors have found, during transport of an entire assembly, the shape of the assembly and any bilayer connections can be retained.

The processes in accordance with the invention, as described herein, may be used to move a single aqueous object/droplet from the first location to the second location. These processes may also be used to move the aqueous object/droplet and one or more other aqueous structures/droplets from the first location to the second location. Typically, each interface between the contacting aqueous structures/droplets being moved comprises a bilayer of amphipathic molecules. As the skilled person will appreciate, when moving more than one aqueous object/droplet, the forces holding the aqueous object/droplets together (e.g. the interaction strength between the two monolayers forming the bilayer at an interface) must be stronger than those forces pulling the aqueous structures/droplets apart. This typically means that the bilayer strength must be greater than the drag force. FIG. 21 of WO 2014/064461 outlines the forces acting on the droplet and the other droplet it is in contact with, using the carrier method.

In some embodiments, the aqueous structures/droplet at the first location forms a bilayer with a second aqueous structures/droplet and the step of (i) exposing an aqueous structures/droplet to said magnetic field causes the aqueous object/droplet and the second aqueous object/droplet to rise to the top of the hydrophobic medium and move towards the magnet.

Typically, the second aqueous object/droplet comprises a magnetic material. Usually, the magnetic material is as defined herein.

Usually, when the step of (i) exposing an aqueous object/droplet to said magnetic field causes the aqueous object/droplet and the second aqueous object/droplet to rise to the top of the hydrophobic medium and move towards the magnet, the step of (ii) moving the magnet relative to the first location moves the first aqueous object/droplet and the second aqueous object/droplet.

Typically, the step of (iii) disposing the aqueous object/droplet at said second location comprises ceasing to expose the aqueous object/droplet to said magnetic field at or near said second location.

When the step of (i) exposing an aqueous object/droplet to said magnetic field causes the aqueous object/droplet and the second aqueous object/droplet to rise to the top of the hydrophobic medium and move towards the magnet, usually, the step of (iii) disposing the aqueous object/droplet at said second location comprises ceasing to expose the aqueous object/droplet to said magnetic field near said second location and allowing the aqueous object/droplet to arrive at said second location.

For instance, the aqueous object/droplet may arrive at said second location by falling through the hydrophobic medium under gravity.

Usually, the step of ceasing to expose the aqueous object/droplet to said magnetic field comprises moving the magnet away from the aqueous object/droplet. Typically the magnet is a permanent magnet and ceasing to expose the aqueous object/droplet to said magnetic field usually requires the magnet to be moved away from the aqueous object/droplet so that the aqueous object/droplet is no longer attracted to the magnet.

Alternatively, when the magnet is an electromagnet, the step of ceasing to expose the aqueous object/droplet to said magnetic field may comprise switching off the electromagnet. Typically, the electromagnet is switched off by stopping the current from flowing through the wires of the electromagnet.

Processes in accordance with the invention may further comprise recovering said aqueous object/droplet.

The invention further provides an electrochemical circuit comprising a network of aqueous objects, e.g. droplets or hydrogel objects, which network comprises a plurality of aqueous objects, e.g. droplets or hydrogel objects.

In one embodiment, each of said aqueous objects comprises: a droplet, and an outer layer of amphipathic molecules on at least part of the surface of the droplet, wherein each of said droplets contacts another of said droplets to form an interface between the contacting droplets. The network of hydrogel objects is as defined herein.

In one embodiment, each of said aqueous objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects. The network of hydrogel objects is as defined herein.

In the electrochemical circuit of the invention, the current may be carried through the network by ions.

Usually, the electrochemical circuit of the invention comprises a first electrode which is in contact with a said aqueous, e.g. hydrogel, object, and a second electrode.

The electrodes are typically electrochemically reversible electrodes. Usually, the first electrode and/or the second electrode comprises an electrochemically active electrode such as a Ag/AgCl electrode.

Alternatively, the electrodes may be a high work function metal (for instance gold, silver, nickel, palladium or platinum), if used in conjunction with an electrochemically active mediator such as ferrocyanide. For instance, a redox couple, or a member of a redox couple which may be partially oxidised or reduced to provide the redox couple, may be used. Suitable redox couples include those known in the art such as $Fe^{2+}/Fe^{3+}$, ferrocene/ferrocium or $Ru^{2+}/Ru^{3+}$. Examples of such are ferro/ferricyanide, ruthenium hexamine and ferrocene carboxylic acid.

In some embodiments, the second electrode is not in contact with any of said plurality of aqueous, e.g. hydrogel, objects in the network. An example of an electrochemical circuit in which the second electrode is not in contact with any of a plurality of hydrogel objects in a hydrogel network is shown in FIG. 7 of WO2014064459. In other embodiments, the second electrode is in contact with at least one of said plurality of aqueous, e.g. hydrogel, objects in the network.

As the skilled person will appreciate, the aqueous, e.g. hydrogel, objects in the network could reconfigure to form a different arrangement. If this occurs, it is possible that, in one configuration the second electrode is not in contact with any of said plurality of aqueous, e.g. hydrogel, objects in the network and in another configuration the second electrode is in contact with at least one of said plurality of aqueous, e.g. hydrogel, objects in the network. Thus the electrochemical circuit could, for instance, form a switch or a component part of a switch.

Typically, the electrochemical circuit of the invention comprises a first electrode which is in contact with a said aqueous, e.g. hydrogel, object, and a second electrode, which second electrode is in contact with a different aqueous, e.g. hydrogel, object. The different object that is in contact with the second electrode may be one of said plurality of aqueous, e.g. hydrogel, objects in the network. Alternatively, the different aqueous, e.g. hydrogel, object that is in contact with the second electrode may not be one of said plurality of aqueous, e.g. hydrogel, objects in the network. It may be a "further aqueous, e.g. hydrogel, object" of the kind described above, e.g., a "stand-alone" object.

In some embodiments, the second electrode is in contact with another of said aqueous, e.g. hydrogel, objects of said plurality of aqueous, e.g. hydrogel, objects in the network.

In some embodiments, in the electrochemical circuit of the invention, at least one of said aqueous objects is a hydrogel body comprising a hydrogel wire. The hydrogel wire, or wire-shaped hydrogel body, is typically as herein defined. In some embodiments, at least two of said hydrogel objects is a hydrogel wire.

The electrochemical circuit may comprise many such wires that link together in the circuit. In this way complete circuits can be built up. Thus, for instance, all of the hydrogel bodies in the electrochemical circuit may be hydrogel wires.

Typically, the electrochemical circuit of the invention further comprises a hydrophobic medium, wherein the network is in contact with the hydrophobic medium.

In some embodiments, one or more of said aqueous, e.g. hydrogel, objects is disposed on a substrate. The substrate is usually non-conducting.

The substrate may, for instance, comprise glass or plastic. Thus the substrate may, for instance, be a Petri plate. Wherein the aqueous objects are hydrogel objects, the hydrogel objects may be any hydrogel object as defined herein.

In some embodiments, the substrate comprises a polymer. The repeat unit of the polymer may, for instance, comprise a —C(=O)O— or a —Si(CH$_3$)$_2$O— group. The polymer may, for instance, be PMMA (poly(methyl methacrylate)) or PDMS (polydimethylsiloxane).

The invention further provides an electrochemical circuit comprising a hydrogel network, which network comprises a plurality of hydrogel objects, wherein each of said hydrogel objects comprises a hydrogel body, and wherein each of said hydrogel objects contacts another of said hydrogel objects to form an interface between the contacting hydrogel objects. Usually the electrochemical circuit further comprises a first electrode which is in contact with a said hydrogel object, and a second electrode.

Thus the hydrogel objects in the hydrogel network of the electrochemical circuit do not necessarily comprise an outer layer of amphipathic molecules, on any part of the surface of the hydrogel body. When there is no outer layer of amphipathic molecules there is typically no bilayer of amphipathic molecules at the interface between the contacting hydrogel objects. In some embodiments, for example, the hydrogel objects are not in a hydrophobic medium.

The hydrogel body of one hydrogel object may for instance be in direct contact with the hydrogel body of another hydrogel object at at least one of said interfaces between contacting hydrogel objects.

In some embodiments, the second electrode is not in contact with any of said plurality of hydrogel objects in the hydrogel network. In other embodiments, the second electrode is in contact with at least one of said plurality of hydrogel objects in the hydrogel network.

The hydrogel body may be as further defined hereinbefore.

Typically, the electrochemical circuit comprises said first electrode which is in contact with said hydrogel object and a second electrode which is in contact with another of said hydrogel objects.

In some embodiments, at least one of said hydrogel bodies is a hydrogel wire. Usually, the wire, or wire-shaped hydrogel body, is as defined herein. Typically, at least two of said hydrogel objects is a hydrogel wire. For instance, the electrochemical circuit may comprise three or more hydrogel objects in the shape of a wire. In some embodiments, at least half of the hydrogel bodies are hydrogel wires, for instance, all of the hydrogel bodies are hydrogel wires.

In the electrochemical circuit, there may, for instance be at least one hydrogel wire that is in contact with the first electrode or the second electrode. In some embodiments, there may be at least one of said hydrogel wires that is not in contact with the first electrode or the second electrode.

The electrochemical circuit may further comprise a hydrophobic medium, which hydrophobic medium is in contact with the hydrogel network. Typically, the hydrophobic medium is as defined herein.

In some embodiments, one or more of said hydrogel objects is disposed on a substrate. The substrate may be as further defined herein. The hydrogel objects may also be as further defined herein.

In one embodiment, any one of said plurality of hydrogel objects further comprises an outer layer of amphipathic molecules, on at least part of the surface of the hydrogel body. The amphipathic molecules may be as further defined herein. For instance, each of said plurality of hydrogel objects may further comprise an outer layer of amphipathic molecules, on at least part of the surface of the hydrogel body.

Usually, the concentration of amphipathic molecules is as defined hereinbefore.

The invention also provides a hydrogel component for a mechanical device, which hydrogel component comprises a hydrogel network, which network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects.

The frameworks of conventional machines and their parts (e.g. gears, screws, nuts and bolts) are made of hard components. However, the inventors have found that a hydrogel network can be used as part of a mechanical device (a "soft-matter mechanical device"), thus demonstrating that mechanical devices may comprise soft components. For example, a hydrogel network may be used to form at least part of the mechanical components required to switch electrical circuits. This is demonstrated e.g. in FIG. 15 of WO 2014/064459, which shows a cross-shaped hydrogel object, covered with a lipid monolayer, used as a manual switch in an electrical circuit.

Typically, in the hydrogel component of the invention, the network of hydrogel objects is as further defined herein.

In some embodiments, one or more of said hydrogel objects is, or forms part of, a moveable part.

The moveable component part may comprise all of said hydrogel objects. Alternatively, there may be additional hydrogel objects in the network that do not form part of said component part. There may be two or more component parts. In which case individual component parts may move independently from each other or may move together.

In some embodiments, one or more of said hydrogel objects forms a part which is moveable relative to one or more other hydrogel objects in the network. An example of a hydrogel component in which one or more of said hydrogel objects forms a part which is moveable relative to one or more other hydrogel objects in the network is a switch.

A variety of different stimuli may be used to move the moveable part.

The moveable part may, for instance, be moveable by the application of a magnetic force, an electromagnetic force, a mechanical force or a manual force. For instance, a magnetic material may be inserted into a hydrogel object, which object may then be moved by the application of an external magnetic field. (An external magnetic field may be applied, for instance, by bringing a magnet, such as a neodymium magnet, towards the hydrogel object or by switching on an electromagnetic field.) The magnetic material inserted into the hydrogel object may, for example, comprise a magnetic bead.

In some embodiments, the moveable part comprises a rotor or a component of a switch. The moveable part may, for instance, form part of an electrical circuit in which the moveable part is moved in order to switch the circuit on or off. Alternatively, the moveable part may form part of rotor.

When the hydrogel component forms a component of a switch, the switch may comprise at least three hydrogel objects. For instance, the switch may comprise two spherical hydrogel objects and a bar-shaped hydrogel object. In this configuration, the bar-shaped hydrogel object may, for instance, be rotated so that it is in contact with the two spherical hydrogel objects (for example to turn the switch on) or it may be rotated so that it is not in contact with the two spherical hydrogel objects (for example to turn the switch off).

Alternatively, the switch may comprise a cross-shaped hydrogel object. The switch may further comprise two spherical hydrogel objects. In some embodiments, the cross-shaped object may be rotated so that it is in contact with the two spherical hydrogel objects (for example to turn the switch on) or it may be rotated so that it is not in contact with the two spherical hydrogel objects (for example to turn the switch off). When the cross-shaped hydrogel object is in contact with the spherical hydrogel objects at least two interfaces will form, one interface between each spherical hydrogel object and the cross-shaped hydrogel object. A bilayer of amphipathic molecules may, for instance, form at at least one of these interfaces. Typically, a bilayer of amphipathic molecules will form at both of these interfaces.

When the hydrogel component forms part of a rotor, the rotor may, for instance, be rotated using a magnetic field.

Usually, the rotor comprises at least five hydrogel objects. Typically, the rotor comprises at least one cross-shaped hydrogel object and four crescent-shaped hydrogel objects. More typically, the interfaces between the crescent-shaped hydrogel objects and the cross-shaped hydrogel object do not comprise a bilayer of amphipathic molecules. For instance, at the interfaces of the cross-shaped hydrogel object with each of the crescent-shaped hydrogel objects, the hydrogel objects may be in direct contact with each other. Thus, the cross-shaped hydrogel object may be in direct contact with four crescent-shaped hydrogel objects. One or more of said hydrogel objects may, for instance, comprise a magnet, such as a magnetic bead.

Further applications of aqueous object, e.g. particularly hydrogel, networks of the invention include, but are not limited to, providing a novel platform for the fundamental study of membrane proteins and acting as multi-compartment protocellular chassis for "bottom-up" synthetic biology. Thus, the networks can be used to make protocells and prototissues.

With respect to synthetic minimal tissues, hydrogel shapes are robust biocompatible building blocks with forms that cannot be retained by purely aqueous droplets. The hydrogel endows an aqueous compartment with a primitive cytoskeleton. For example, hydrogel bodies can be assembled into structures in which the building blocks can be separated with bilayers of amphipathic molecules, such as lipid bilayers. The structures may be readily rearranged and communication through the interface bilayers may be achieved with protein pores. By this means, electrical signalling through the structures or to contacting electrodes is possible. The versatility of the signalling may be enhanced by the use of extruded hydrogel wires or painted hydrogel connections. These wires and connections are analogs of neurons.

Thus, the invention also provides the use of an aqueous object network, particularly a hydrogel network, in synthetic biology. The aqueous object network, e.g. droplet or hydrogel network, may be as defined herein.

Further provided is the use of an aqueous object network, particularly a hydrogel network, of the invention as defined herein, or a composition of the invention as defined herein, in a method of preparing a protocell or an aggregate of protocells (prototissue).

The invention also provides the use of an aqueous object network, particularly a hydrogel network, as defined herein as a component of an electrochemical circuit or of a mechanical device. The electrochemical circuit or mechanical device may be as further defined herein.

In some embodiments, when a hydrogel network is used as a component of a mechanical device, the hydrogel network comprises moveable parts. The moveable parts may be as defined herein. For instance, the hydrogel network may comprise a rotor. A hydrogel rotor may, for instance, be used as a droplet-collecting unit.

A droplet-collecting unit may comprise a rotor as herein defined. The droplet-collecting unit may be used to collect droplets around the rotor. The droplets may, for instance, be aqueous droplets or hydrogel bodies as herein defined. The collection of the droplets may be facilitated by the formation of bilayers of amphipathic molecules between the droplets and one of more of the hydrogel objects of the rotor. The droplets may, for instance, be collected as a result of the centripetal force created by the rotation of the rotor. Droplet-collecting units are shown e.g. in FIGS. 19 and 20 of WO 2014/064459. The experiments demonstrate the feasibility of using soft-matter components to fabricate mechanical devices for use in the bottom-up assembly of bilayer networks.

The invention also provides the use of a hydrogel network as defined herein as a switch or as a component part of a switch. The switch or component part of a switch may be as defined herein. For instance, the hydrogel network may be used as an electrochemical switch.

The hydrogel networks of the invention can be produced by the process of the invention for producing a hydrogel network, which hydrogel network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects; which process comprises introducing a plurality of hydrogel bodies into a medium comprising a plurality of amphipathic molecules; and assembling said hydrogel bodies into a said network, or allowing said hydrogel bodies to self-assemble into a said network. The hydrogel network is as defined herein.

The hydrogel body is as herein defined. Usually, the hydrogel body is molded. For instance, PMMA molds of the desired shape may be used to produce the hydrogel bodies. Typically, the hydrogel is melted and poured into the mold. In some embodiments, at least one hydrogel body in the hydrogel network may comprise more than one hydrogel.

The hydrogel may be as herein defined. After gelling, the hydrogel is usually removed from the mold and immersed in a hydrophobic medium. To form a wire-shaped hydrogel body, warm hydrogel is typically drawn into a tube by capillary action. The warm hydrogel is then usually allowed to gel. The wire-shapes hydrogel bodies produced are typically wires as herein defined.

Alternatively, the hydrogel body may be shaped using light (such as UV light) from a light source and a photomask. The photomask is typically used to define a pattern through which the light can pass. Usually, the hydrogel body is shaped by shining light (such as UV light) through a photomask onto a photocurable polymer. The photocurable polymer is polymerised by the light. In this embodiment, the hydrogel comprises a photocurable polymer.

Typically, the medium is a hydrophobic medium as herein defined.

Usually, the amphipathic molecules are as herein defined.

Typically, the step of introducing a plurality of hydrogel bodies into a medium comprising a plurality of amphipathic molecules comprises introducing a plurality of hydrogel bodies into a hydrophobic medium, such as hexadecane, which hydrophobic medium comprises a plurality of amphipathic molecules. Usually, the amphipathic molecules comprise lipids, such as DPhPC.

In some embodiments, the hydrophobic medium comprises hexadecane, the amphipathic molecules comprise DPhPC and the hydrogel in the hydrogel bodies comprises agarose.

Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

The hydrogel body may comprise a hydrophilic material, such as agarose, and a hydrophobic material.

Usually, the concentration of amphipathic molecules in the medium is less than or equal to 15 mg mL$^{-1}$. For instance, the concentration of amphipathic molecules may be from 0 to 10 mg mL$^{-1}$.

In some embodiments, the concentration of amphipathic molecules in the medium is usually equal to or greater than 0.5 mg mL$^{-1}$. For instance, the concentration of amphipathic molecules may be equal to or greater than 5 mg mL$^{-1}$. Usually, the concentration of amphipathic molecules is from 0.5 mg mL$^{-1}$ to 15 mg mL$^{-1}$, for instance, from 5 mg mL$^{-1}$ to 15 mg mL$^{-1}$. In order for a bilayer to form at an interface, the concentration of amphipathic molecules is usually equal to or greater than 1 mg mL$^{-1}$, for instance equal to or greater than 5 mg mL$^{-1}$.

In other embodiments, the concentration of amphipathic molecules in the medium is from 0.5 to 10 mg mL$^{-1}$. Usually, the concentration of amphipathic molecules is from 5 to 10 mg mL$^{-1}$. The inventors have found that these concentration ranges are favourable for stabilising hydrogel networks that comprise at least one interface that comprises a bilayer of amphipathic molecules and at least one other interface that does not comprise a bilayer of amphipathic molecules. Likewise, these concentration ranges have been found to favour hydrogel networks which comprise at least one interface that comprises a bilayer of amphipathic molecules, and at least one other interface at which the hydrogel body of one hydrogel object is in direct contact with the hydrogel body of another hydrogel object. The concentration of the amphipathic molecules may therefore be from 5 to 10 mg mL$^{-1}$.

In a further embodiment, the concentration of amphipathic molecules in the medium is less than or equal to 5 mg mL$^{-1}$, for instance, less than or equal to 2 mg mL$^{-1}$. These concentration ranges often favour networks in which the interfaces do not comprise bilayers.

The hydrogel bodies are assembled into a said network or allowed to self-assemble into a said network.

When the hydrogel bodies are assembled into a said network, the step of assembling said hydrogel bodies into a said network usually comprises manipulation of a hydrogel body, or two or more hydrogel bodies, to form an assembly of the desired arrangement of the hydrogel objects. The manipulation usually comprises manipulation of a hydrogel body, or two or more hydrogel bodies, using a needle. Typically the needle is a metal needle such as a steel needle.

When the hydrogel bodies are allowed to self-assemble into a said network, the step of allowing said hydrogel bodies to self-assemble into a said network typically comprises agitating the hydrogel bodies in the medium. The rate at which the hydrogel bodies self-assemble into the network will, of course, depend upon the viscosity of the medium and the concentration of amphipathic molecules in the medium. As the viscosity of the medium and/or the concentration of amphipathic molecules increases, the rate of self-assembly typically decrease.

In some embodiments, the process comprises: introducing a plurality of hydrogel bodies into a medium comprising a plurality of amphipathic molecules; assembling said hydrogel bodies into a said network; and allowing said hydrogel bodies to self-assemble into a said network.

In some embodiments, the process further comprises pushing together any two of said plurality of hydrogel objects in order to form an interface between said any two hydrogel objects which does not comprise a bilayer of amphipathic molecules. It is thought that the pushing together any two of said plurality of hydrogel objects effectively squeezes out the bilayer of amphipathic molecules at the interface and/or prevents a bilayer from forming at the interface in the first place or from re-forming at the interface. Thus, in these embodiments, the process produces a network comprising at least one interface that does not comprise a bilayer of amphipathic molecules. The skilled person will appreciate that any network defined herein that comprises at least one interface that does not comprise a bilayer of amphipathic molecules could be produced by this process.

The process may, for instance, further comprise pushing together any two of said plurality of hydrogel objects in order to form an interface between said any two hydrogel objects at which the hydrogel bodies of the two hydrogel objects are in direct contact with each other. Thus, the process may be used to produce a network comprising at least one interface at which the two hydrogel bodies at that interface are in direct contact with each other. The skilled person will appreciate that any network herein defined that comprises at least one interface at which the hydrogel objects at that interface are in direct contact with each other could be produced by this process.

In other embodiments, the process further comprises pulling apart any two of said plurality of hydrogel objects in order to form a bilayer of amphipathic molecules an interface between said two contacting hydrogel objects.

In some embodiments, when the hydrogel network comprises at least two interfaces, the process comprises: (i) pushing together the two hydrogel objects at the first interface in order to form an interface between said hydrogel objects which does not comprise a bilayer of amphipathic molecules; and (ii) pulling apart the two hydrogel objects at the second interface in order to form an interface between said any two hydrogel objects which comprises a bilayer of amphipathic molecules. For instance, the process may comprise: (i) pushing together the two hydrogel objects at the first interface in order to form an interface at which the two hydrogel bodies are in direct contact; and (ii) pulling apart the two hydrogel objects at the second interface in order to form an interface between said any two hydrogel objects which comprises a bilayer of amphipathic molecules.

In some embodiments, the process further comprises pushing together or pulling apart any two of said plurality of hydrogel objects in order to adjust the size of the bilayer at any of said interfaces. (FIG. 5 of WO 2014/064459 provides an illustration of what typically happens to the size of the bilayer when the any two of said plurality of hydrogel objects are pushed together or pulled apart.) In these embodiments, the bilayer of amphipathic molecules is not completely squeezed out at the interface and the process produces a network comprising at least one interface that comprises a bilayer of amphipathic molecules. The skilled person will appreciate that any network defined herein that comprises at least one interface that comprises a bilayer of amphipathic molecules could be produced by this process.

In some embodiments, when the hydrogel network comprises at least two interfaces, the process comprises: (i) pushing together the two hydrogel objects at the first interface in order to adjust the size of the bilayer at the first interface; and (ii) pulling apart the two hydrogel objects at the second interface in order to adjust the size of the bilayer at the second interface.

The process of the invention may further comprise adjusting the distance between any two of said hydrogel objects to: (a) form a bilayer of amphipathic molecules at the interface between said two hydrogel objects; (b) remove a bilayer of amphipathic molecules from the interface between said two hydrogel objects; or (c) change the area of the bilayer at the interface between said two hydrogel objects. In other embodiments, the process of the invention may further comprise adjusting the distance between any two of said hydrogel objects to adjust the size of the bilayer at the interface between said two hydrogel objects.

Usually, the distance between said any two hydrogel objects is adjusted using a micromanipulator.

In some embodiments, the concentration of the amphipathic molecules in said medium is adjusted in order to control the presence or absence of a bilayer of amphipathic molecules at the or each said interface.

As mentioned above, the concentration of amphipathic molecules required for the formation of a bilayer at an interface may depend upon the size and shape of the hydrogel body. Thus, the adjustment made to the concentration of the amphipathic molecules in said medium in order to control the presence or absence of a bilayer of amphipathic molecules at said interface will usually depend on the size and shape of the hydrogel bodies at that interface.

In some embodiments, when the concentration of the amphipathic molecules in said medium is adjusted in order to control the presence or absence of a bilayer of amphipathic molecules at said interface:

(i) the concentration of amphipathic molecules is adjusted from being greater than x to being less than or equal to x;
(ii) the concentration of amphipathic molecules is adjusted from being less than y to being equal to or greater than y;
(iii) the concentration of amphipathic molecules is adjusted from being less than or equal to x to being greater than x but less than y; or
(iv) the concentration of amphipathic molecules is adjusted from being equal to or greater than y to being greater than x but less than y;
wherein x is 0.5 mg mL$^{-1}$, and y is 10 mg mL$^{-1}$.
x may, for instance, be 1 mg mL$^{-1}$ or 2 mg mL$^{-1}$. In some embodiments, x is 5 mg mL$^{-1}$.

In the process of the invention, the medium may, for instance, be a hydrophobic medium. The hydrophobic medium may, for instance, be a hydrophobic medium as defined hereinabove.

In one embodiment, the process of the invention further comprises introducing a volume of the hydrophobic medium, with the hydrogel network disposed therein, into a bulk hydrophilic medium, in the presence of amphipathic molecules. The volume may be a drop of the hydrophobic medium.

The bulk hydrophilic medium may, for instance, be an aqueous medium.

The process may therefore be used to form an encapsulate comprising a hydrogel network of the invention. Typically, the encapsulate comprises a volume (for instance a drop) of a hydrophobic medium; a peripheral layer of amphipathic molecules around the surface of the volume; and the hydrogel network within the peripheral layer. The amphipathic molecules which form the peripheral layer of the encapsulate may, in the process of the invention, be provided in the hydrophobic medium or in the bulk hydrophilic medium.

The process for producing a network of hydrogel objects, wherein the hydrogel objects are as defined herein, may further comprise recovering said network of hydrogel objects.

The invention also provides a network of hydrogel objects which is obtainable by a process as defined herein.

The invention also provides the use of an aqueous object/droplet assembly as defined herein in synthetic biology.

Further provided is the use of an aqueous object/droplet assembly as defined herein in preparing a protocell or an aggregate of protocells.

Also provided by the invention is the use of an aqueous object/droplet assembly as defined herein as a communication network or as part of a communication network.

For instance, the aqueous object/droplet assembly may comprise a first plurality of aqueous structures/droplets and a second plurality of aqueous structures/droplets, wherein the aqueous structures/droplets in the first plurality of aqueous structures/droplets are in communication with one another via the membrane proteins. Typically, the aqueous structures/droplets in the second plurality of aqueous structures/droplets are not in communication with one another via the membrane proteins.

The invention also provides the use of an aqueous object/droplet assembly as defined herein to store energy.

Droplet 3D Printer Overview: A description of an example of an apparatus for generating droplets (e.g. a 3D-printer of droplet networks) can be found in Villar et al, Science 340, 48-52 (2013). In brief, the droplet generator (which may be referred to as "piezo") comprised a piezoelectric disc which seals the back of an aqueous chamber with a protruding tapered capillary nozzle. The piezo can eject droplets from the nozzle upon application of a square-wave voltage pulse when the tip is submerged in a bulk hydrophobic medium such as a lipid-in-oil solution. An electronic micromanipulator was used to move the printing stage, e.g. an oil container, in three dimensions. This in combination with lab-designed printing software that interprets "printing maps" and automates droplet ejection, allowed the construction of 3D droplet networks by successive layering of spatially assigned droplets.

The present invention is further illustrated in following Example. The Example is not limiting on the scope of the invention.

Example

The inventors have previously used 3D printing to prepare tissue-like materials in which picoliter aqueous compartments are separated by lipid bilayers. In the present work, these printed droplets are elaborated into synthetic cells by using a tightly regulated in vitro transcription/translation system. A light-activated DNA promoter has been developed that can be used to turn on expression of any gene within the synthetic cells. The inventors used light activation to express protein pores in 3D printed patterns through synthetic tissues. The pores are incorporated into specific bilayer interfaces, and thereby mediate rapid, directional electrical communication through the cells. Accordingly, the inventors have developed a functional mimic of neuronal transmission that can be controlled in a precise way.

No systems have been created where multiple soft encapsulated synthetic cells can communicate with each other, although patterned 2D solid-state microfluidic chambers containing cell-free expression medium can communication through diffusion (10). Furthermore, no light-based method has been developed that can control protein expression inside synthetic cells. Here, the inventors have created, inter alia, 3D synthetic tissues made up of hundreds of synthetic cells, using a droplet-in-oil 3D printer (11). Additionally, the inventors have developed a tightly regulated light-activated DNA promoter. By using these technologies in combination, light-activated electrical communication through the synthetic tissues has been achieved by expressing a transmembrane pore, α-hemolysin (αHL), in a subset of the synthetic cells, 3D printed to form a conductive pathway that is a functional mimic of neuronal transmission.

Figure 1B:
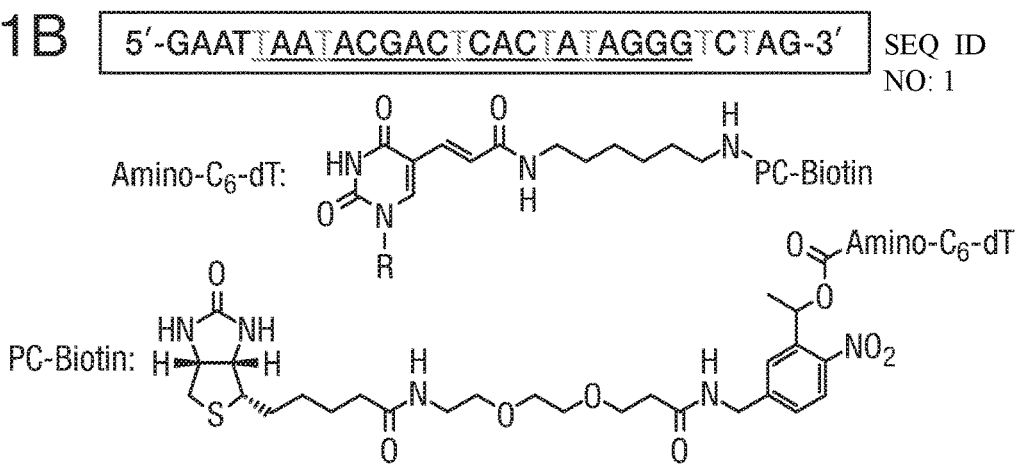
Figure 2:
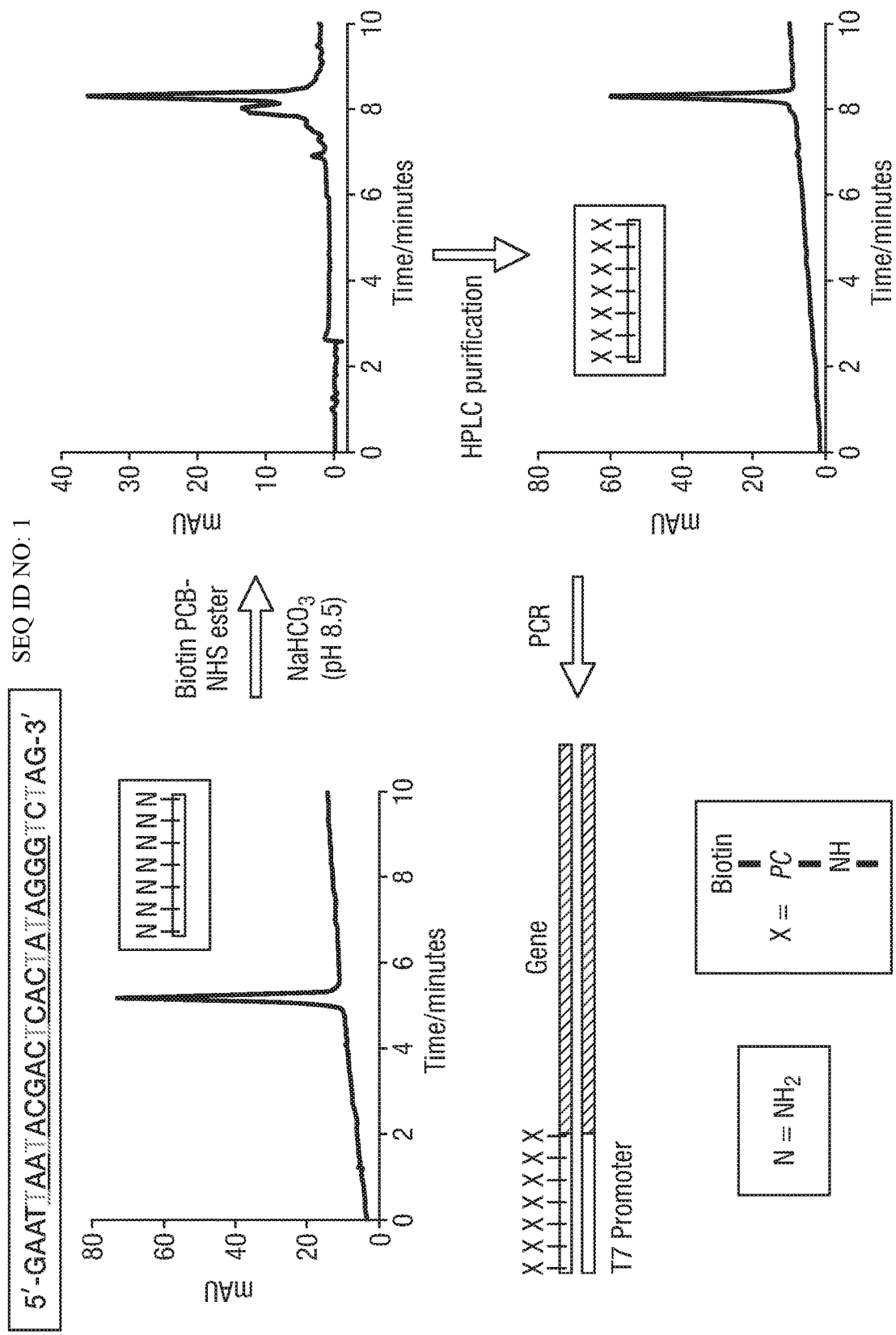
FIG. 2 shows synthesis of LA-DNA from an amino-T7 primer. The oligo containing seven C6-amino-dT modifications was reacted with NETS-ester PC Biotin and purified by HPLC. The Oligo PC Biotin conjugate was used as a PCR primer to create a DNA template to express a gene of interest. HPLC signal is 260 nm absorbance.
Figure 3:
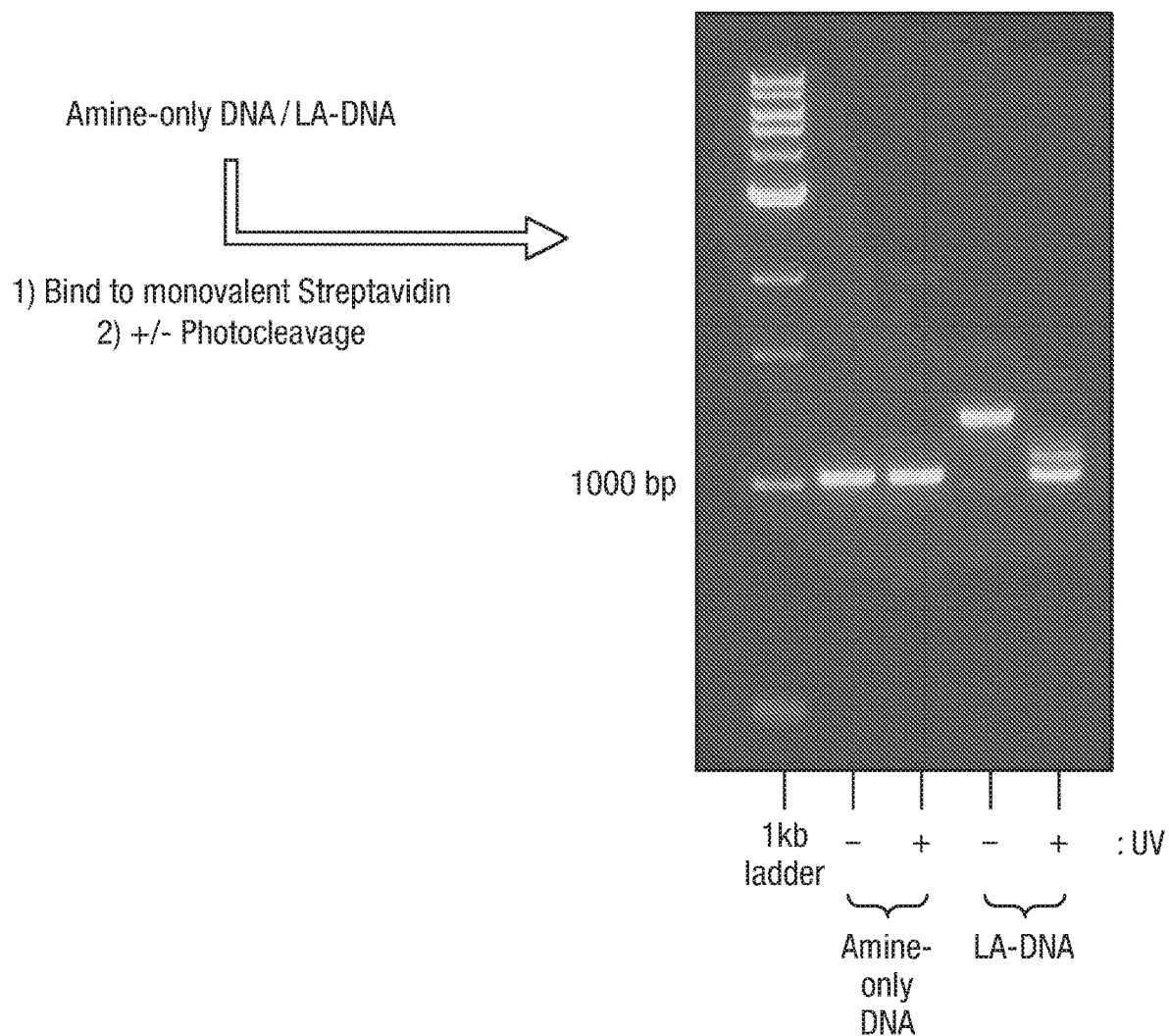
FIG. 3 shows binding of monovalent streptavidin and photocleavage of LA-DNA. Amine-only DNA and LA-DNA were both incubated with monovalent streptavidin. Monovalent streptavidin only bound to the LA-DNA as seen in the gel shift. Upon UV illumination, the LA-DNA was reduced to the same apparent mass as the amine-only DNA, by photocleavage of the PC/biotin/streptavidin from the DNA.

Light activated transcription and/or translation has been achieved previously, however these systems either do not fully repress transcription in the off state (12) or they cannot be encapsulated inside synthetic cells due to bursting of the lipid membranes (13, 14). The inventors sought to develop an improved, more efficient light-activated T7 promoter (LA-T7 promoter) that could be placed upstream of any gene of interest, so that no expression would occur until the DNA was illuminated (FIG. 1A). An efficient "off-state" is required so that no protein expression, and therefore no function, is observed without activation. To achieve this, C6-amino-dT modified bases were incorporated across a single-stranded T7 promoter DNA sequence (FIG. 1B). A photocleavable (PC) biotin NETS-ester linker (15) was coupled to all the amines (FIG. 2) so that, when the modified DNA was used as a PCR primer with a gene of interest, PC biotin moieties would protrude from the major groove at the T7 polymerase binding site (FIG. 1A). The PC group was 2-nitrobenzyl, which allows rapid and efficient cleavage back to the original primary amine (15) to leave minimal scarring of the T7 promoter and allow similar expression to a unmodified T7 promoter. The light-activated DNA (LA-DNA) was created by the addition of monovalent streptavidin (16) to the double-stranded DNA PCR product so that each biotin in the T7 promoter bound to a single monovalent streptavidin molecule (FIG. 3). As a fully "photocleaved" control, the inventors used amine-only DNA; only the C6-amino groups are present in the T7 promoter, which lacks PC biotin and therefore does not bind streptavidin. The inventors observed rapid and efficient photocleavage of the monovalent streptavidin, biotin and linker group from the LA-DNA under 365 nm UV light, as measured by gel electrophoresis (FIG. 3). No binding of streptavidin was observed for the amine-only DNA (FIG. 3).

Figure 1C:
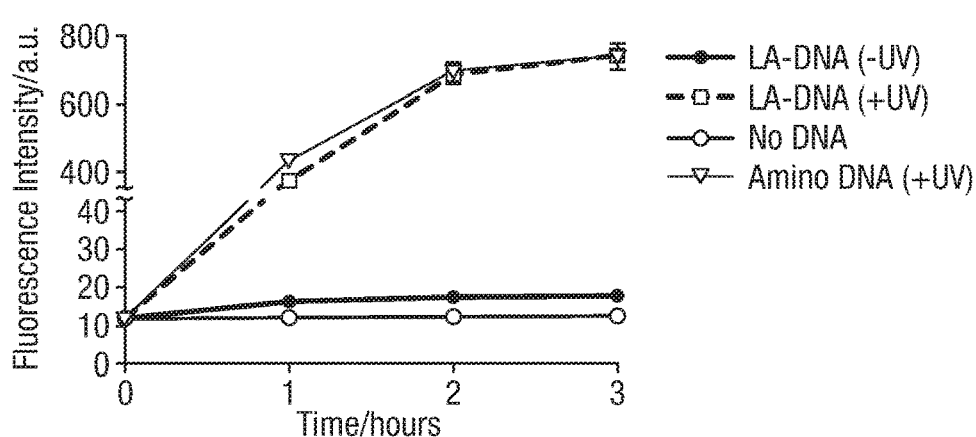
Figure 4:
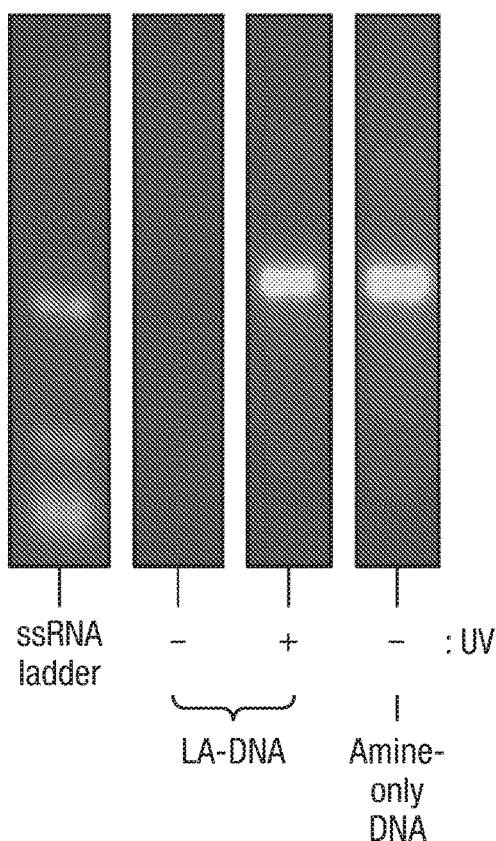
FIG. 4 shows T7 RNA transcription from LA-DNA. Amine-only DNA and LA-DNA were pre-incubated with monovalent streptavidin. Each DNA was used as a template for T7 RNA transcription. Without UV light, no RNA was produced from LA-DNA. With UV light, similar amounts of RNA were observed for LA-DNA and amine-only DNA.

For cell-free expression of proteins, the inventors used the PURE system (17), which contains the minimal bacterial components required for protein expression (18). T7 RNA polymerase alone was used for transcription only. For initial experiments, the LA-T7 promoter was placed upstream of the yellow fluorescent protein mVenus. RNA transcription (FIG. 4) of LA-mVenus DNA and protein expression (FIG. 1C), from this LA-DNA, demonstrated there was minimal transcription/expression from the "off-state" and that the "on-switch" was highly effective (>130 fold increase in expression from off- to on-state after normalising to no DNA). No inhibitory effects from the monovalent streptavidin or the photocleaved linker and biotin were observed by comparison with the amine-only DNA (FIG. 1C). This demonstrates that the LA-DNA technology tightly regulates transcription of DNA by T7 polymerase.

Figure 5A:
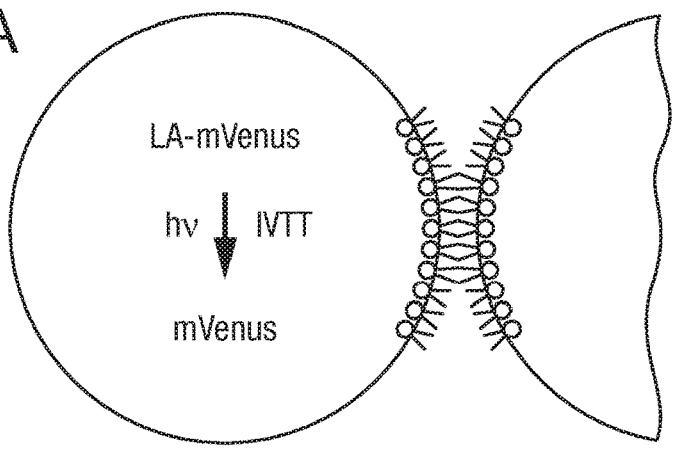
FIG. 5 shows light-activated expression of LA-mVenus in synthetic cells and synthetic tissues. (A) Schematic of a synthetic cell that will express mVenus protein upon light activation, where a single bilayer connects it to a neighbouring synthetic cell. (B) Synthetic cells containing LA-mVenus DNA express mVenus protein (white/light-grey) upon light activation. (C) Fluorescence intensity line profile of B. Top line is +UV and bottom line next to X-axis is -UV. (D) Schematic of 3D-printed synthetic tissues containing hundreds of synthetic cells. A single lipid bilayer, as shown in A, connects each cell with its neighbour. (E) Synthetic tissues containing LA-mVenus DNA express mVenus protein (white/light-grey) upon light activation. (F) Fluorescence intensity line profile of E. Top line is +UV and bottom line next to X-axis is -UV.
Figure 5B:
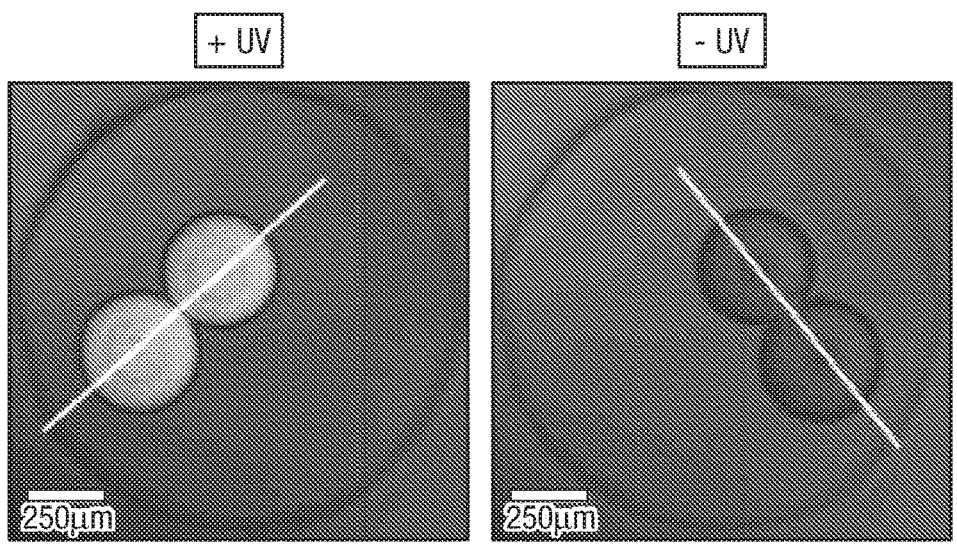
Figure 5C:
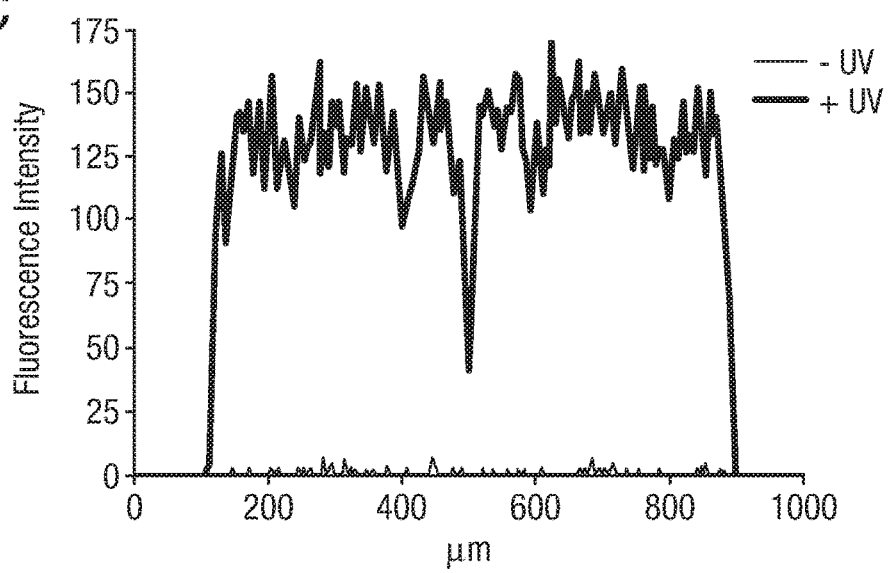
Figure 6A:
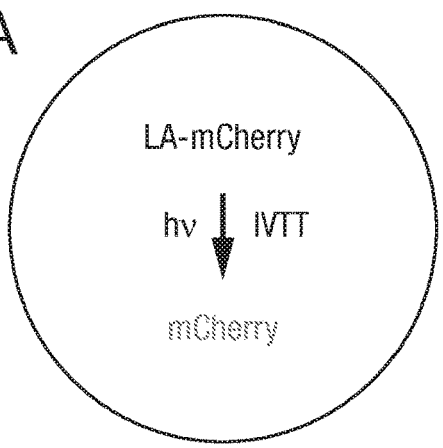
FIG. 6 shows light activated expression of LA-mCherry protein in synthetic cells. (A) Schematic of a synthetic cell that will express mCherry protein (white/light-grey) upon light activation. The -UV cells do not express mCherry. (B) Synthetic cells containing LA-mCherry DNA expressed mCherry upon light activation. (C) Fluorescence intensity line profile of B. Top line is +UV and bottom line next to X-axis is -UV.
Figure 6B:
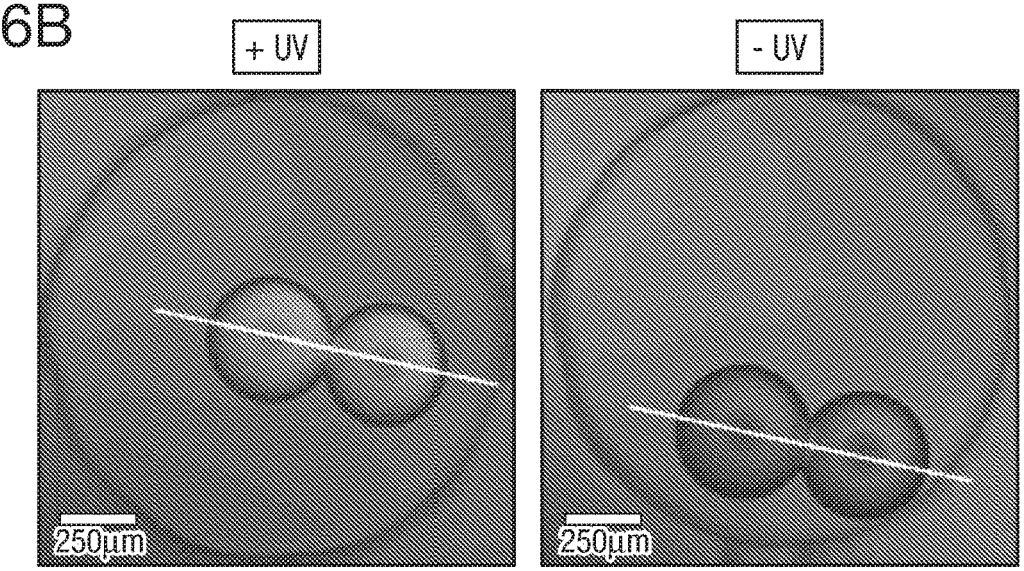
Figure 6C:
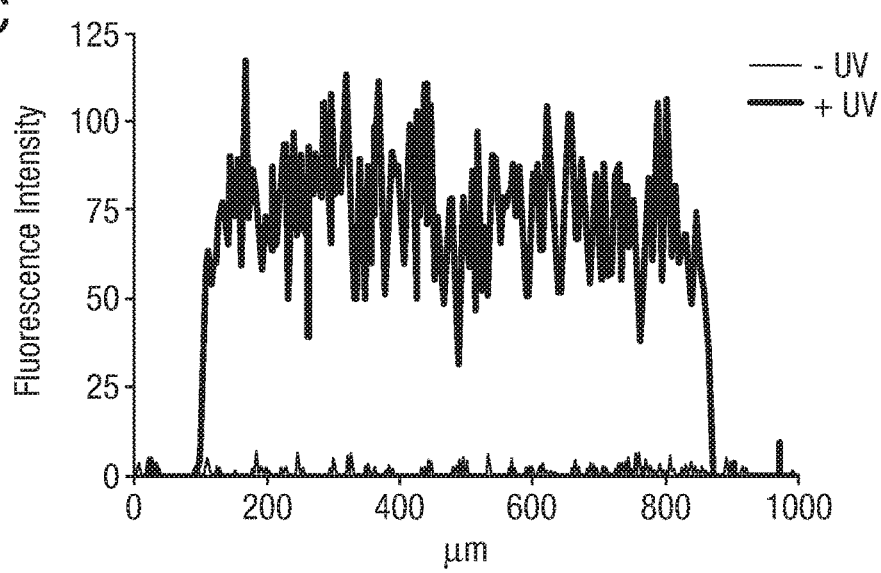

To create synthetic cells, the PURE system components were mixed with LA-DNA and the mix was encapsulated in lipid-coated water-in-oil droplets (FIGS. 5A and 6). Lipid-coated aqueous droplets in oil can be brought together to form a droplet interface bilayer (DIB) (19), which mimics the bilayer of a cell membrane. Networks of droplets joined by DIBs have been utilised previously as soft biodevices (20-22). DIB formation and stability between droplets that contain complex biological components has been a hurdle to the creation of more complicated networks and biodevices (23). The high concentration of protein inside the droplets can, in certain instances, promote droplet fusion. The inventors have developed novel optimised lipid compositions, e.g. a mixture of 10 or 15% DPPE-mPEG2000 in DPhPC, which allows long-term bilayer stability in the presence of PURE components without affecting their function, as demonstrated by the light-activated expression of mVenus (FIGS. 5B and C) and a red fluorescent protein, mCherry (FIG. 6). UV light had no effect on the expression of amine-only mVenus DNA in synthetic cells (FIG. 7).

Figure 9A:
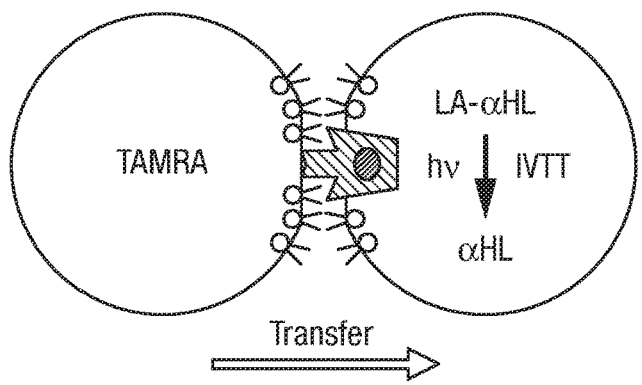
FIG. 9 shows light-activated transfer of a small-molecule fluorophore between synthetic cells. (A) Schematic of the synthetic cell pair. One cell contained LA-αHL DNA, the other contained the small-molecule fluorophore TAMRA. TAMRA diffused across the bilayer only when αHL was expressed and permeabilized the membrane. (B) Diffusion of TAMRA across the bilayer was only observed after light activation. For −UV, the left synthetic cell is TAMRA positive and the right synthetic cell is TAMRA negative. For +UV, TAMRA has diffused from the left to right synthetic cell and so both are TAMRA positive. (C) Fluorescence intensity line profile of B. The −UV line has the higher fluorescence intensity up to about 400 μm and is then near the X-axis. The +UV line has the lower fluorescence intensity up to about 400 μm and is then the higher line sitting above about 50 on the Y-axis.
Figure 9B:
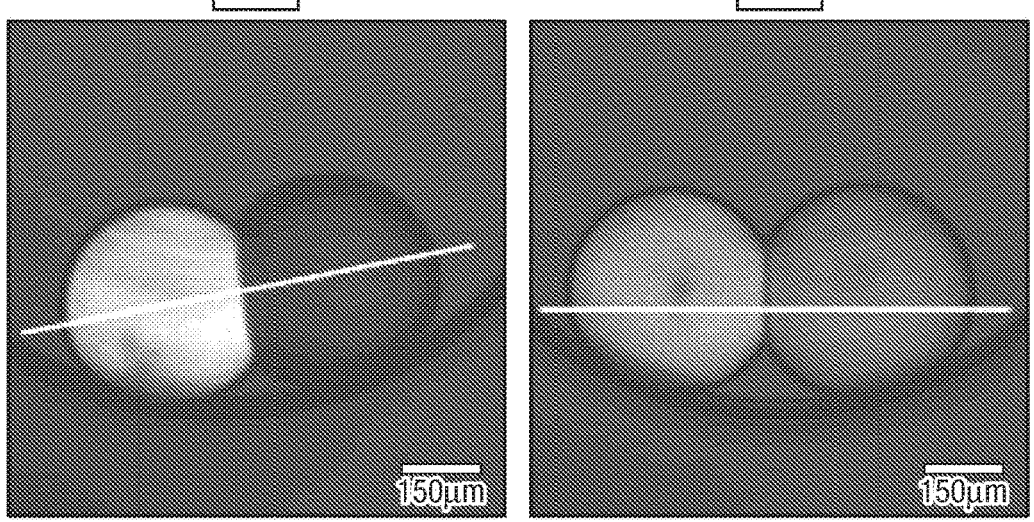
Figure 9C:
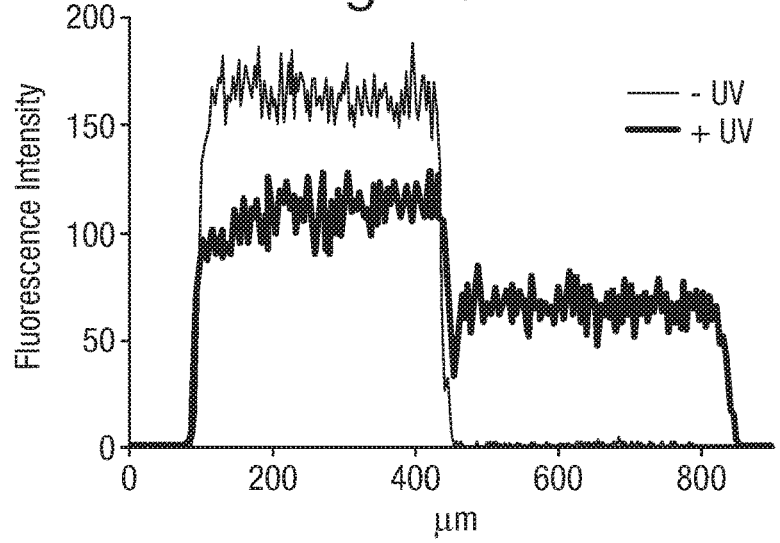

The gene encoding the heptameric membrane protein pore αHL was then placed downstream of the LA-T7 promoter and expressed in one droplet of a pair forming a DIB. As expected, αHL localised to the bilayer (FIG. 8). As two synthetic cells could now be interfaced and a membrane protein expressed, communication between the two cells was examined to demonstrate that the αHL was functional. Natural cells communicate with each other through small molecule effectors or electrical signals (24). The inventors first tested for light-activated diffusion of a small-molecule fluorophore between two synthetic cells, by insertion of αHL into the interface bilayer. Two synthetic cells were brought together; one contained a small molecule dye, TAMRA, with no DNA and the other LA-αHL DNA. Small molecule transfer between the two synthetic cells was achieved when they were illuminated, but no transfer was observed without illumination (FIG. 9). The small molecule dye could only translocate across the bilayer into the second droplet by diffusion if the αHL formed a pore in the interface bilayer. The inventors then tested for light-activated electrical signalling between two synthetic cells by electrical recording, following insertion of αHL into the bilayer. After forming a synthetic cell that contained LA-αHL DNA, it was activated by light, then an electrode was inserted into it and the cell was interfaced with another synthetic cell containing no DNA. Electrical communication, measured as an ionic current between the two synthetic cells, was achieved when the cell containing LA-αHL DNA had been illuminated, but no electrical signal was detected without illumination (FIG. 10). Electrical signals would only be transmitted between the synthetic cells if the αHL formed a functional pore in the membrane to allow ions to translocate in an applied potential. The communication between synthetic cells by a small molecule and by electrical signalling demonstrates that soft biological compartments can communicate with each other in a controlled manner.

Figure 5D:
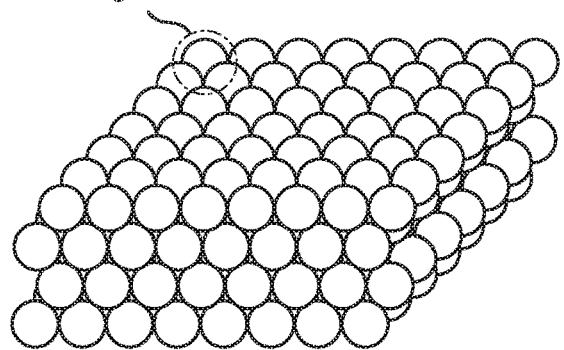
Figure 5E:
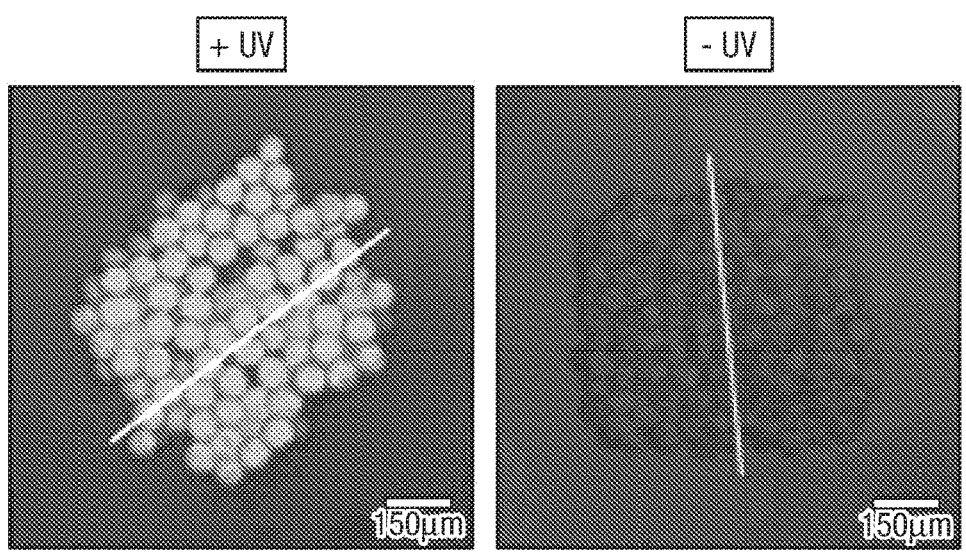
Figure 5F:
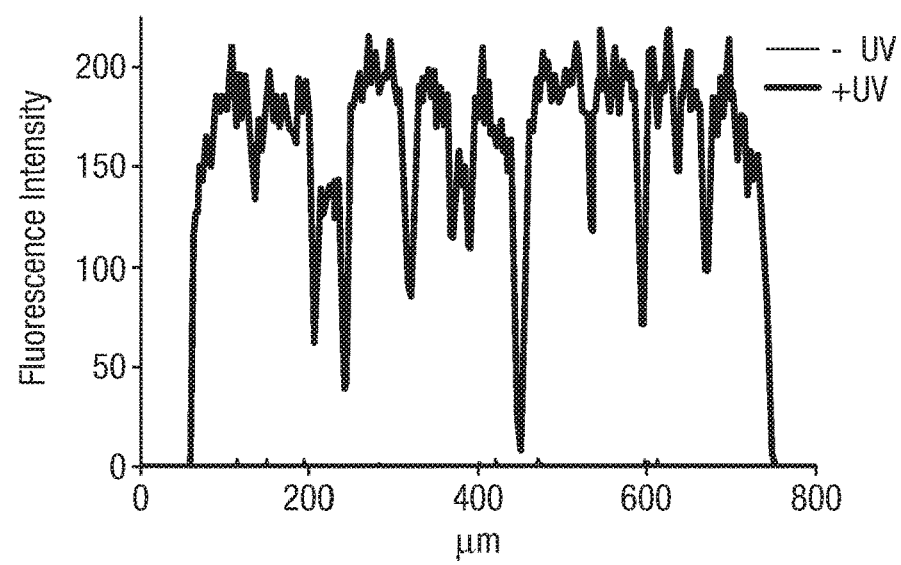
Figure 12A:
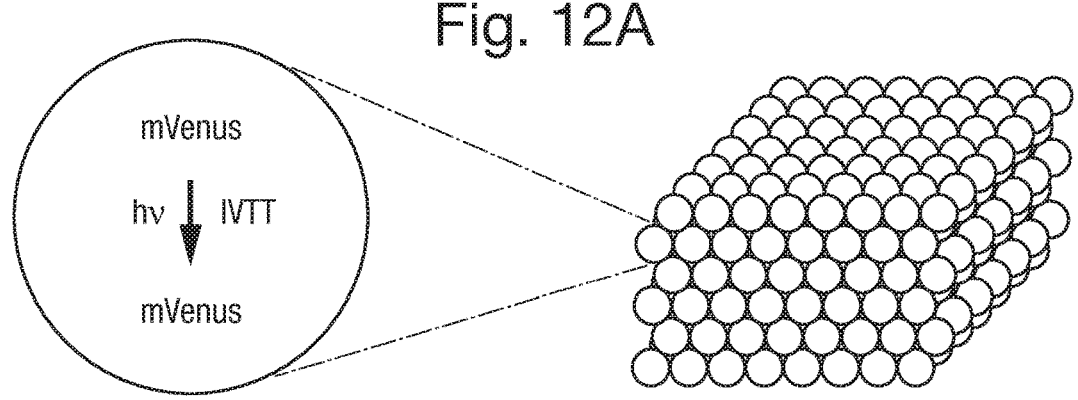
FIG. 12 shows expression from amine-only mVenus DNA in synthetic tissues. (A) Schematic of synthetic cells that will express mVenus protein with or without light activation. (B) Synthetic tissues containing amine-only mVenus DNA express mVenus (white/light-grey) with or without light activation. (C) Fluorescence intensity line profile of B. The +UV line is the line that has higher fluorescence intensity below about 200 μm and has higher fluorescence intensity above about 800 μm.
Figure 12B:
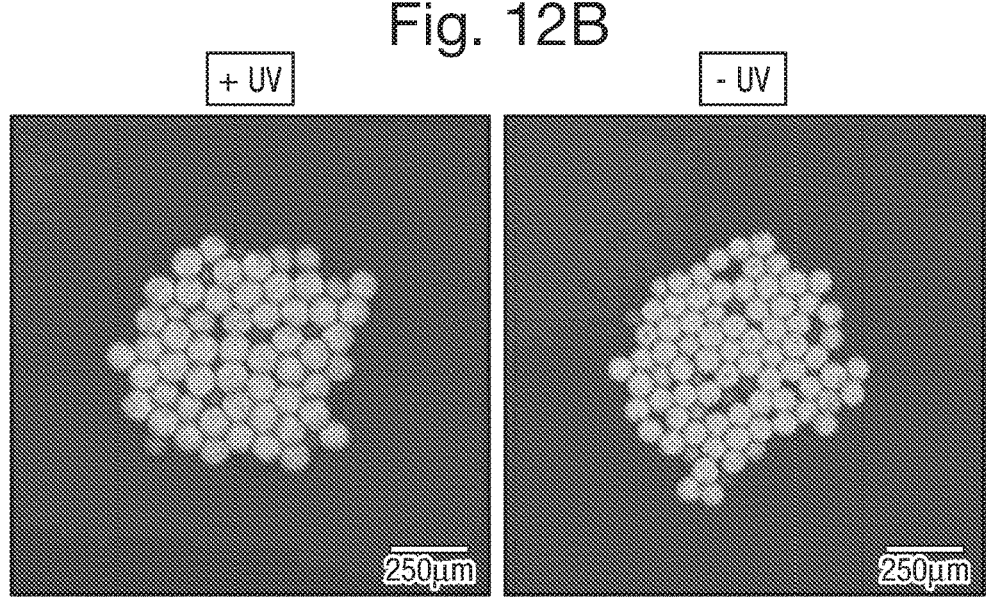
Figure 12C:
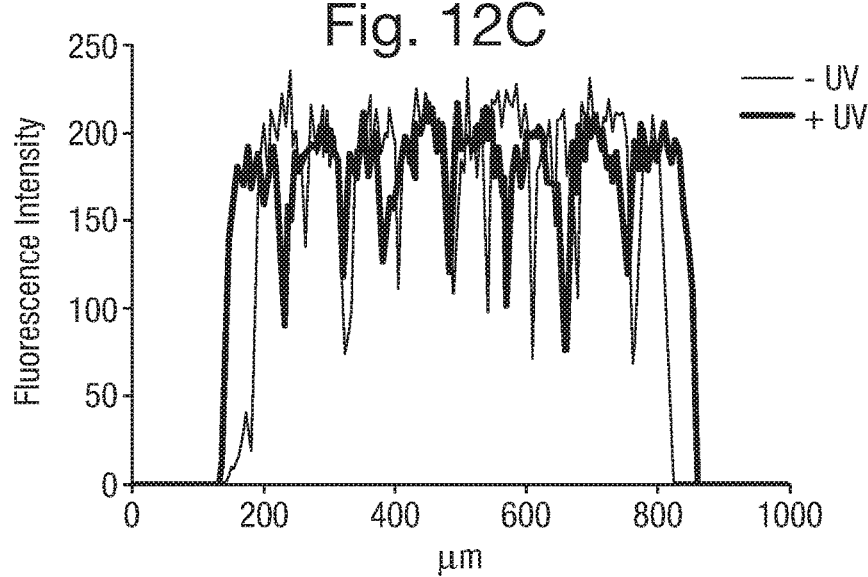
Figure 13:
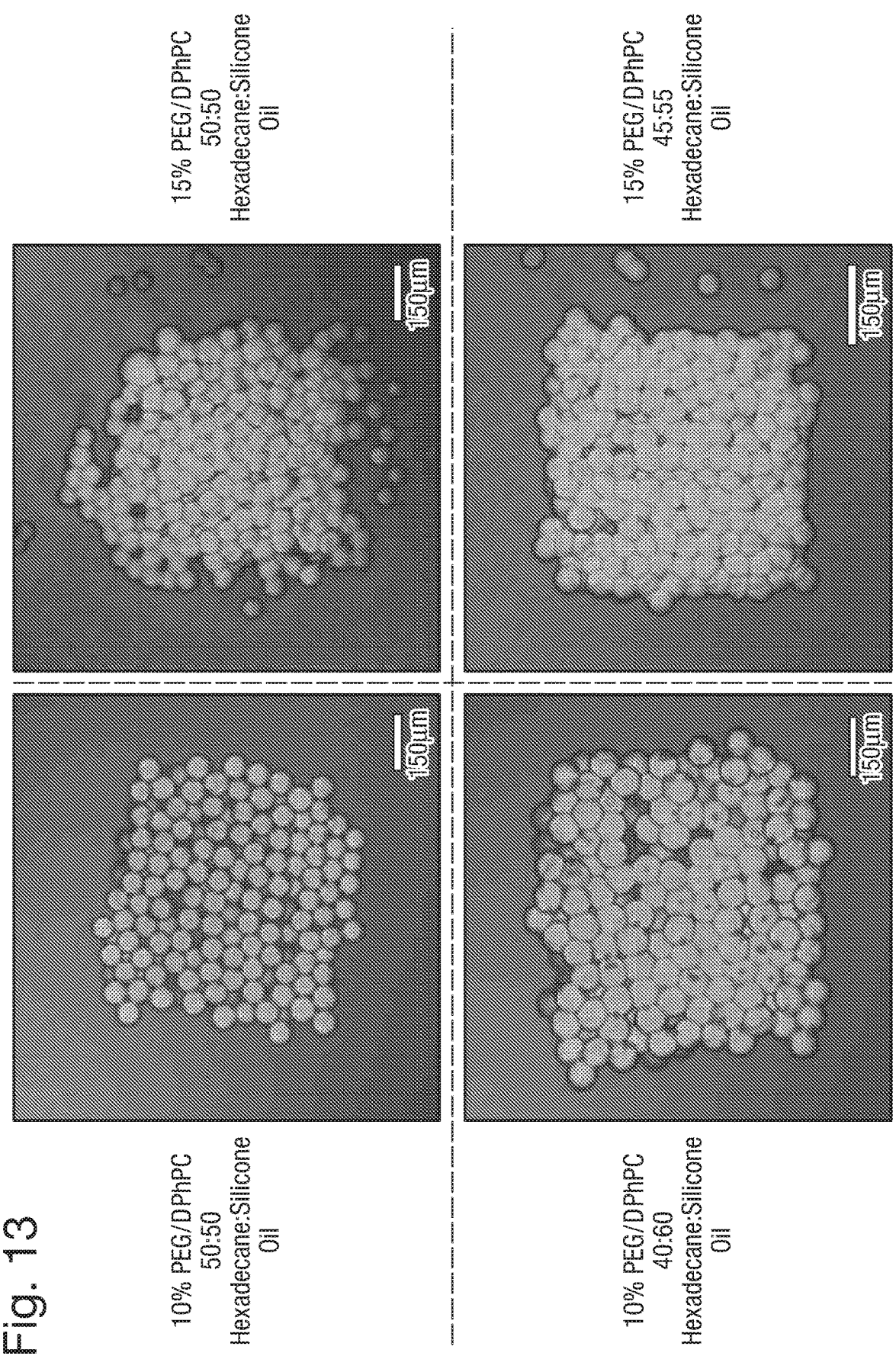
FIG. 13 shows tuning the packing of synthetic cells inside synthetic tissues, by altering the bilayer size between synthetic cells. By increasing the fraction of DPPE-mPEG2000 lipid or the silicone oil proportion, the bilayer size increases which causes the droplets in the synthetic tissue to pull each other closer together. The conditions shown in the bottom left panel (10% PEG, 40:60 hexadecane:silicone oil) were chosen for all further experiments, because of the close packing observed and because less leakage of the solution from the capillary occurred during printing.

The inventors have previously made a 3D printer for water-in-oil droplets, which can create complex 3D patterned functional soft structures composed of hundreds of aqueous compartments (11). Just as the inventors found for individual DIBs, the droplets that formed the 3D networks fused in the presence of complex biological mixtures. Using the inventors' optimised lipid mixtures, the inventors were able to print 3D cuboids, containing hundreds of synthetic cells, which are referred to as synthetic tissues (FIG. 5D). Once printed, expression from LA-DNA was observed inside these synthetic tissues if they were illuminated, but not without illumination (FIGS. 5E, F and 11). UV light had no effect on the expression of amine-only DNA in synthetic tissues (FIG. 12). It is important to be able to control the structure of the 3D printed synthetic tissues. Packing of the droplets inside 3D networks is a function of the area of the bilayer between the each droplet and can dictate network stability. The inventors found that they could tune the bilayer size and packing of the synthetic cells inside the synthetic tissues by altering the composition of the lipids and the oil, without affecting protein expression (FIG. 13).

In order to demonstrate electrical communication through synthetic tissues, synthetic cells that contained LA-αHL DNA were 3D printed into tissues and studied by electrical recording (FIG. 14A). Once printed, the synthetic tissues were illuminated to trigger αHL protein expression. Electrodes were then placed on either side of the synthetic tissue cuboid to measure electrical communication. Electrical communication through the synthetic tissues could be observed following illumination, but no electrical signal was detected without illumination (FIGS. 14B and C).

Figure 15A:
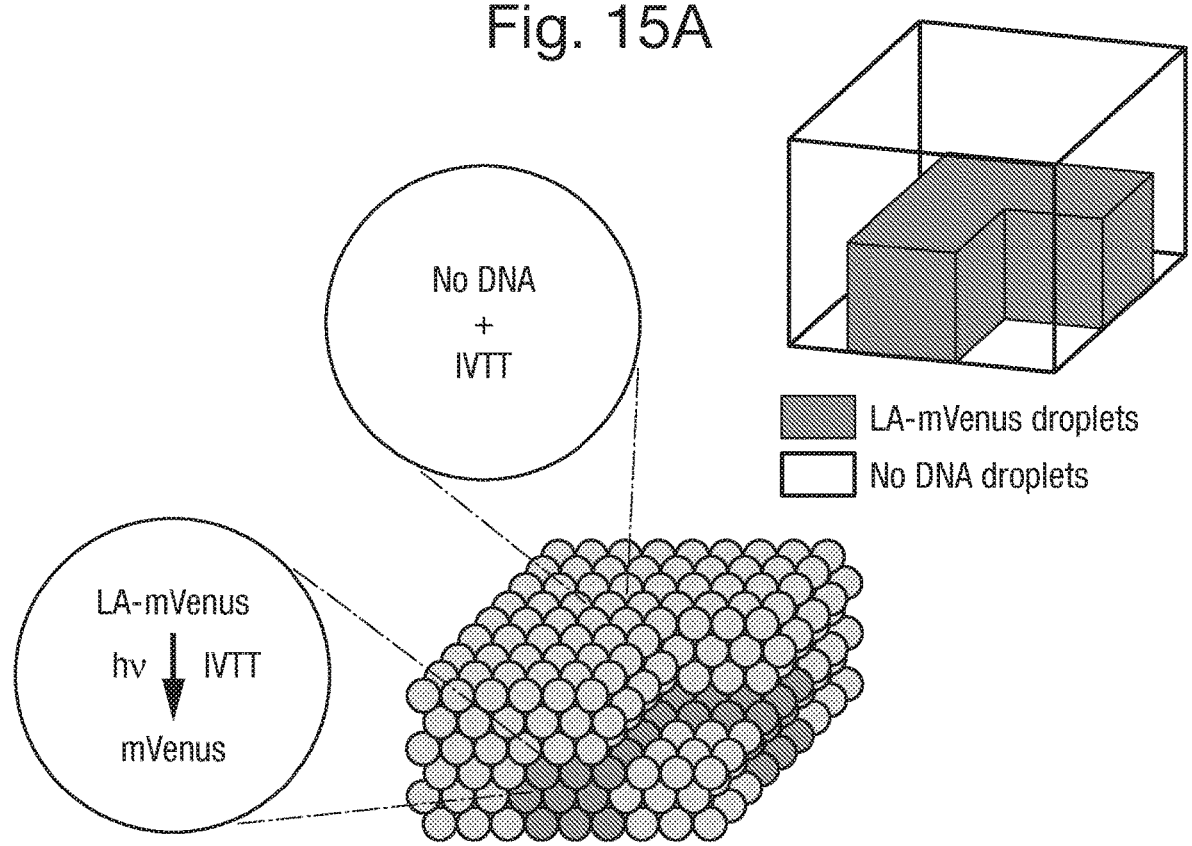
FIG. 15 shows Light-activated patterned expression of mVenus from LA-mVenus DNA in a 3D printed synthetic tissue. (A) Schematic showing a printed tissue with droplets containing LA-mVenus DNA (dark-grey) and droplets containing no DNA (light-grey). (B) After light activation, the mVenus-containing droplets become visible (yellow fluorescence shown as white/light-grey).
Figure 15B:
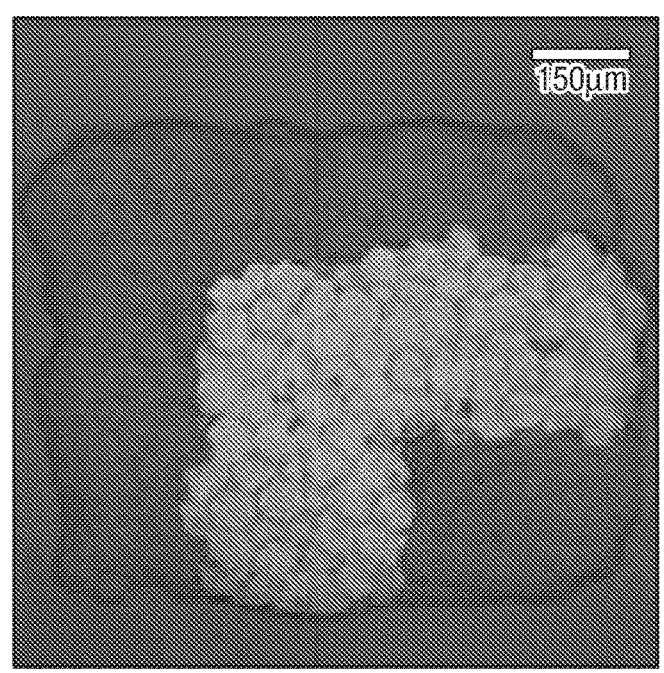
Figure 16A:
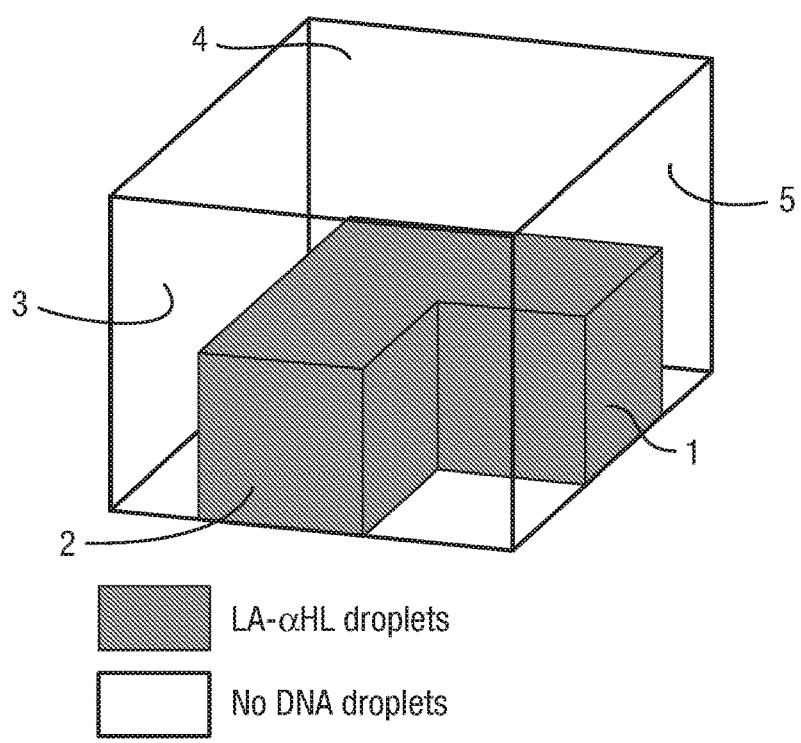
FIG. 16 shows electrical recordings from an L-shaped pathway formed by expression from LA-αHL DNA in a 3D-printed synthetic tissue. (A) Schematic of the printed tissue containing droplets with LA-αHL DNA (grey) printed with droplets containing no DNA (clear region within black frame). Numbers represent sides of the cuboid where electrodes were placed to detect the conductive pathway. Electrical recordings detect a current when the electrodes are at positions 1 and 2 (B), based on the voltage protocol below, but not when the electrodes are positioned at side 1 of the pathway and 3 (C), 4 (D) or 5 (E), or when both electrodes are positioned away from the pathway, 3 and 5 (F).
Figure 16B:
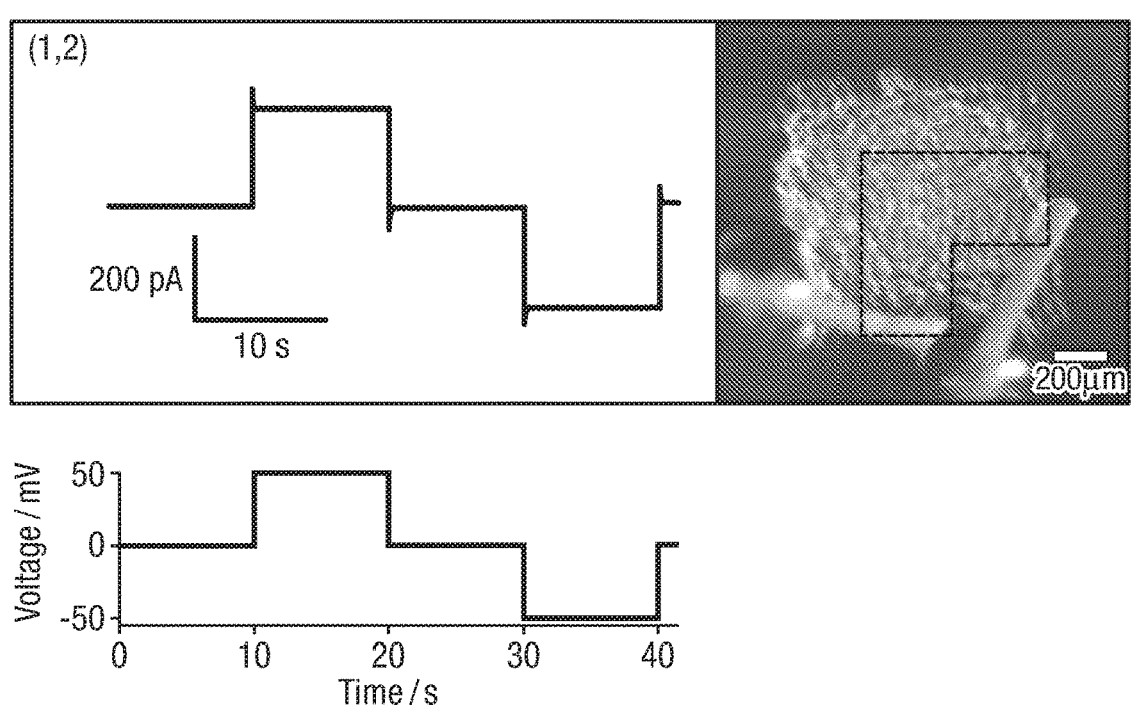
Figure 16C:
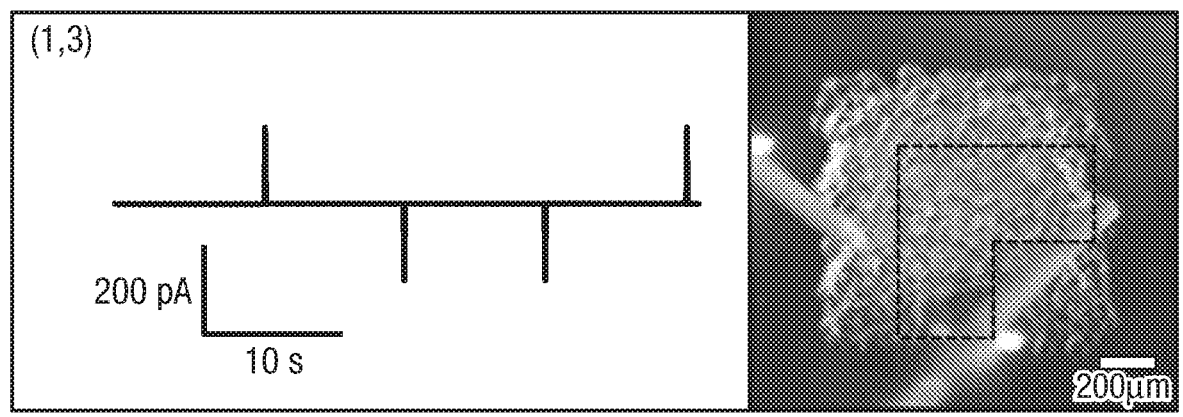
Figure 16D:
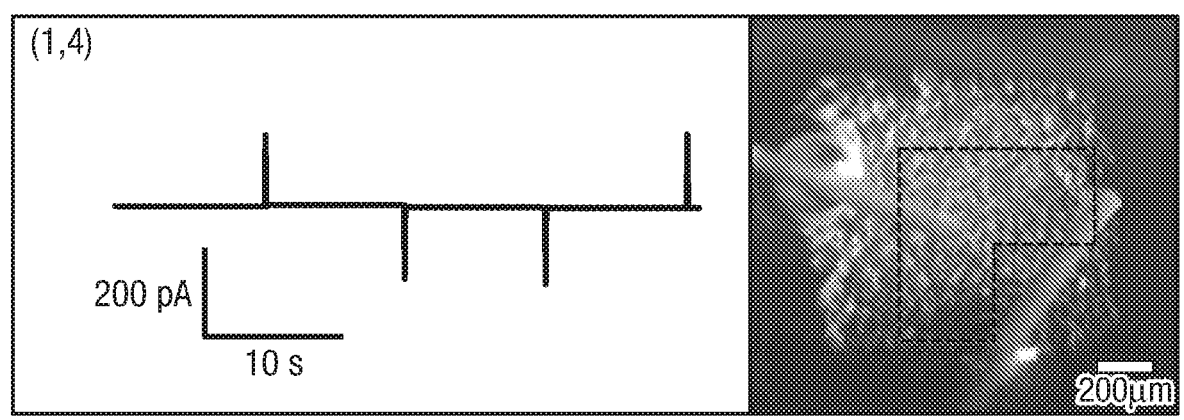
Figure 16E:
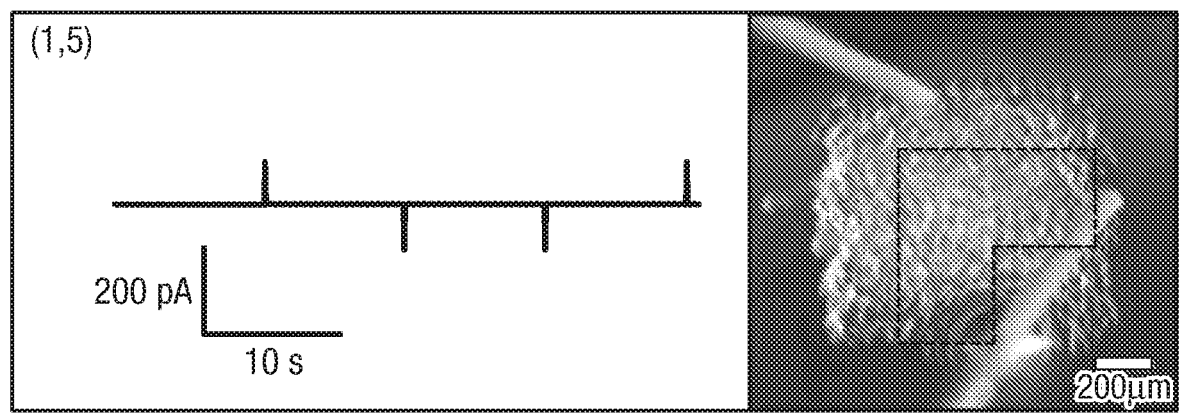
Figure 16F:
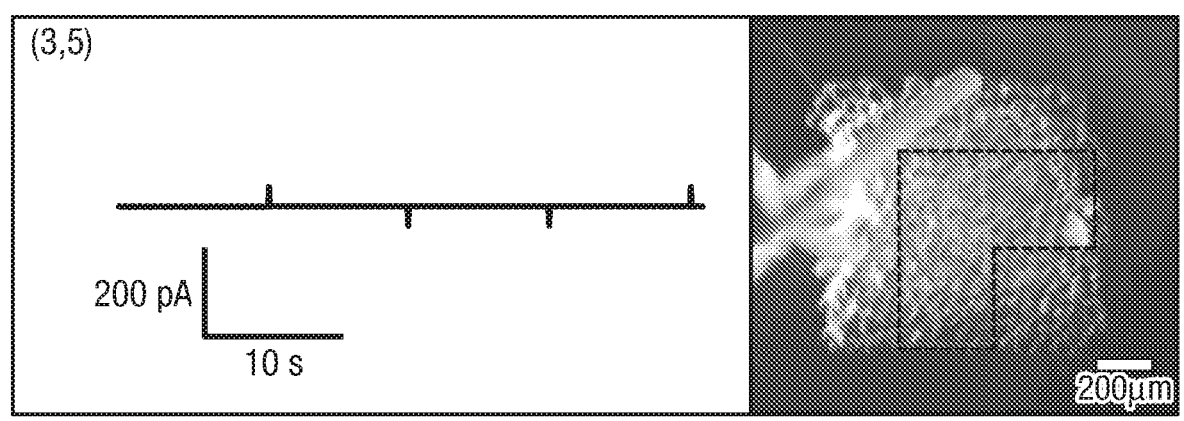

The inventors also aimed to take advantage of the patterning capabilities of the 3D printer. Patterning was first evaluated by printing synthetic cells containing LA-mVenus DNA in programmed arrangements within synthetic tissues comprising cells lacking DNA (FIG. 15). Directional 3D electrical communication through synthetic tissues was then tested by printing droplets containing LA-αHL DNA in defined 3D pathways within the tissues (FIG. 16A). Following printing, the synthetic tissues were illuminated and αHL protein expressed. Electrical communication was observed through the synthetic tissue by placing electrodes at the two ends of a pathway (FIG. 16B). When the electrodes were placed at other points on the synthetic tissue, no electrical signal was detected (FIG. 16C-F). In this way, the accuracy and versatility of the inventors' 3D printer has been used to fabricate a synthetic tissue in which an electrical communication pathway, analogous to rapid directional neuronal transmission, can be switched on by an external stimulus.

Figure 18A:
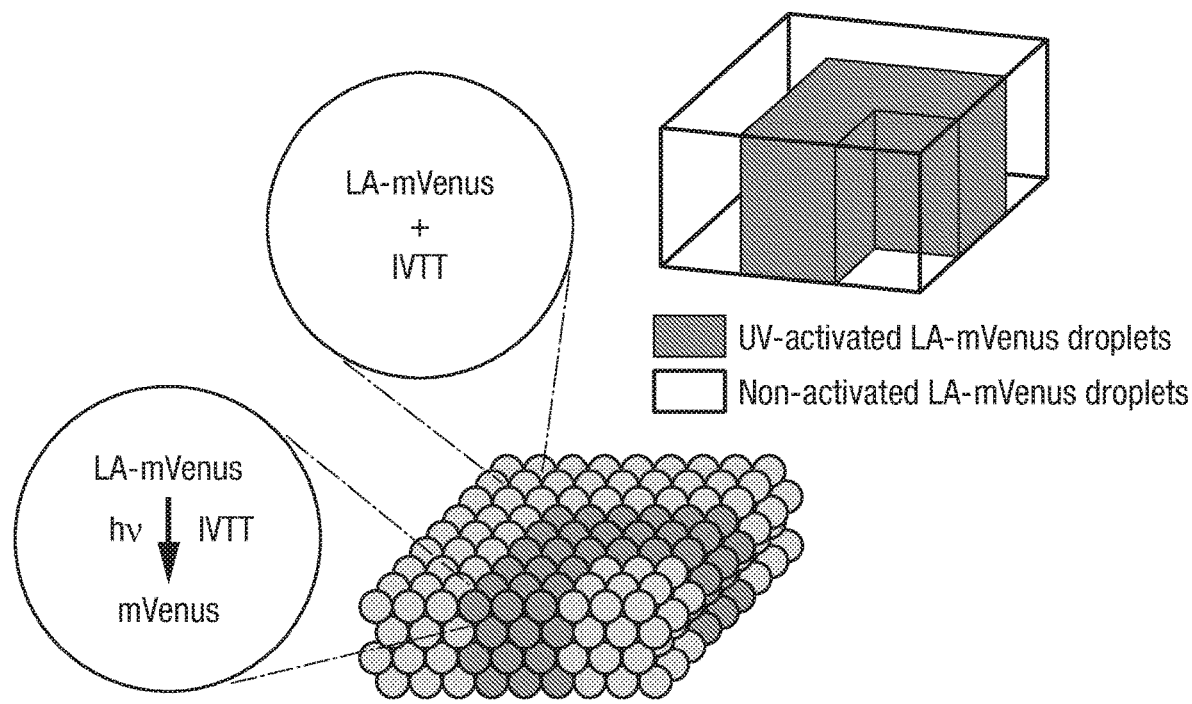
FIG. 18 shows light-activated mVenus protein expression in a light-patterned pathway. (A) Schematic showing a printed tissue with all droplets containing LA-mVenus DNA, but only those droplets that have been illuminated with the microscope express protein (dark-grey), while the rest do not (light-grey). (B) mVenus is only expressed in the light-activated droplets (yellow fluorescence shown as white/light-grey) illuminated by the microscope.
Figure 18B:
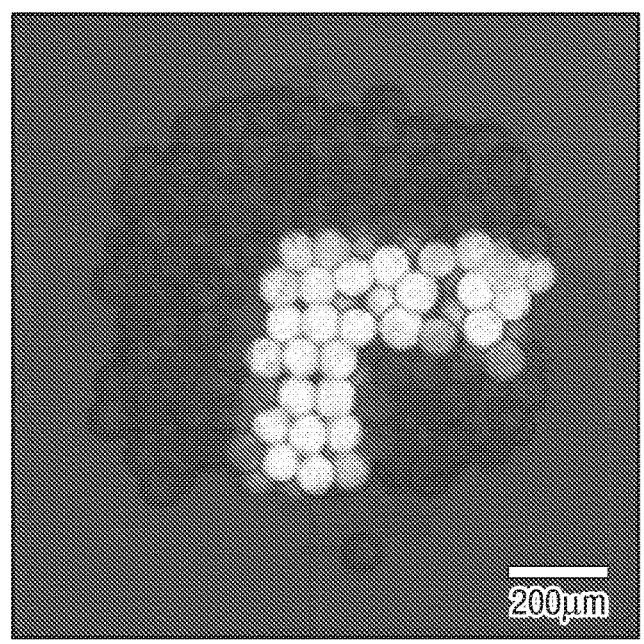
Figure 19A:
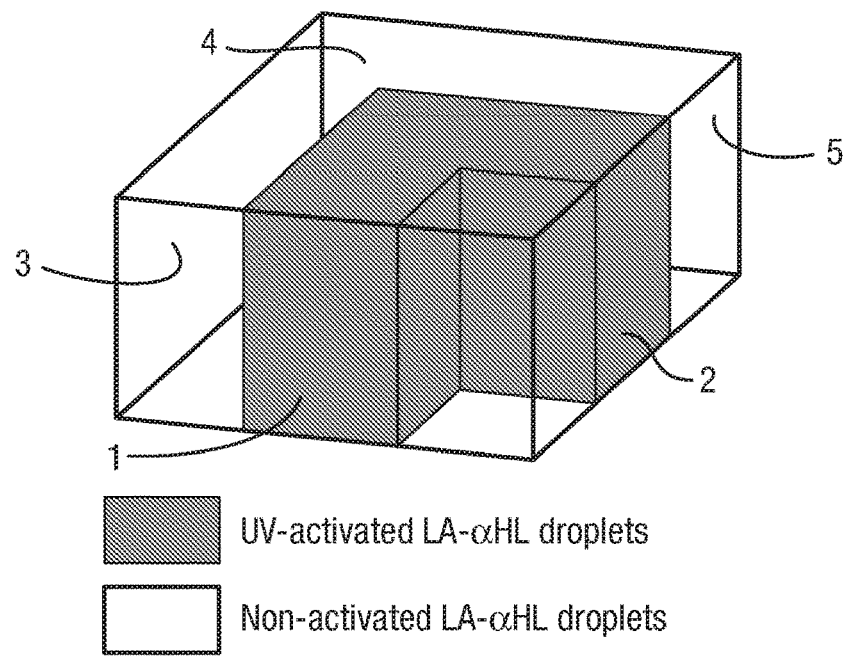
FIG. 19 shows electrical recordings from an L-shaped 2D pathway formed by light-patterning of an LA-αHL DNA 3D-printed synthetic tissue. (A) Schematic of the printed tissue where all droplets contain LA-αHL DNA, but only those illuminated with the microscope express protein (grey), while the rest do not (clear region within black frame). Numbers represent sides of the cuboid where electrodes were placed to detect the conductive pathway. Electrical recordings detect a current when the electrodes are at positions 1 and 2 (B), based on the voltage protocol below, and at 1 and 4 (D). No electrical signal is observed when the electrodes are positioned at side 1 of the pathway and 3 (C) or 5 (E), or when both electrodes are positioned away from the pathway, 3 and 5 (F).
Figure 19B:
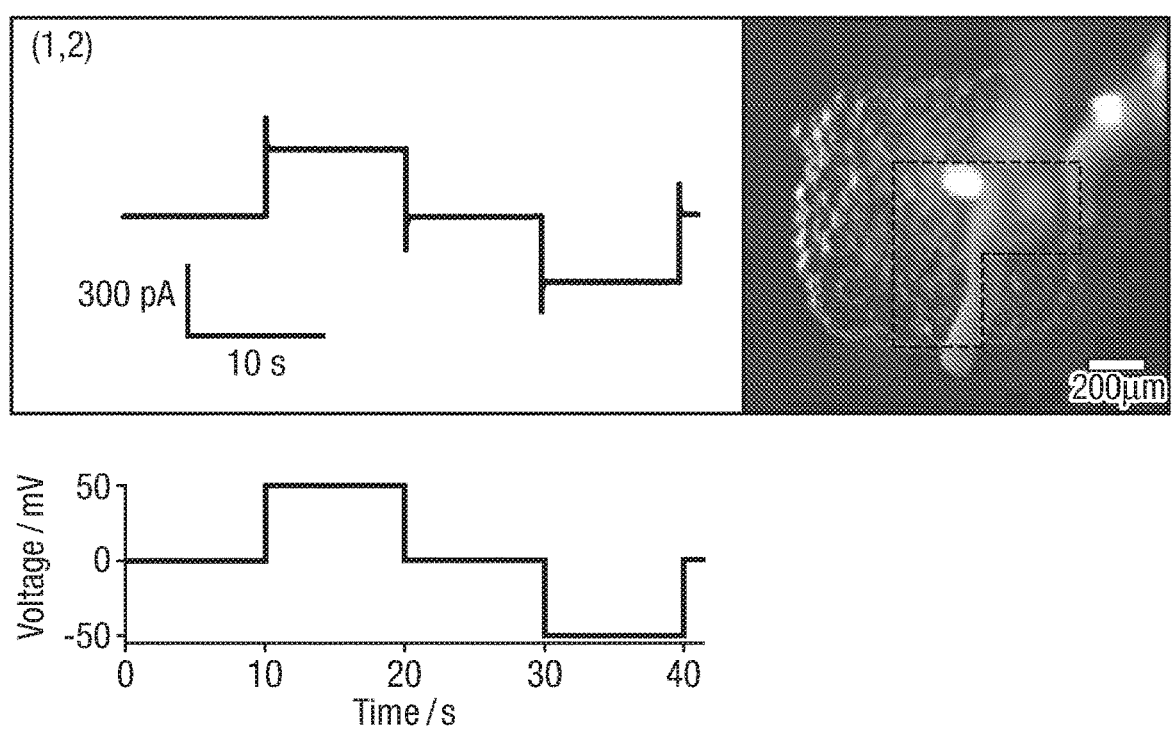
Figure 19C:
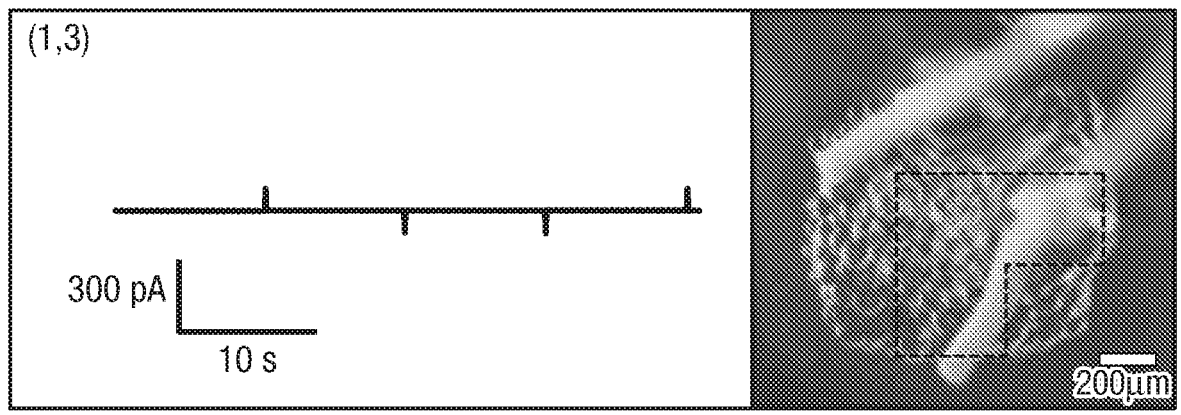
Figure 19D:
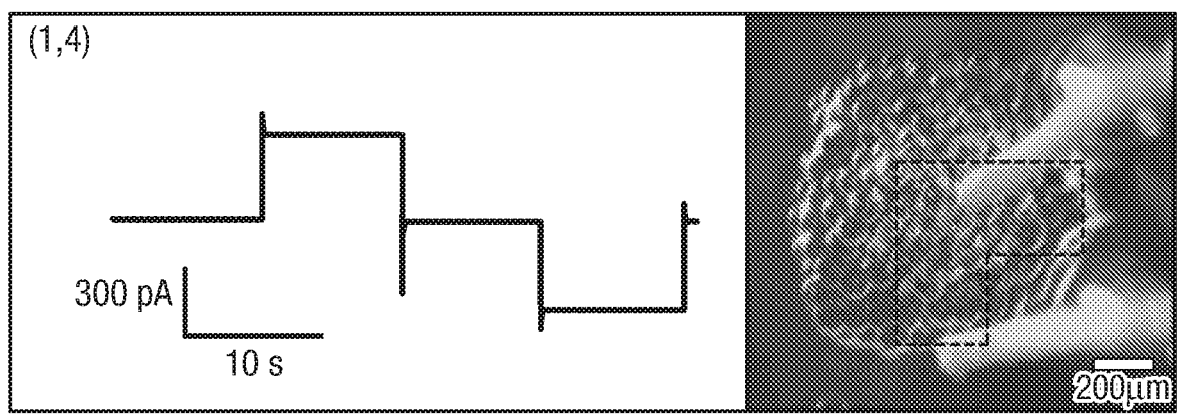
Figure 19E:
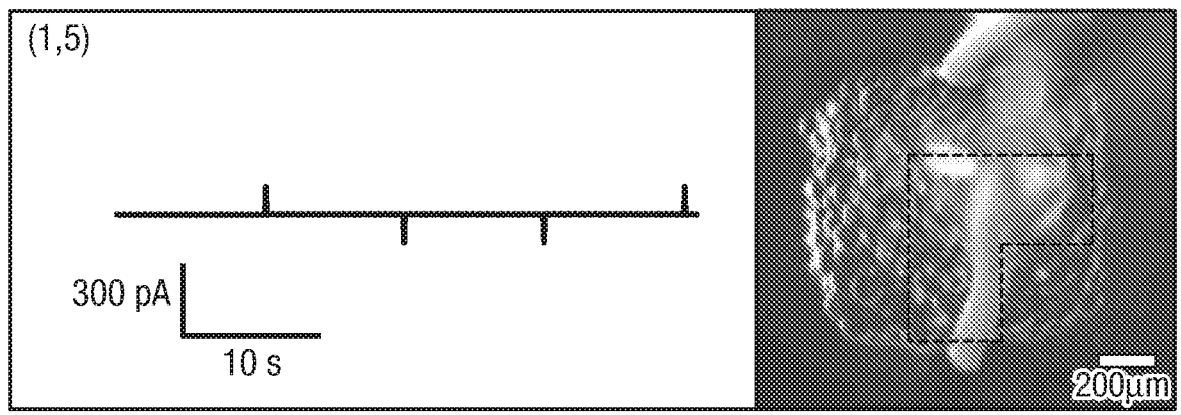
Figure 19F:
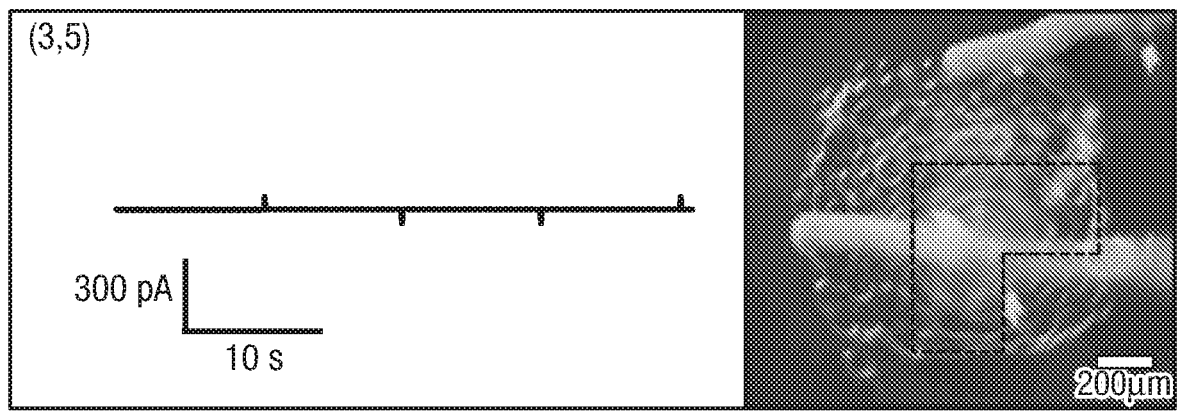

To fully exploit the use of light, the inventors aimed to light-pattern 2D pathways through 3D printed synthetic tissues that contained LA-DNA in all the droplets. Using a field diaphragm on a fluorescence light microscope, the inventors were able to illuminate a small circular area of the synthetic tissues (FIG. 17). By illuminating multiple conjoined circular areas of a LA-mVenus DNA containing synthetic tissue, protein expression was only activated in the illuminated droplets (FIG. 18). Following this, LA-αHL DNA was activated in 2D light-patterned pathways in synthetic tissues (FIG. 19). Electrical communication, measured similar to the 3D printer patterned pathway, was observed both through the two ends of the light-patterned pathway (FIG. 19B) and from the side to the top (FIG. 19D). When the electrodes were placed at other points on the synthetic tissue, no electrical signal was detected (FIG. 19C-F). This illustrates that we could initiate rapid directional communication through light-patterned 2D pathways in synthetic tissues at a predetermined time.

Here, the inventors have created 3D printed and patterned synthetic tissues that contain hundreds of synthetic cells that express proteins under a tightly regulated light-activated DNA promoter. Light-activated electrical communication was achieved through 3D printed pathways in the synthetic tissues. This efficient LA-DNA technology provides a precise means to control in vitro protein expression. Therefore, it is possible to create synthetic tissues, which comprise 3D printed patterns of interconnected compartments, each with a minimal cellular functionality, which can be externally controlled by light. These synthetic tissues might be developed into controllable soft biodevices that could be interfaced with cellular tissue.

Materials and Methods

DNA sequences

| DNA name | DNA sequence | Modification |
|---|---|---|
| Amino-T7 | GAATXAAXACGACXCACXAXAGG GXCXAG (SEQ ID NO: 1) | X = C6-amino-dT |
| mV FRW | TTAACTTTAAGAAGGAGGTATACA TATGGTGAGCAAGGGCGAGGAGCT GT (SEQ ID NO: 2) | |
| mV REV | TACTCGAGAATTCCCGGGATCCTC ATTACTTGTACAGCTCGTCCATGCC G (SEQ ID NO: 3) | |
| CT-FP FRW | CGGCATGGACGAGCTGTACAAGTA ATGAGGATCCCGGGAATTCTCGAG TA (SEQ ID NO: 4) | |
| CT-FP REV | ACAGCTCCTCGCCCTTGCTCACCAT ATGTATACCTCCTTCTTAAAGTTAA AC (SEQ ID NO: 5) | |
| mC FRW | TTAACTTTAAGAAGGAGGTATACA TATGGTGAGCAAGGGCGAGGAGG ATA (SEQ ID NO: 6) | |
| mC REV | TACTCGAGAATTCCCGGGATCCTC ATTACTTGTACAGCTCGTCCATGCC G (SEQ ID NO: 7) | |
| HL-FRW | TTAACTTTAAGAAGGAGGTATACA TATGGCAGATTCTGATATTAATATT A (SEQ ID NO: 8) | |
| HL-LINK REV | AGAGCCACCTCCGCCTGAACCGCC ACCACCCGAATTTGTCATTTCTTCT TTTTCCCAA (SEQ ID NO: 9) | |
| HL-REV | TACTCGAGAATTCCCGGGATCCTC ATTAATTTGTCATTTCTTCTTTTTCC CAA (SEQ ID NO: 10) | |
| emGFP-LINK FRW | TCAGGCGGAGGTGGCTCTGGCGGT GGCGGATCGGTGAGCAAGGGCGA GGAGCTGT (SEQ ID NO: 11) | |
| CT-HL FRW | TTGGGAAAAAGAAGAAATGACAA ATTAATGAGGATCCCGGGAATTCT CGAGTA (SEQ ID NO: 12) | |
| CT-HL REV | TAATATTAATATCAGAATCTGCCA TATGTATACCTCCTTCTTAAAGTTA AAC (SEQ ID NO: 13) | |
| CT-emGFP FRW | CGGCATGGACGAGCTGTACAAGTA ATGAGGATCCCGGGAATTCTCGAG TA (SEQ ID NO: 14) | |
| CT Seq FRW | GCTAGTGGTGCTAGCCCCGC (SEQ ID NO: 15) | |
| CT Seq REV | GGGACCGCTAGCGCGGCCGC (SEQ ID NO: 16) | |
| Fusion Linker | TCGGGTGGTGGCGGTTCAGGCGGA GGTGGCTCTGGCGGTGGCGGATCG (SEQ ID NO: 17) | |
| CT REV | GATATAGTTCCTCCTTTCAG (SEQ ID NO: 18) | |

Amino-T7 Oligo Conjugation to PC-Biotin

Amino-T7 oligo (5 µL, 100 µM, ATDBio) was reacted with PC-Biotin (25 µL, 10 mM in DMF, Ambergen) with 100 mM NaHCO$_3$ in a total volume of 50 µL in a 0.5 mL LoBind Protein tube (Eppendorf). Reactions were held at room temperature in the dark for 1 h with gentle vortexing and centrifugation every 15 min, and then left at 4° C. overnight. Reactions were stopped with the addition of 350 µL 10 mM Tris·HCl pH 8.0 (Sigma) and the derivatised oligo was purified with 3 kD Amicon Ultra columns according to the manufacturer's protocol (Millipore, washed on the column four times with 350 µL 10 mM Tris·HCl pH 8.0).

Analytical HPLC examination (Agilent 1260 Infinity) of the extent of the reaction was carried out with 1 µL of purified Amino-T7-PC-Biotin separated on an Agilent Polaris 5 $C_{18}$ 5 µm, 4.6×150 mm column, with a flow of 2 mL/min. Eluting buffers were Buffer A (10 mM triethylammonium bicarbonate pH 8.5 (Sigma)) and Buffer B (acetonitrile). The gradient was 0 min—2% B, 10 min—35% B. Peaks were monitored by their absorbance at 260 nm.

The Amicon purified Amino-T7-PC-Biotin was further purified by HPLC (Agilent 1260 Infinity) with a Supelco DiscoveryBio Wide Pore $C_{18}$ 10 µm, 10×250 mm, column with a flow of 5 mL/min. Eluting buffers were Buffer A (1 M ammonium acetate, pH 7), Buffer B (acetonitrile) and Buffer C ($H_2O$). Buffer A was held at 10% throughout the whole run and the gradient for the remaining buffers was 0 min—5% B, 40 min—40% B. The method is adapted from a literature protocol (25).

HPLC-purified Amino-T7-PC-Biotin was lyophilized in LoBind Protein tubes, resuspended in 10 mM Tris·HCl pH 8.0 and concentrated with 3 kDa Amicon Ultra columns, before transfer to LoBind Protein tubes for storage.

Cloning of Genes Encoding mVenus, mCherry and αHL-GFP into the PURExpress Control Template Genes of interest were cloned into the PURExpress control template (CT) by using homologous recombination (26, 27). mVenus (mVenus N1, Addgene), mCherry (provided by Wade-Martin's lab, Department of Physiology and Anatomy, University of Oxford), α-hemolysin-NN mutant (Bayley lab, Chemical Research Laboratory, University of Oxford) and emGFP (pRSET-EmGFP, Invitrogen) were amplified with PCR primers to form linear fragments that contained overlap regions to the CT at each end. The CT was also amplified into a linear PCR fragment that contained overlap regions to each gene of interest at each end. For the αHL-GFP construct a linker region (Fusion Linker DNA sequence) was added in-between the two genes by adding overlaps of the fusion linker sequence to the end of the αHL gene and the beginning of emGFP sequence (i.e. a 3-way recombination).

All plasmids were digested to form linear fragments before PCR amplification, by using either NdeI (CT, mCherry) or HindIII (emGFP, αHL and mVenus).

PCRs for homologous recombination were carried out with Phusion High-Fidelity DNA Polymerase (NEB) master mix. PCRs were made according to the manufacturer's protocol in a total of 50 µL with 5 µL of each primer (Sigma, 10 µM) and between 5 and 15 ng of digested plasmid template. The following thermal cycle was performed: 98° C. for 30 s, 35× (98° C. for 10 s, 55° C. for 30 s, 72° C. for 30/60 s), 72° C. for 5 mins. The extension time for each PCR fragment was: CT (60 s), αHL (60 s), emGFP (60 s), mVenus (30 s) and mCherry (30 s).

In summary, plasmids were constructed so that they each contained a gene (mVenus, mCherry, αHL and αHL-GFP) in place of the control Dihydrofolate reductase (DHFR) gene in the PURE CT plasmid. Below are the combinations of PCR fragments used to construct each plasmid, with the plasmid templates and primers used to produce each amplified product for homologous recombination:

Gene encoded in PURE CT=(template plasmid A:
   primer 1+primer 2)+(template plasmid B:
   primer 3+primer 4)

mVenus.CT=(mVenus N1: mV FRW+mV REV)+(CT:
   CT-FP FRW+CT-FP REV)

mCherry.CT=(mCherry: mC FRW+mC REV)+(CT:
   CT-FP FRW+CT-FP REV)

αHL.CT=(αHL: HL FRW+HL REV)+(CT: CT-HL
   FRW+CT-HL REV)

αHL-GFP.CT=(αHL: HL FRW+HL-LINK REV)+
   (CT: CT-emGFP FRW+CT-HL REV)+(emGFP:
   emGFP-LINK FRW+mV REV)

PCR products were not purified before homologous recombination. XL-10 Gold competent E. coli cells (NEB) were thawed on ice for 30 min. Between 1 and 5 µL of PCR product (100 ng of DNA, based on agarose gel analysis) was added to 75 µL cells which were held on ice for an additional 30 min. The cells were then heat shocked for 30 s at 42° C., then held on ice for 2 min. 75 µL of Luria Broth (LB) was added to the cells and they were plated on LB Agar plates containing ampicillin (100 µg/mL). Colonies were grown in LB containing ampicillin (100 µg/mL) and the plasmids purified with Thermo GeneJet Plasmid Miniprep kits. Sequences were verified with Sanger sequencing (Source BioScience) using the primers CT-Seq FRW and CT-Seq REV (Sigma).

PCR of Genes of Interest with Amino-T7-PC-Biotin Primer

Linear DNA templates were constructed by PCR, from the cloned plasmids (above). Each linear DNA template would contain each of the genes of interest (mVenus, mCherry, αHL and αHL-GFP) downstream of the Amino-T7-PC-Biotin oligo synthesised above, by using the HPLC-purified oligo as a PCR primer. PCRs were made with DreamTaq DNA polymerase (Life Technologies) master mix according to the manufacturer's protocol in a total of 50 µL with 1.25 µL CT REV (Sigma, 10 µM), 2.5 µL Amino-T7-PC-Biotin (45 ng/µL) and 10 ng of NdeI digested CT containing the desired gene of interest. The following thermal cycle was performed: 95° C. for 3 min, 35× (95° C. for 30 s, 52.5° C. for 30 s, 72° C. for 1 min 15 s), 72° C. for 5 mins. The extension time was increased to 2 min and 15 s for αHL-GFP template.

The PCR products were purified with Thermo GeneJet PCR kits and the DNA precipitated in LoBind Protein tubes overnight at −80° C. by the addition of sodium acetate (1/10 volume, 3 M) and then ethanol (3 volumes). A DNA pellet was recovered by centrifugation at 16000 rcf for 30 min and washed twice with ice cold 80% V/V ethanol. The DNA pellet was then dried in a Speed Vac Concentrator (Savant), resuspended in 10 mM Tris·HCl pH 8.0 and transferred to a new LoBind Protein tube.

These PCR amplified genes now contain the Amino-T7-PC-Biotin promoter upstream of the coding sequences.

The above protocol was repeated for mVenus using the Amino-T7 promoter (no PC-Biotin reaction performed). This template is the control amino-only DNA template.

LA-DNA Formation with Binding of Monovalent Streptavidin

To create the LA-DNA, monovalent streptavidin (provided by the Howarth Lab, Department of Biochemistry, University of Oxford) was bound to the PCR templates containing the Amino-T7-PC-Biotin promoter.

1 µg of PCR product (final concentration of 50 ng/µL of DNA) was incubated with a 50× molar excess of monovalent streptavidin in 10 mM Tris·HCl pH 8.0 in LoBind Protein tubes for 3 h at room temperature and then overnight at 4° C. Amine-only DNA was also incubated with monovalent streptavidin.

Standard Bulk Solution UV Photocleavage of LA-DNA

UV photocleavage of the LA-DNA was performed by using a LED Driver (ThorLabs, LEDD1B, set at 1.2 mA)

connected to a 365 nm Collimator LED (ThorLabs, M365L2-C5). 10 µL of LA-DNA (50 ng/µL) was either held under ambient light or under the LED Driver (¼ power setting) at a distance of 4.5 cm for 15 min, with UV directly illuminating the solution in the open tubes. This procedure was also performed with amine-only DNA. 100 ng of each sample was run on a 1.5% w/V TAE agarose gel with a 1 kb ladder (NEB).

T7 RNA Transcription from LA-DNA

T7 RNA transcriptions (NEB, M0251) were performed according to the manufacturer's protocol with the addition of Murine RNAse Inhibitor (NEB, MB0314). The final concentration of LA-DNA or amine-only DNA (coding for mVenus) in the T7 RNA transcription was 8 ng/µL with a total reaction volume of 5 µL.

Following assembly of the reaction mixes on ice, the samples were either held under ambient light or photocleaved under the same conditions as a standard bulk photocleavage. The reactions were then held at 37° C. for 1 h. DNAse I (NEB, M0303) was then added to the tubes, which were held at 37° C. for an additional 20 min. EDTA was then added (5 mM final concentration) and the enzymes denatured at 75° C. for 10 min. The entire sample was then ran on a 2% w/V TAE agarose gel with a ssRNA ladder (NEB, N0364).

PURExpress Protein Expression in Bulk from LA-DNA

Protein expression was performed with the PURExpress In Vitro Protein Synthesis kit (NEB, E6800) according to the manufacturer's protocol with the addition of Murine RNAse Inhibitor (NEB, MB0314). Final reaction volumes were between 2.5 and 4 µL. Poly(ethylene glycol) 4,000 (Sigma) was added to the reactions at a final concentration of 1% w/v. LA-DNA or amine-only DNA (coding for mVenus) was added to a final concentration of 5-10 ng/µL (depending on the activity of the batch of PURExpress).

Following assembly of the reaction mixes on ice, the samples were either held under ambient light or photocleaved under the same conditions as a standard bulk photocleavage. The tubes were then held at 37° C. for 3 h. 0.5 µL aliquots were removed at 0, 1, 2 and 3 h and worked up with 24.4 µL 10 mM Tris·HCl pH 8.0. Triplicate reactions were performed for each DNA with and without UV irradiation.

The fluorescence intensity of these Tris·HCl worked up aliquots were measured using a Cary Eclipse Fluorescence Spectrophotometer (Varian) with a 30 µL fluorescence cell (Hellma-Analytics, 105.252-QS). The settings on the fluorescence spectrophotometer were as follows: excitation at 490 nm, emission from 520 nm to 575 nm with an excitation slit of 20 nm, scan control at slow and PMT detector voltage at high. 3 scans were taken per sample. Mean fluorescence intensity at 530 nm (maximum for mVenus) of triplicate samples were plotted against time with the standard deviation of each value.

Confocal Microscopy

Fluorescence microscopy was performed with a confocal microscope (Leica, SP5) using a 10× objective lens (Leica, HC PL FLUOTAR) under the differential interference contrast polarising setting. Image resolutions were set at 512× 512 pixel and four frame averages were taken per image. The overall laser power was set to 20%, smart offset was set to −1% and the pinhole was held at 100 µm throughout.

The settings below were used for each fluorophore:
mVenus: 514 nm laser at 30%, PMT detector between 525-575 nm and smart gain at 800.
mCherry: 543 nm laser at 40%, PMT detector between 600-700 nm and smart gain at 1100.
emGFP: 488 nm laser at 25%, PMT detector between 500-600 nm and smart gain at 900.
TAMRA: 543 nm laser at 15%, PMT detector between 560-625 nm and smart gain at 725.

All fluorescence images were analysed using Fiji (ImageJ). Line profiles from images are shown in the same figures. Any brightness/contrast changes made to the images were the same for both +UV and −UV image sets.

Preparation of DPhPC and DPPE-mPEG2000 Lipid in Oil Stocks

DPhPC (Avanti, 4E 16:0 PC) and DPPE-mPEG2000 (Avanti, 16:0 PEG2000 PE) were weighed out, dissolved in chloroform and then added to a new glass vial to give a total of $2 \times 10^{-6}$ moles of total lipid. Two different molar fractions of the two lipids were used, 10% and 15% DPPE-mPEG2000. The chloroform was evaporated in a nitrogen stream and the residue desiccated for >3 h, before storage under argon gas at −20° C. Before use, the dried films were dissolved in hexadecane (Sigma) and silicone oil (AR-20, Sigma) was then added to a total volume of 2 mL, for a 1 mM total lipid concentration. Three different volume ratios of hexadecane and silicone oil were used, 50:50, 55:45 and 40:60 (hexadecane:silicone oil). Both oils were filtered with Millex GP 0.22 µm filters (Millipore) before addition to the lipid.

General Electrical Recording Protocol

Electrical recordings were conducted with a patch-clamp amplifier (Axopatch 200B, Axon Instruments) with its head stage, contained in a faraday cage, connected to two Ag/AgCl wire electrodes (Sigma) of 100 µm diameter. The tips of both electrodes were coated with a hydrogel at 0.5% w/v (Sigma, low gelling agarose). The electrodes were then inserted in droplets or placed on the sides of networks with the aid of micromanipulators (Narishige, NMN-21). A current signal was obtained by episodic acquisition and filtered at 2 kHz. Data were collected at 10 kHz at an interval of 100 µs and ×5 gain with a Digidata 1440A digitizer (Axon Instruments). Using an analog output, a waveform epoch with steps at 0 mV, 50 mV, 0 mV, −50 mV, 0 mV, each with a duration of 10 s, was used to detect current between droplet pairs or through networks. Data were analysed by Clampfit (version 10.3, Axon Instruments), filtering with a low pass Bessel (8-pole), −3 dB cutoff of 40 Hz. All electrical recordings were conducted at 22.0±1.5° C.

PURExpress Protein Expression in Droplets from LA-DNA

PURExpress reactions for droplet expression were prepared as described for bulk studies (above). Reactions were held on ice until droplet formation.

Poly(methyl methacrylate) (PMMA) chips were micromachined using a CNC milling machine (Roland, Modela MDX-40) to create arrays of circular wells of 1.5 mm diameter to which the lipid in oil stocks were added. 50 nL droplets were made into each of these wells using a 0.5 µL syringe (Hamilton, 7000.5 KH) observed through a microscope (Olympus, SZX10).

To create a droplet-interface bilayer (DIB) of two synthetic cells, a single 50 nL droplet was placed in a well. Then the second droplet was dropped on top or next to the first droplet, and the two droplets were left to incubate for at least 5 min. With the DPhPC and DPPE-mPEG2000 lipid mixes, the monolayers form almost instantaneously, so there was no need for incubation before bringing the two droplets together. Following droplet and DIB formation, all samples were held in a closed petri dish along with a smaller petri dish containing water to act as a hydration chamber.

Standard Droplet/Network UV Photocleavage of LA-DNA

All droplets and networks under lipid in oil mixes were UV treated with the same set up as the bulk solutions, however the LED Driver was set at ⅝ power setting at a distance of 4.5 cm for 5 min. The UV set up illuminated the droplets/networks from above, so the UV only traveled through the lipid in oil before reaching the droplets/networks. As all UV illumination was performed from above and confocal imaging was performed from below, fluorescent signal from the confocal demonstrated that the UV penetrated all the way through the networks and activated the synthetic cells on the bottom of the networks.

LA-mVenus and LA-mCherry Droplet Experiments

Two droplets both containing either LA-mVenus or LA-mCherry DNA were incubated together to form a DIB in 10% DPPE-mPEG2000/DPhPC in 50:50 V:V hexadecane:silicone oil. These droplets were either held under ambient light or subjected to the standard droplet photocleavage.

The droplets were then incubated at 25° C. for 18 h and the fluorescence signal was imaged with the fluorescence confocal microscope under the settings for each fluorophore.

LA-αHL-GFP Droplet Experiment

Two droplets, one containing LA-αHL-GFP DNA and the second no DNA were incubated together to form a DIB in 15% DPPE-mPEG2000/DPhPC in 50:50 V:V hexadecane:silicone oil. The droplets were either held under ambient light or subjected to the standard droplet photocleavage.

The droplets were then incubated at 25° C. for 18 h and then the fluorescence signal imaged with the fluorescence confocal microscope under the settings for each fluorophore.

LA-αHL and TAMRA Droplet Diffusion Experiment

Two droplets, one containing LA-αHL DNA and the second TAMRA (20 μM) were incubated together to form a DIB in 15% DPPE-mPEG2000/DPhPC in 50:50 V:V hexadecane:silicone oil. The droplets were either held under ambient light or subjected to the standard droplet photocleavage.

The droplets were then incubated at 25° C. for 18 h and then the fluorescence signal imaged with the fluorescence confocal microscope under the settings for each fluorophore.

LA-αHL Droplet Electrical Recording Experiment

PURExpress reactions were made up as described previously with one exception, the final DNA concentration of LA-αHL was 0.5 ng/μL.

Single droplets were made containing LA-αHL in 10% DPPE-mPEG2000/DPhPC in 50:50 V:V hexadecane:silicone oil. These droplets were either held under ambient light or subjected to the standard droplet photocleavage. These single droplets were incubated at 37° C. for 10 min.

Electrical Recording Analysis:

Using micromanipulators, hydrogel-coated electrodes were brought in contact with their respective droplets in the lipid in oil solution. Once a droplet spontaneously adheres to the hydrogel coating, the droplet is lifted off the surface of the chamber with the micromanipulators. As a result, the droplet hangs on the electrode's tip. The two droplets, one attached to each electrode are brought together to form a bilayer. In order to confirm a bilayer has been formed the capacitance is measured during episodic stimulation with a triangular wave that oscillates between +15 mV and −15 mV every 30 ms. A capacitance of ≥20 pF demonstrates that a bilayer has been formed. Once a bilayer is achieved, the droplets are evaluated as by the general electrical recording protocol.

3D Printing Networks of PURExpress Droplets

PURExpress reactions for 3D network expression were prepared as described for bulk studies (above). The reaction mixes were held on ice until network printing.

Apart from the optimisation experiments, all 3D printing was performed in 10% DPPE-mPEG2000/DPhPC in 40:60 hexadecane:silicone oil.

3D droplet printing was generally performed as previously described (11). Before use, the hand-made glass printing nozzles were oxygen plasma treated (Diener Electronic, Femto version A) for 8 min (5-10 SCCM). Before loading each solution into a nozzle, it was washed with soap (Bucks, Detsan neutral detergent), water and then ethanol (with nitrogen gas used to remove each wash solution from the nozzle), and then left to air dry for 10 min before use. The hexadecane plug and PURExpress solutions were loaded into the nozzle from a CNC milled array with 1.5 mm diameter wells. The networks were printed into truncated glass cuvettes (3.1125/SOG/10, Starna) containing the optimized lipid in oil solution. Maps representing each layer of each 3D printed structure are described for each experiment. The piezo microcontroller was replicated, but with a higher voltage output (±33 V) by the electronics workshop (Department of Chemistry, University of Oxford). The diameter of the droplets was tuned to ~75 μm, by altering the voltage and pulse of the piezo, prior to automated printing. Following network formation, all samples were held in a closed petri dish along with a smaller petri dish containing water to act as a hydration chamber.

LA-mVenus and LA-mCherry 3D Network Experiments 3D printed droplet networks were created from either LA-mVenus or LA-mCherry DNA containing solutions. Maps for these structures were 3 (mCherry) or 4 (mVenus) layers of 7×8 droplets. Throughout printing, the PURExpress solution was held under ambient light in the nozzle. After printing, the droplet networks were either held under ambient light or subjected to the standard droplet photocleavage.

The droplet networks were then incubated at 25° C. for 18 h and the fluorescence signal imaged with the fluorescence confocal microscope under the settings for the appropriate fluorophore.

LA-αHL 3D Network Electrical Recording Experiment 3D printed droplet networks were created with PURExpress reactions that contained LA-αHL DNA at a final DNA concentration of 0.5 ng/μL. Maps for these structures were 6 layers of 7×8 droplets. Throughout printing, the PURExpress solution was held under ambient light in the nozzle. After printing, these droplet networks were either held under ambient light or subjected to the standard droplet photocleavage.

These droplet networks were then incubated at 37° C. for 10 min.

Electrical Recording Analysis:

The tips of the electrodes were bent to aid their placement onto the sides of the networks before hydrogel-coating. By using micromanipulators, the electrodes were brought in contact with a network, in the lipid in oil solution. The droplets on the sides of the networks spontaneously adhere to the electrodes. The capacitance is tested during episodic stimulation with a triangular wave that oscillates between +15 mV and −15 mV every 30 ms. A capacitance of ≥20 pF demonstrates that the droplets the electrodes are attached to, on each side of a single network, are connected by continuous droplet bilayers through the network. The networks were then evaluated as by the general electrical recording protocol.

LA-Venus 3D-Printed Pathway Experiment

A 3D-printed network was created with an mVenus pathway through a network containing no DNA, using two PURE solutions containing LA-mVenus DNA and no DNA.

Maps for each 2D layer of these structures are shown in FIG. 20.

These 3D-printing pathway maps (left images in FIG. 20) were created in Microsoft Paint where a single pixel equates to a single droplet. Also shown is the maps recreated in the printing software (right images in FIG. 20), and demonstrate the dimensions and number of droplets in each layer of each map. The pixels enclosed by the white lines correspond to a printed droplet. The black area pixels correspond to no printed droplet.

Initially, 5 layers of map A (FIG. 20(A)) were printed with the LA-mVenus DNA solution. Then 4 layers of map B (FIG. 20(B)) were printed, with the no DNA solution, around the L channel structure already printed. Immediately following this, 4 layers of map C (FIG. 20(C)) were printed, with the same no DNA solution, on top of the whole network structure.

Throughout printing, the PURExpress solution was held under ambient light in the nozzle. After printing, the droplet networks were subjected to the standard droplet photocleavage. The droplet networks were then incubated at 25° C. for 18 h and then the fluorescence signal imaged with the fluorescence confocal microscope under the settings for the appropriate fluorophore.

LA-αHL Patterned 3D Channel Experiment

A 3D-printed network was created with a αHL pathway through a network containing no DNA, using two PURE solutions containing LA-αHL DNA (at a final DNA concentration of 0.5 ng/μL) and no DNA.

Maps for this structure are the same for the LA-Venus 3D printed pathway experiment (FIG. 20).

Initially, 5 layers of map A were printed with the LA-αHL DNA solution. Then 4 layers of map B were printed, with the no DNA solution, around the L channel structure already printed. Immediately following this, 4 layers of map C were printed, with the same no DNA solution, on top of the whole network structure.

Throughout printing, the PURExpress solution was held under ambient light in the nozzle. After printing, these droplet networks were subjected to the standard droplet photocleavage. The droplet networks were then incubated at 37° C. for 10 min.

Electrical Recording Analysis:

Electrical recording experiments were carried out on these networks in the same manner as the LA-αHL 3D network electrical recording experiment. Initially, electrical recording measurements were made across the two sides of the network connected with the LA-αHL pathway. Following this, one electrode was removed from the network and placed on a different side, using the micromanipulator. This was repeated until all the configurations shown in FIG. 16 were analysed.

LA-mVenus and LA-αHL Light-Patterned 2D Channel 3D printed droplet networks were created from either LA-mVenus (concentration as above) or LA-αHL DNA (at a final DNA concentration of 0.5 ng/μL) containing solutions. Maps for these structures were 4 layers of 9×11 droplets. Throughout printing, the PURExpress solution was held under ambient light in the nozzle.

After printing, shapes were illuminated into the network using a Leica DMi8 wide-field light microscope, with a HCX PL FL L 40× lens and an illumination field diaphragm. Illumination was carried out for 1 minute using a DAPI filter cube, ¼ shutter intensity, 10% illumination intensity and a circular illumination field setting of 2. The pathways were drawn into the networks by illuminating multiple conjoined restricted circles in the desired location.

The LA-mVenus droplet networks were then incubated at 25° C. for 18 h and the fluorescence signal imaged with the fluorescence confocal microscope under the settings for the appropriate fluorophore.

The LA-αHL droplet networks were incubated at 37° C. for 10 min. Electrical recording experiments were then carried out on these networks in the same manner as the LA-αHL patterned 3D channel experiment.

REFERENCES

1. D. S. Tawfik, A. D. Griffiths, Man-made cell-like compartments for molecular evolution. *Nat. Biotechnol.* 16, 652 (1998).
2. V. Noireaux, A. Libchaber, A vesicle bioreactor as a step toward an artificial cell assembly. *Proc. Natl. Acad. Sci. U.S.A.* 101, 17669 (2004).
3. G. Murtas, Y. Kuruma, P. Bianchini, A. Diaspro, P. L. Luisi, Protein synthesis in liposomes with a minimal set of enzymes. *Biochem. Biophys. Res. Commun.* 363, 12 (2007).
4. T. Nishikawa, T. Sunami, T. Matsuura, N. Ichihashi, T. Yomo, Construction of a gene screening system using giant unilamellar liposomes and a fluorescence-activated cell sorter. *Anal. Chem.* 84, 5017 (2012).
5. S. Fujii, T. Matsuura, T. Sunami, Y. Kazuta, T. Yomo, In vitro evolution of alpha-hemolysin using a liposome display. *Proc. Natl. Acad. Sci. U.S.A.* 110, 16796 (2013).
6. N. Ichihashi et al., Darwinian evolution in a translation-coupled RNA replication system within a cell-like compartment. *Nat. Commun.* 4, 2494 (2013).
7. W. C. Lu, A. D. Ellington, In vitro selection of proteins via emulsion compartments. *Methods* 60, 75 (2013).
8. M. Kaneda et al., Direct formation of proteo-liposomes by in vitro synthesis and cellular cytosolic delivery with connexin-expressing liposomes. *Biomaterials* 30, 3971 (2009).
9. R. Lentini et al., Integrating artificial with natural cells to translate chemical messages that direct E. coli behaviour. *Nat. Commun.* 5, 4012 (2014).
10. E. Karzbrun, A. M. Tayar, V. Noireaux, R. H. Bar-Ziv, Programmable on-chip DNA compartments as artificial cells. *Science* 345, 829 (2014).
11. G. Villar, A. D. Graham, H. Bayley, A tissue-like printed material. *Science* 340, 48 (2013).
12. M. Liu, H. Asanuma, M. Komiyama, Azobenzene-tethered T7 promoter for efficient photoregulation of transcription. *J. Am. Chem. Soc.* 128, 1009 (2006).
13. A. Estevez-Torres et al., Sequence-independent and reversible photocontrol of transcription/expression systems using a photosensitive nucleic acid binder. *Proc. Natl. Acad. Sci. U.S.A.* 106, 12219 (2009).
14. A. Diguet et al., UV-induced bursting of cell-sized multicomponent lipid vesicles in a photosensitive surfactant solution. *J. Am. Chem. Soc.* 134, 4898 (2012).
15. J. Olejnik, S. Sonar, E. Krzymanska-Olejnik, K. J. Rothschild, Photocleavable biotin derivatives: a versatile approach for the isolation of biomolecules. *Proc. Natl. Acad. Sci. U.S.A.* 92, 7590 (1995).
16. M. Howarth et al., A monovalent streptavidin with a single femtomolar biotin binding site. *Nat. Methods* 3, 267 (2006).
17. Y. Shimizu et al., Cell-free translation reconstituted with purified components. *Nat. Biotechnol.* 19, 751 (2001).
18. Y. Shimizu, T. Kanamori, T. Ueda, Protein synthesis by pure translation systems. *Methods* 36, 299 (2005).
19. H. Bayley et al., Droplet interface bilayers. *Mol. Biosyst.* 4, 1191 (2008).

20. M. A. Holden, D. Needham, H. Bayley, Functional bionetworks from nanoliter water droplets. *J. Am. Chem. Soc.* 129, 8650 (2007).
21. W. L. Hwang, M. A. Holden, S. White, H. Bayley, Electrical behavior of droplet interface bilayer networks: experimental analysis and modeling. *J. Am. Chem. Soc.* 129, 11854 (2007).
22. G. Villar, A. J. Heron, H. Bayley, Formation of droplet networks that function in aqueous environments. *Nat. Nanotechnol.* 6, 803 (2011).
23. R. Syeda, M. A. Holden, W. L. Hwang, H. Bayley, Screening blockers against a potassium channel with a droplet interface bilayer array. *J. Am. Chem. Soc.* 130, 15543 (2008).
24. B. Alberts, *Molecular biology of the cell*. (Garland Science, New York, ed. 6th, 2014), pp. 1464.
25. A. P. Sanzone, A. H. El-Sagheer, T. Brown, A. Tavassoli, Assessing the biocompatibility of click-linked DNA in *Escherichia coli. Nucleic Acids Res.* 40, 10567 (2012).
26. P. Bubeck, M. Winkler, W. Bautsch, Rapid cloning by homologous recombination in vivo. *Nucleic Acids Res.* 21, 3601 (1993).
27. Y. Zhang, J. P. Muyrers, G. Testa, A. F. Stewart, DNA cloning by homologous recombination in *Escherichia coli. Nat. Biotechnol.* 18, 1314 (2000).

The invention claimed is:

1. An activatable promoter comprising a nucleotide promoter sequence and a transcription inhibition moiety, wherein:
   a) the transcription inhibition moiety comprises a complex of a protein and small molecule;
   b) the small molecule is coupled to a component of the nucleotide promoter sequence via a photocleavable moiety, wherein the component of the nucleotide promoter sequence is one or more nucleotide bases or nucleotide base analogues, and wherein the one or more nucleotide bases or nucleotide base analogues comprises a thymine;
   c) the photocleavable moiety comprises a nitroaryl group and a diamine linker, and the transcription inhibition moiety and the photocleavable moiety are coupled to the thymine via the diamine linker, and the small molecule is coupled to the diamine linker via the nitroaryl group;
   d) the diamine linker and thymine form a C6-amino-dT or a C6-amino-T; and
   e) the nucleotide promotor sequence is configured to be activated when the transcription inhibition moiety is uncoupled from the activatable promoter by cleavage of the photocleavable moiety.

2. The activatable promoter according to claim 1, wherein the nitroaryl group of the photocleavable moiety is 2-nitrobenzyl.

3. The activatable promoter according to claim 1, wherein the small molecule is biotin and the protein is streptavidin.

4. An expression system comprising the activatable promoter according to claim 1 operably linked to an open reading frame or a gene.

5. The expression system according to claim 4, wherein the open reading frame or gene encodes a membrane protein.

6. The expression system according to claim 5, wherein the membrane protein is an a-hemolysin (aHL) pore protein.

7. The expression system according to claim 5, wherein the membrane protein comprises a pump, a channel, a pore, a receptor protein, a transporter protein, or a protein which effects cell recognition or a cell-to-cell interaction.

8. The expression system according to claim 4, wherein the system is operably configured for use with bacteriophage transcription components.

9. The expression system according to claim 4, wherein the nucleotide promoter sequence comprises a T7 promoter.

10. The expression system according to claim 4, wherein the system is operably configured for use with prokaryotic transcription components.

11. The expression system according to claim 10, wherein the prokaryotic transcription components are bacterial transcription components.

12. The expression system according to claim 4, wherein the system is operably configured for use with eukaryotic transcription components.

13. The expression system according to claim 12, wherein the system is operably configured for use with insect or mammalian transcription components.

14. The expression system according to claim 4, further comprising one or more additional transcriptional elements.

15. The expression system according to claim 14, wherein the transcriptional element is an enhancer.

16. A vector comprising an expression system according to claim 4.

17. The vector according to claim 16, wherein the vector is a linear double-stranded DNA molecule or a continuous double-stranded DNA molecule.

18. The vector according to claim 16, wherein the vector is a viral vector.

19. A delivery system comprising a vector according to claim 18, wherein the delivery system comprises a viral delivery system.

20. The vector according to claim 18, wherein the vector is a retrovirus, lentivirus, adenovirus, adeno-associated virus or herpes simplex virus vector.

21. A delivery system comprising the vector according to claim 16, wherein the delivery system comprises a yeast system, a lipofection system, a microinjection system, a biolistic system, virosomes, liposomes, immunoliposomes, polycations, lipid: nucleic acid conjugates or artificial virions.

22. A method of expressing a transcript, the method comprising: contacting the activatable promoter according to claim 1 with an uncoupling agent, the agent being capable of uncoupling the transcription inhibition moiety from the component of the nucleotide promoter sequence; whereupon the transcript is expressed following uncoupling.

23. The method according to claim 22, wherein the activatable promoter is comprised in an expression system or wherein the activatable promoter is comprised in a vector.

24. The method according to claim 22, wherein the uncoupling agent is electromagnetic radiation.

25. The method according to claim 24, wherein the nitroaryl group of the photocleavable moiety is 2-nitrobenzyl.

26. The method according to claim 24, wherein the electromagnetic radiation is ultra violet (UV).

27. The method according to claim 24, wherein the electromagnetic radiation is infra-red (IR).

28. The activatable promoter according to claim 1, wherein the small molecule is digoxigenin (DIG) and the protein is a DIG antibody.

29. The activatable promoter according to claim 1, wherein the nitroaryl group is a nitrobenzyl group.

* * * * *

SEQUENCE LISTING

```
<160> NUMBER OF SEQ ID NOS: 18

<210> SEQ ID NO 1
<211> LENGTH: 29
<212> TYPE: DNA
<213> ORGANISM: Artificial Sequence
<220> FEATURE:
<223> OTHER INFORMATION: Amino-T7
<220> FEATURE:
<221> NAME/KEY: misc_feature
<222> LOCATION: (5)..(5)
<223> OTHER INFORMATION: C6-amino-dT
<220> FEATURE:
<221> NAME/KEY: misc_feature
<222> LOCATION: (8)..(8)
<223> OTHER INFORMATION: C6-amino-dT
<220> FEATURE:
<221> NAME/KEY: misc_feature
<222> LOCATION: (14)..(14)
<223> OTHER INFORMATION: C6-amino-dT
<220> FEATURE:
<221> NAME/KEY: misc_feature
<222> LOCATION: (18)..(18)
<223> OTHER INFORMATION: C6-amino-dT
<220> FEATURE:
<221> NAME/KEY: misc_feature
<222> LOCATION: (20)..(20)
<223> OTHER INFORMATION: C6-amino-dT
<220> FEATURE:
<221> NAME/KEY: misc_feature
<222> LOCATION: (25)..(25)
<223> OTHER INFORMATION: C6-amino-dT
<220> FEATURE:
<221> NAME/KEY: misc_feature
<222> LOCATION: (27)..(27)
<223> OTHER INFORMATION: C6-amino-dT

<400> SEQUENCE: 1
gaattaatac gactcactat agggtctag                                           29

<210> SEQ ID NO 2
<211> LENGTH: 50
<212> TYPE: DNA
<213> ORGANISM: Artificial Sequence
<220> FEATURE:
<223> OTHER INFORMATION: mV FRW

<400> SEQUENCE: 2
ttaactttaa gaaggaggta tacatatggt gagcaagggc gaggagctgt                    50

<210> SEQ ID NO 3
<211> LENGTH: 50
<212> TYPE: DNA
<213> ORGANISM: Artificial Sequence
<220> FEATURE:
<223> OTHER INFORMATION: mV REV
```

```
<400> SEQUENCE: 3
tactcgagaa ttcccgggat cctcattact tgtacagctc gtccatgccg              50

<210> SEQ ID NO 4
<211> LENGTH: 50
<212> TYPE: DNA
<213> ORGANISM: Artificial Sequence
<220> FEATURE:
<223> OTHER INFORMATION: CT-FP FRW

<400> SEQUENCE: 4
cggcatggac gagctgtaca agtaatgagg atcccgggaa ttctcgagta              50

<210> SEQ ID NO 5
<211> LENGTH: 52
<212> TYPE: DNA
<213> ORGANISM: Artificial Sequence
<220> FEATURE:
<223> OTHER INFORMATION: CT-FP REV

<400> SEQUENCE: 5
acagctcctc gcccttgctc accatatgta tacctccttc ttaaagttaa ac           52

<210> SEQ ID NO 6
<211> LENGTH: 50
<212> TYPE: DNA
<213> ORGANISM: Artificial Sequence
<220> FEATURE:
<223> OTHER INFORMATION: mC FRW

<400> SEQUENCE: 6
ttaactttaa gaaggaggta tacatatggt gagcaagggc gaggaggata              50

<210> SEQ ID NO 7
<211> LENGTH: 50
<212> TYPE: DNA
<213> ORGANISM: Artificial Sequence
<220> FEATURE:
<223> OTHER INFORMATION: mC REV

<400> SEQUENCE: 7
tactcgagaa ttcccgggat cctcattact tgtacagctc gtccatgccg              50

<210> SEQ ID NO 8
<211> LENGTH: 50
<212> TYPE: DNA
<213> ORGANISM: Artificial Sequence
<220> FEATURE:
<223> OTHER INFORMATION: HL-FRW

<400> SEQUENCE: 8
ttaactttaa gaaggaggta tacatatggc agattctgat attaatatta              50

<210> SEQ ID NO 9
<211> LENGTH: 58
<212> TYPE: DNA
<213> ORGANISM: Artificial Sequence
<220> FEATURE:
<223> OTHER INFORMATION: HL-LINK REV

<400> SEQUENCE: 9
agagccacct ccgcctgaac cgccaccacc cgaatttgtc atttcttctt tttcccaa     58

<210> SEQ ID NO 10
```

<211> LENGTH: 53
<212> TYPE: DNA
<213> ORGANISM: Artificial Sequence
<220> FEATURE:
<223> OTHER INFORMATION: HL-REV

<400> SEQUENCE: 10
tactcgagaa ttcccgggat cctcattaat ttgtcatttc ttcttttttcc caa        53

<210> SEQ ID NO 11
<211> LENGTH: 55
<212> TYPE: DNA
<213> ORGANISM: Artificial Sequence
<220> FEATURE:
<223> OTHER INFORMATION: emGFP-LINK FRW

<400> SEQUENCE: 11
tcaggcggag gtggctctgg cggtggcgga tcggtgagca agggcgagga gctgt        55

<210> SEQ ID NO 12
<211> LENGTH: 53
<212> TYPE: DNA
<213> ORGANISM: Artificial Sequence
<220> FEATURE:
<223> OTHER INFORMATION: CT-HL FRW

<400> SEQUENCE: 12
ttgggaaaaa gaagaaatga caaattaatg aggatcccgg gaattctcga gta        53

<210> SEQ ID NO 13
<211> LENGTH: 52
<212> TYPE: DNA
<213> ORGANISM: Artificial Sequence
<220> FEATURE:
<223> OTHER INFORMATION: CT-HL REV

<400> SEQUENCE: 13
taatattaat atcagaatct gccatatgta tacctccttc ttaaagttaa ac        52

<210> SEQ ID NO 14
<211> LENGTH: 50
<212> TYPE: DNA
<213> ORGANISM: Artificial Sequence
<220> FEATURE:
<223> OTHER INFORMATION: CT-emGFP FRW

<400> SEQUENCE: 14
cggcatggac gagctgtaca agtaatgagg atcccgggaa ttctcgagta        50

<210> SEQ ID NO 15
<211> LENGTH: 20
<212> TYPE: DNA
<213> ORGANISM: Artificial Sequence
<220> FEATURE:
<223> OTHER INFORMATION: CT Seq FRW

<400> SEQUENCE: 15
gctagtggtg ctagccccgc        20

<210> SEQ ID NO 16
<211> LENGTH: 20
<212> TYPE: DNA
<213> ORGANISM: Artificial Sequence
<220> FEATURE:
<223> OTHER INFORMATION: CT Seq REV

<400> SEQUENCE: 16

```
gggaccgcta gcgcggccgc                                              20

<210> SEQ ID NO 17
<211> LENGTH: 48
<212> TYPE: DNA
<213> ORGANISM: Artificial Sequence
<220> FEATURE:
<223> OTHER INFORMATION: Fusion Linker

<400> SEQUENCE: 17
tcgggtggtg gcggttcagg cggaggtggc tctggcggtg gcggatcg               48

<210> SEQ ID NO 18
<211> LENGTH: 20
<212> TYPE: DNA
<213> ORGANISM: Artificial Sequence
<220> FEATURE:
<223> OTHER INFORMATION: CT REV

<400> SEQUENCE: 18
gatatagttc ctcctttcag                                              20
```